US008883415B2

(12) United States Patent
Haugland et al.

(10) Patent No.: US 8,883,415 B2
(45) Date of Patent: *Nov. 11, 2014

(54) AZA-BENZAZOLIUM CONTAINING CYANINE DYES

(71) Applicant: Life Technologies Corporation, Carlsbad, CA (US)

(72) Inventors: Richard Haugland, Eugene, OR (US); Stephen Yue, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/784,413

(22) Filed: Mar. 4, 2013

(65) Prior Publication Data
US 2013/0178395 A1    Jul. 11, 2013

Related U.S. Application Data

(60) Continuation of application No. 13/557,065, filed on Jul. 24, 2012, now abandoned, which is a continuation of application No. 12/984,380, filed on Jan. 4, 2011, now Pat. No. 8,252,530, which is a continuation of application No. 11/756,765, filed on Jun. 1, 2007, now Pat. No. 7,871,773, which is a continuation of application No. 10/683,753, filed on Oct. 13, 2003, now Pat. No. 7,226,740, which is a division of application No. 09/557,275, filed on Apr. 24, 2000, now Pat. No. 6,664,047.

(60) Provisional application No. 60/158,859, filed on Oct. 12, 1999, provisional application No. 60/131,782, filed on Apr. 30, 1999.

(51) Int. Cl.
*C12Q 1/68* (2006.01)
*C12Q 1/02* (2006.01)
*C12Q 1/04* (2006.01)
*C12P 19/34* (2006.01)

(52) U.S. Cl.
USPC ............... 435/6.1; 435/29; 435/34; 435/91.2

(58) Field of Classification Search
USPC ..................... 435/6.1, 29, 34, 91.2
See application file for complete search history.

(56) References Cited

U.S. PATENT DOCUMENTS

| 2,269,234 A | 1/1942 | Sprague |
| 3,326,688 A | 6/1967 | Brooker et al. |

(Continued)

FOREIGN PATENT DOCUMENTS

| GB | 870753 | 7/1958 |
| JP | 05287209 | * 4/1992 |

(Continued)

OTHER PUBLICATIONS

Tuma et al. (Analytical Biochemistry 268, 278-288 1999).*

(Continued)

*Primary Examiner* — Jezia Riley
(74) *Attorney, Agent, or Firm* — Life Technologies Corporation

(57) ABSTRACT

Unsymmetrical cyanine dyes that incorporate an aza-benzazolium ring moiety are described, including cyanine dyes substituted by a cationic side chain, monomeric and dimeric cyanine dyes, chemically reactive cyanine dyes, and conjugates of cyanine dyes. The subject dyes are virtually non-fluorescent when diluted in aqueous solution, but exhibit bright fluorescence when associated with nucleic acid polymers such as DNA or RNA, or when associated with detergent-complexed proteins. A variety of applications are described for detection and quantitation of nucleic acids and detergent-complexed proteins in a variety of samples, including solutions, electrophoretic gels, cells, and microorganisms.

20 Claims, 4 Drawing Sheets

(56) References Cited

U.S. PATENT DOCUMENTS

| | | | |
|---|---|---|---|
| 4,003,750 A | 1/1977 | Heseltine et al. | |
| 4,665,024 A | 5/1987 | Mansour et al. | |
| 4,711,955 A | 12/1987 | Ward et al. | |
| 4,883,867 A | 11/1989 | Lee et al. | |
| 4,937,198 A | 6/1990 | Lee et al. | |
| 4,997,928 A | 3/1991 | Hobbs | |
| 5,047,519 A | 9/1991 | Hobbs et al. | |
| 5,171,534 A | 12/1992 | Smith et al. | |
| 5,221,518 A | 6/1993 | Mills | |
| 5,321,130 A | 6/1994 | Yue et al. | |
| 5,332,666 A | 7/1994 | Prober et al. | |
| 5,401,847 A | 3/1995 | Glazer | |
| 5,410,030 A | 4/1995 | Yue et al. | |
| 5,436,134 A | 7/1995 | Haugland et al. | |
| 5,445,946 A | 8/1995 | Roth et al. | |
| 5,459,268 A | 10/1995 | Haugland et al. | |
| 5,534,416 A | 7/1996 | Millard et al. | |
| 5,564,554 A | 10/1996 | Lawrence | |
| 5,565,554 A | 10/1996 | Glazer et al. | |
| 5,582,977 A | 12/1996 | Yue et al. | |
| 5,616,502 A | 4/1997 | Haugland et al. | |
| 5,656,449 A | 8/1997 | Yue | |
| 5,658,751 A | 8/1997 | Yue et al. | |
| 5,714,327 A | 2/1998 | Houthoff et al. | |
| 5,760,201 A | 6/1998 | Glazer | |
| 5,863,753 A | 1/1999 | Haugland et al. | |
| 5,869,689 A | 2/1999 | Zhang et al. | |
| 6,083,699 A | 7/2000 | Leushner et al. | |
| 6,664,047 B1 | 12/2003 | Haugland et al. | |
| 7,226,740 B2 | 6/2007 | Haugland et al. | |
| 7,871,773 B2 * | 1/2011 | Haugland et al. | 435/6.12 |
| 2008/0044811 A1 | 2/2008 | Haugland et al. | |

FOREIGN PATENT DOCUMENTS

| | | |
|---|---|---|
| JP | 05-287209 | 11/1993 |
| WO | WO-94/05688 | 3/1994 |
| WO | WO-96/13552 | 5/1996 |

OTHER PUBLICATIONS

JP05287209 translation.*

Barlin, Gordon B. et al., "Purine Analogues as Amplifiers of Phleomycin. IX* Some 2- and 6-Substituted Thiazolo [4,5,-b] Pyrazines, 2-Substituted Thiazolo[4,5,-c]- and Thiazolo[5,4,-b]-Pyridines and Related Compunds", *Aust. J. Chem.*, vol. 37, 1984, 1729-1737.

Barlin, Gordon B. et al., "Purine Analogues as Amplifiers of Phleomyein. Some Thiazolo[4,5-g] pyrazines and Related Compounds", *Aust. J. Chem.*, vol. 36, 1983, 983-985.

Brinkley, Michael, "A Brief Survey of Methods for Preparing Protein Conjugates with Dyes, Haptens, and Cross-Linking Reagents", *Bioconjugate Chemistry*, vol. 3, Issue 1, 1992, pp. 2-13.

Brooker, L G. et al., "Color and consitution. V. The absorption of unsymmetrical cyanines. Resonance as a basis for a classification of dyes", *Journal of the American Chemical Society*, vol. 64, Communication No. 833 From the Kodak Research Laboratories, Feb. 1942, 199-210.

Chu-Moyer, Margaret Y. et al., "Preparation of the Four Regioisomeric 2-(Methylthio)oxazolopyridines: Useful Synthons for Elaboration to 2-(Amino substituted)oxazolopyridines", *Journal of Organic Chemistry*, vol. 60, No. 17, 1995, 5721-5725.

Couture, Axel et al., "2-ARYL-OXazolo- and Thiazolopyrdines. Synthesis via Cyclization of N-(2 Chloro-3-Pyridinyl) Arylamides and Thiomides", *Heterocycles*, vol. 22, No. 6, 1984, 1383-1385.

Couture, Axel et al., "Nouvelle Methode De Synthese De Thiazolopyridines", (*French Version*) *J. Heterocyclin Chem.*, vol. 24, 1987, 1765-1769.

Ficken, et al., "Diazaines and Their Quarternary Salts Part 2", *CA 55:70677, abstract only of J of Chem Soc*, 1961, 584-588.

Ficken, G E. et al., "Diazaindenes and Their Quaternary Salts Part 1: The preparation of 2,3,3-Trimethyl-3H-1,7-diazaindene, and its Methiodides and Derived Cyanine Dyes", *Journal of Chemical Society*, 1959, 3202-3212.

Foye, William O. et al., "Antiradiation compounds XV: Condensations of carbon disulfide with amino, chloro, cyanomethyl, and sulfonamido heterocycles", *Journal of Pharmaceutical Science*, vol. 64, No. 8, Aug. 1975, 1371-1374.

Haugland, Richard P. , "Molecular Probes Handbook of Fluorescent Probes and Research Chemicals", *Sixth Edition (Subsequent Seventh and Eighth Edition updates issued on CD Rom, Molecular Probes, Inc.*, 1996, Handbook Cover—xii.

Haugland, Richard P. , "Molecular Probes Handbook of Fluorescent Probes and Research Chemicals", *Chapters 1-3*, Molecular Probes, Inc, 1996, Sixth Edition, 1996, 7/80.

Haugland, Richard P. , "Molecular Probes Handbook of Fluorescent Probes and Research Products", *Sixth Edition*, 1996, 13-15.

Haugland, Richard P. , "Molecular Probes Handbook of Fluorescent Probes and Research Products", *Ninth Edition, CD ROM, Table of Contents*, Molecular Probes, Inc., 2002, 1-6.

Haugland, Rosaria P. et al., "Coupling of Antibodies with Biotin", *The Protein Protocols Handbook*, vol. 418, Humana Press, 1996, 13-23.

Haugland, Rosaria P. et al., "Coupling of Antibodies with Biotin", *The Protein Protocols Handbook*, Humana Press, 1996, 293.

Haugland, Rosaria P. et al., "Coupling of monoclonal antibodies with biotin", *Methods in Molecular Biology*, vol. 45, 1995, 223-233.

Haugland, Rosaria P. , "Coupling of monoclonal antibodies with fluorophores", *Methods in Molecular Biology*, Monoclonal Antibody Protocols, vol. 45, 1995, pp. 205-243.

Heravi, M M. et al., "Heterocyclic monoazo dyes derived from 2-(p-aminophenyl)oxazolo-[4,5-b]pyridine and 7-(p-aminophenyl)-4H-[1,3,4]thiadiazolo-[2,3-c][1,2,4]triazin-4-one", *Indian J. Chem.*, 36B, 1997, 1025-1029.

Khanna, Ish K. et al., "Facile, Regioselective Synthesis of N-Alkylated 2,3-Diaminopyridines and Imidazo[4,5-b]pyridines", *J. Org. Chem.*, vol. 60, 1995, 960-965.

Petric, A et al., "Azido-Tetrazolo Isomerizations of Some Thiazolopyridines (1)", *J. Heterocyclin Chem.*, vol. 14, Oct. 1977, 1045-1047.

Saikachi, Haruo et al., "Studies on Compounds Related to Pyrazine. III. Synthesis of 2-Substituted Thiazolo[b]quinozaline.", *Chem. & Pharm. Bull.*, vol. 9, No. 12, Dec. 1961, 941-944.

Smith, Keith et al., "A Convenient Synthesis of 2-Substituted Thiazolo [4,5-b]pyridines via Directed Metalation", *Sulfur Letters*, vol. 18, No. 2 (not available online—BJC), 1995, 79-95.

Smith, Keith et al., "Convenient synthesis of 4-aminopyridine-3-thiol and several thiazolo[5,4-c]pyridines via direct ligation", *Chemistry and Industry*, vol. 9, May 2, 1988, 302-303.

Smith, Keith et al., "The synthesis of 2-substituted thiazolo[5,4-c]pyridines via directed methalation", *Sulfur Letters*, vol. 17, No. 4, 1994, 197-216.

Turner, James A. , "Regiospecific electrophilic substitution of aminopyridines: ortho lithiation of 2-, 3-, and 4-(pivaloylamino)pyridines", *Journal of Organic Chemistry*, vol. 48, 1983, 3401-3408.

WO 2000/066664, , "PCT International Search Report from PCT/US2000/011549", Sep. 7, 2000, 1-4.

* cited by examiner

AZA-BENZAZOLIUM CONTAINING CYANINE DYES

CROSS-REFERENCE TO RELATED APPLICATIONS

This application is a continuation of U.S. application Ser. No. 13/557,065, filed Jul. 24, 2012, which is a continuation of U.S. application Ser. No. 12/984,380, filed Jan. 4, 2011 (now U.S. Pat. No. 8,252,530), which is a continuation of U.S. application Ser. No. 11/756,765, filed Jun. 1, 2007 (now U.S. Pat. No. 7,871,773), which is a continuation of U.S. application Ser. No. 10/683,753, filed Oct. 13, 2003 (now U.S. Pat. No. 7,226,740), which is a division of U.S. application Ser. No. 09/557,275, filed Apr. 24, 2000 (now U.S. Pat. No. 6,664,047), which claims priority to U.S. Provisional Application Ser. No. 60/131,782 filed Apr. 30, 1999, and U.S. Provisional Application Ser. No. 60/158,859, filed Oct. 12, 1999, which disclosures are herein incorporated by reference in their entirety.

INTRODUCTION

1. Field of the Invention

The invention relates to cyanine dyes that possess particular utility as fluorescent stains for nucleic acids and poly (amino acids). In particular, the invention relates to materials that are unsymmetrical cyanine dyes incorporating an aza-benzazolium moiety. The subject dyes, which form fluorescent complexes in combination with nucleic acids or lipid-complexed poly(amino acids), can be used in analyzing a wide range of materials, including biological and environmental samples.

2. Background of the Invention

As researchers in the fields of molecular and cell biology increasingly utilize fluorescent probes as research tools, the ability to select the wavelength of fluorescence is becoming critical. As increasing numbers of multiple-color applications are developed, the ability to produce novel fluorescent probes with detectably distinct fluorescent signals is becoming ever more important.

Unsymmetrical cyanine dyes have previously been used as fluorescent stains for nucleic acids, see for example U.S. Pat. No. 4,883,867 to Lee, at al. (1989) and U.S. Pat. No. 4,937,198 to Lee, et al. (1990). The general spectral properties of the previously described cyanine dyes could be selected somewhat by changing the number of methine groups in the dye, and whether the dye incorporated a pyridinium or quinolinium ring system (see, for example, U.S. Pat. No. 5,321,130 to Yue et al. (1994); U.S. Pat. No. 5,410,030 to Yue at al. (1995); U.S. Pat. No. 5,436,134 to Haugland at al. (1995); U.S. Pat. No. 5,582,977 to Yue et al. (1996); U.S. Pat. No. 5,658,751 to Yue et al. (1997); and U.S. Pat. No. 5,863,753 to Haugland et al. (1999). In particular, monomethine dyes that incorporate pyridinium ring systems typically exhibit blue to blue-green fluorescence emission, while those that incorporate quinolinium ring systems exhibit green to yellow-green fluorescence emission. Trimethine dyes are substantially shifted toward red wavelengths, and pentamethine dyes are typically shifted even further, and may exhibit infrared fluorescence emission.

While the spectral properties of cyanine dyes can be finely adjusted by selection of appropriate dye substituents, there were nevertheless regions of the visible spectrum where suitable fluorescent cyanine dyes that were useful as nucleic acid stains either did not exist, or did not possess particularly favorable fluorescence properties.

The dyes of the invention incorporate additional nitrogen atoms in the aromatic benzazolium portion of the dye. The dyes of the invention exhibit a bathochromic spectral shift (a shift to longer wavelength) of approximately 30 to 50 nm relative to otherwise structurally similar cyanine dyes known in the art. This bathochromic spectral shift yields dyes that are particularly useful for excitation in the wavelength ranges between 500 nm and 600 nm and at >630 nm. Of particular importance are the dyes of the invention that exhibit absorbance maxima between 530 nm and 550 nm, as they match the principal emission lines of the mercury arc lamp (546 nm), frequency-doubled Nd-Yag laser (532 nm), and HeNe laser (543 nm).

Styryl dyes that complex with lipid-complexed poly (amino acids) have been described previously (U.S. Pat. No. 5,616,502 to Haugland et al., 1997). Cyanine dyes that incorporate a 3,4-diazaindene ring system have been described previously for use as optical sensitizers in photographic materials (British patent No. 870,753 to Ficken et al., (1961)), but their use in association with either nucleic acids or lipid-complexed proteins as fluorescent stains has not previously been described.

SUMMARY OF THE INVENTION

The present invention provides unsymmetrical aza-benzazolium containing cyanine dyes (monomers and dimers), reactive versions of the dyes, dye-conjugates and methods for detecting the presence of an analyte of interest in a sample. The analyte of interest is typically a nucleic acid or a poly (amino acid) wherein the present dyes in the form of a staining solution are combined with the sample for a sufficient amount of time to form a dye-analyte complex and are illuminated with an appropriate wavelength whereby the nucleic acid or a poly(amino acid) is detected.

The dyes of the invention form a staining solution by typically being dissolved in an organic solvent such as DMSO to form a stock solution and then diluted to an appropriate concentration in a buffered solution. The staining solution is then incubated with a sample to form the dye-analyte complex.

In one aspect of the invention the analyte is nucleic acids that may be present in solution, immobilized on a solid or semi solid matrix or present in a biological structure. Typically the nucleic acid is immobilized on solid or semi solid matrix that is selected from the group consisting of a polymeric gel, a membrane, an array, a glass slide and a polymeric particle. Preferably the nucleic acid is immobilized on a glass slide or in a gel such as an agarose gel. Alternatively, the nucleic acid is present in a biological structure that is a biological cell or portion thereof, a virus particle or a tissue section.

In another aspect of the invention the analyte is a poly (amino acid), typically the poly(amino acids) are complexed with a lipid, such as an anionic detergent. Therefore, the poly(amino acid) is typically present in solution or immobilized on or in a solid- or semi-solid matrix wherein the matrix is a polymeric gel, a membrane, an array or a polymeric particle. Typically the poly(amino acid) is immobilized on a polyacrylamide gel wherein the staining solution is combined before, during or after immobilization on the gel. Preferably the poly(amino acid) are electrophoretically separated on the polyacrylamide gel. Alternatively, the poly(amino acids) may be spotted onto a polyacrylamide gel surface such as a Hydrogel microarray slide.

Typically, the dyes of the invention are according to the following formula;

Formula I

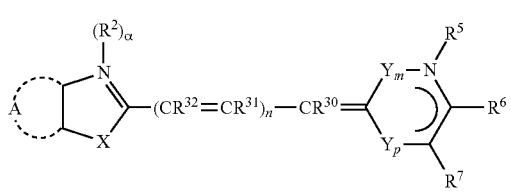

wherein A represents the atoms necessary to form one to two fused aromatic rings having 6 atoms in each ring, at least one of which is a nitrogen atom, said ring or rings being optionally further substituted one or more times by $C_1$-$C_6$ alkyl, $C_1$-$C_6$ alkoxy trifluoromethyl, halogen, BRIDGE, -L-Rx or -L-Sc;

wherein, Rx is a reactive group; Sc is a conjugated substance; and L and BRIDGE are independently a single covalent bond, or a covalent linkage;

X is O, S, Se, $NR^{15}$, or $CR^{16}R^{17}$, where $R^{15}$ is H or an alkyl group having 1-6 carbons; and $R^{16}$ and $R^{17}$, which may be the same or different, are independently alkyl groups having 1-6 carbons, or $R^{16}$ and $R^{17}$ taken in combination complete a five or six membered saturated ring;

$R^2$ is selected from the group consisting of -L-Rx, -L-Sc, TAIL, BRIDGE and an alkyl group having 1-6 carbons that is optionally substituted by sulfa, carboxy, amino, substituted amino or substituted ammonium, wherein α is 0 or 1; and TAIL is a heteroatom-containing moiety;

Y is -$CR^3$=$CR^4$- wherein p and m=0 or 1, such that p+m=1;

$R^3$, $R^4$, $R^6$, and $R^7$ are independently selected from the group consisting of hydrogen, a $C_1$-$C_6$ alkyl, a halogen, a CYCLIC SUBSTITUENT, -$OR^8$, -$SR^8$, -($NR^8R^9$), TAIL; BRIDGE, -L-Rx and -L-Sc; where $R^8$ and $R^9$ are independently a $C_1$-$C_6$ alkyl group, 1-2 alicyclic or aromatic rings; or $R^8$ and $R^9$ taken in combination are —($CH_2$)$_2$—V—($CH_2$)$_2$- where V is a single bond, —O—, —$CH_2$—, or —$NR^{10}$-, where $R^{10}$ is H or an alkyl having 1-6 carbons;

wherein CYCLIC SUBSTITUENT is a substituted or unsubstituted aryl, heteroaryl or $C_3$-$C_{10}$ cycloalkyl;

or $R^6$ and $R^7$ form a fused aromatic ring —$R^{11}$=$R^{12}$—$R^{13}$=$R^{14}$— wherein $R^{11}$, $R^{12}$, $R^{13}$, and $R^{14}$ are independently selected from the group consisting of hydrogen, $C_1$-$C_6$ alkyl group, —$OR^8$, —$SR^8$, —($NR^8R^9$), a CYCLIC SUBSTITUENT, TAIL, BRIDGE, -L-Rx and -L-Sc;

$R^5$ is independently selected from the group consisting of a $C_1$-$C_6$ alkyl group, a CYCLIC SUBSTITUENT, TAIL, BRIDGE, -L-Rx and -L-Sc; or $R^5$ is absent;

$R^{30}$, $R^{31}$, and $R^{32}$ are independently selected from the group consisting of hydrogen, $C_1$-$C_6$ alkyl, $C_3$-$C_{10}$ cycloalkyl, aryl, and heteroaryl, wherein n=0, 1 or 2;

wherein, BRIDGE, when present, is bound to a compound having formula I or another unsymmetrical cyanine dye.

Dyes that are useful for detecting poly(amino acids) are typically neutral in charge wherein $R^6$ is absent or $R^2$ is a $C_2$-$C_6$ sulfoalkyl group. Alternatively, charged dyes wherein X is O or S, n is 0 or 1, $R^6$ and $R^7$ form a fused aromatic ring —$R^{11}$=$R^{12}$—$R^{13}$=$R^{14}$— wherein $R^{11}$, $R^{12}$, $R^{13}$, and $R^{14}$ are independently selected from the group consisting of hydrogen, $C_1$-$C_6$ alkyl group, —$OR^8$; and $R^4$ and $R^5$ are independently a $C_1$-$C_8$ alkyl group or a CYCLIC SUBSTITUENT are also employed, and preferred, for the detection of poly(amino acids).

Dyes that are useful for nucleic acid detection preferably have the following properties wherein X is O, n is 0, $R^2$ is a methyl group, $R^6$ and $R^7$ form a fused aromatic ring —$R^{11}$=$R^{12}$—$R^{13}$=$R^{14}$— wherein $R^{11}$, $R^{12}$, $R^{13}$, and $R^{14}$ are independently selected from the group consisting of hydrogen, $C_1$-$C_6$ alkyl group, —$OR^8$, and $R^5$ and $R^4$ are independently a CYCLIC SUBSTITUENT that is an aryl group or an alkyl group.

In one aspect of the invention, that is preferred for detecting nucleic acids, the present dyes comprise at least one TAIL substituent that has the formula LINK-SPACER-CAP. LINK is single covalent bond, an either linkage (—O—), a thioether linkage (—S—) or an amine linkage (—$NR^{20}$—); where $R^{20}$ is hydrogen, $C_1$-$C_8$ alkyl or SPACER-CAP; SPACER is a covalent linkage; and, CAP is —O—$R^{21}$, —S—$R^{21}$, —$NR^{21}R^{22}$ or —$NR^{21}R^{22}R^{23}$; where $R^{21}$, $R^{22}$, and $R^{23}$ are independently selected from the group consisting of hydrogen, $C_1$-$C_8$ alkyl and a $C_1$-$C_8$ cycloalkyl wherein said alkyl or cycloalkyl are optionally substituted by one or more substituents selected from the group consisting of halogen, hydroxyl, $C_1$-$C_8$ alkoxy, amino, carboxy, sulfo and phenyl where said phenyl is optionally substituted by one or more substituents selected from the group consisting halogen, hydroxyl, $C_1$-$C_8$ alkoxy, amino, $C_1$-$C_8$ aminoalkyl, $C_1$-$C_8$ sulfoalkyl and $C_1$-$C_8$ carboxyalkyl; or one or more $R^{21}$, $R^{22}$, and $R^{23}$, taken in combination with $R^{20}$ and SPACER, or with SPACER alone, forms a 5- or 6-membered ring.

In this instance, $R^4$ or $R^5$ is independently a TAIL or a CYCLIC SUBSTITUENT substituted by TAIL. Thus, In one aspect of the invention, $R^4$ is a TAIL or a CYCLIC SUBSTITUENT substituted by TAIL and $R^5$ is an alkyl group wherein CAP is —$NR^{21}R^{22}$ where $R^{21}$ and $R^{22}$ are independently $C_1$-$C_6$ alkyl groups. Alternatively, CAP is —$NR^{21}R^{22}R^{23}$ where $R^{21}$, $R^{22}$ and $R^{23}$ are independently $C_1$-$C_6$ alkyl groups. In another aspect, $R^5$ is a CYCLIC SUBSTITUENT that is an aryl or heteroaryl and $R^4$ is a TAIL where CAP is —O—$R^{21}$, —S—$R^{21}$. In yet another aspect, $R^5$ is a TAIL, wherein CAP is -$NR^{21}R^{22}R^{23}$ where $R^{21}$, $R^{22}$ and $R^{23}$ are independently $C_1$-$C_6$ alkyl groups.

DETAILED DESCRIPTION OF THE INVENTION

I. Definitions

Figure 1:
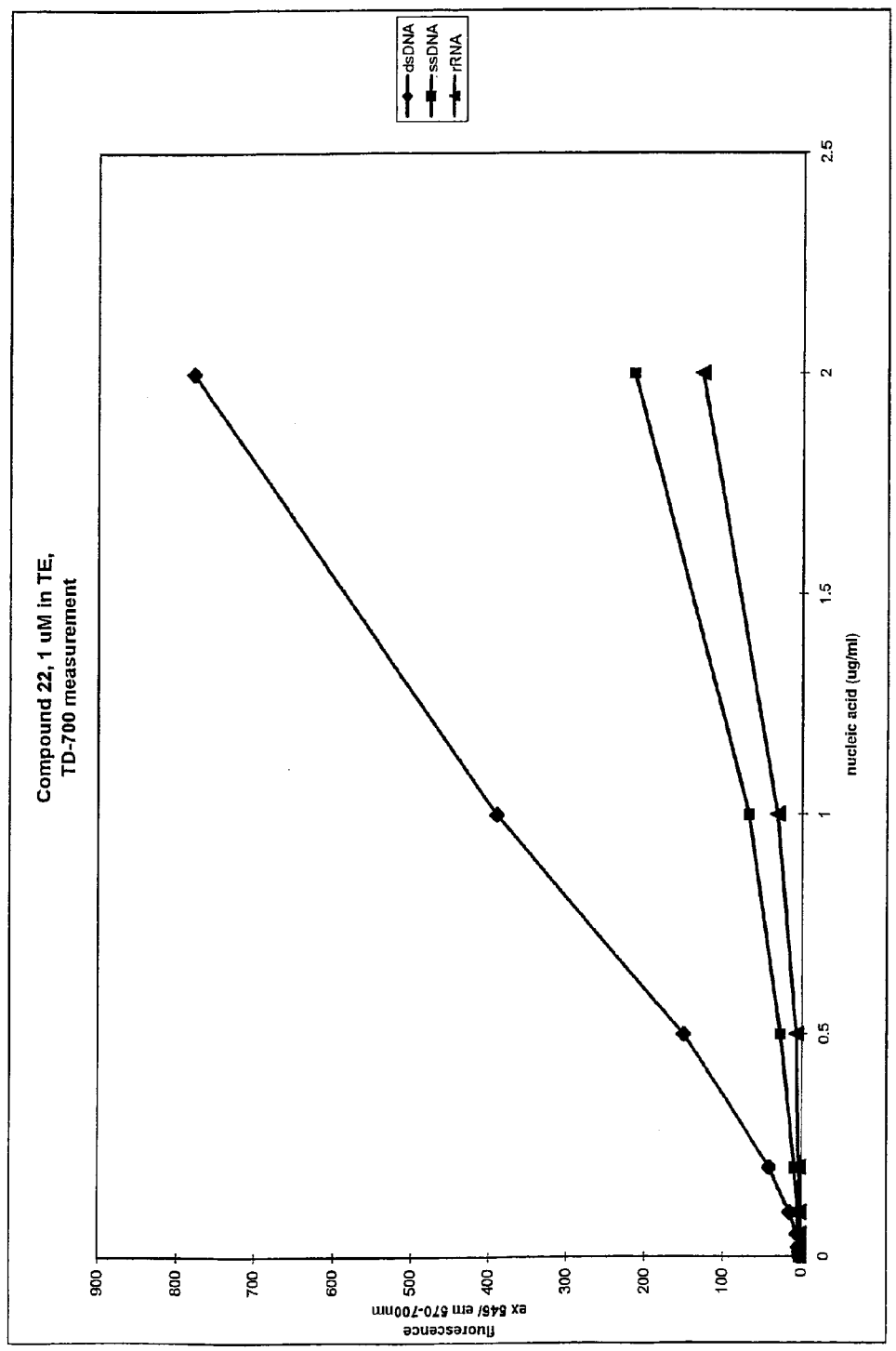
FIG. 1: Shows preferential fluorescent staining of double-stranded DNA by Compound 22 in the presence of single-stranded DNA and RNA, as described in Example 35.

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a fusion protein" includes a plurality of proteins and reference to "a fluorescent compound" includes a plurality of compounds and the like.

Unless defined otherwise, all technical and scientific terms used herein have the same meaning as commonly understood by one of ordinary skill in the art to which this invention is related. The following terms are defined for purposes of the invention as described herein.

The term "alkyl" as used herein refers to a straight, branched or cyclic hydrocarbon chain fragment containing between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment. Such substitutions include, but are not limited to: aryl; heteroaryl; halogen; alkoxy; amine (—NR'R"); carboxy and thio.

The term "amino" or "amine group" refers to the group —NR'R" (or N'RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The term "attachment site" as used herein refers to a site on a moiety or a molecule, e.g. a quencher, a fluorescent dye, an avidin, or an antibody, to which is covalently attached, or capable of being covalently attached, to a linker or another moiety.

The term "aqueous solution" as used herein refers to a solution that is predominantly water and retains the solution characteristics of water. Where the aqueous solution contains solvents in addition to water, water is typically the predominant solvent.

The term "—Sc" or "conjugated substance" as used herein refers to a biomolecule or non-biomolecule substance that contains or is modified to contain a reactive group wherein the reactive group will form a covalent bond with the present compounds that contain an appropriate reactive group. A molecule capable of being conjugated to the present compounds, conjugated substance, includes, but not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell or a virus.

The term "detectable response" as used herein refers to a change in or an occurrence of, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that is fluorescent upon binding or association with an analyte of interest, e.g. nucleic acid or poly(amino acid). These dyes include the present dyes and ones that can be employed as additional detection reagents. The additional detection reagents include fluorophores the are fluorogenic and ones that inherently fluorescent. Numerous fluorophores are known to those skilled in the art and include, but are not limited to, coumarin, acridine, furan, indole, borapolyazaindacene and xanthenes including fluoroscein, rhodamine, rhodol, cyanine, benzofuran, quinazolinone, and benzazole as well as other fluorophores described in RICHARD P. HAUGLAND, MOLECULAR PROBES HANDBOOK OF FLUORESCENT PROBES AND RESEARCH CHEMICALS ($9^{th}$ edition, CD-ROM, 2002).

The term "Linker", "L" or "BRIDGE" as used herein refers to a covalent linkage that is a single covalent bond or a series of stable covalent bonds incorporating 1-20 nonhydrogen atoms selected from the group consisting of C, N, O, S and P that covalently attach the present quenching compounds to another moiety such as a chemically reactive group or a conjugated substance including biological and non-biological substances. A "cleavable linker" is a linker that has one or more covalent bonds that may be broken by the result of a reaction or condition. For example, an ester in a molecule is a linker that may be cleaved by a reagent, e.g. sodium hydroxide, resulting in a carboxylate-containing fragment and a hydroxyl-containing product.

The term "poly(amino acids)" as used herein refers in a generic sense to proteins and polypeptides that include polymers of amino acid residues of any length. The term "peptide" is used herein to refer to polypeptides having less than 250 amino acid residues, typically less than 100 amino acid residues. The terms apply to amino acid polymers in which one or more amino acid residues are an artificial chemical analogue of a corresponding naturally occurring amino acid, as well as to naturally occurring amino acid polymers.

The term "Rx" or "reactive group" as used herein refers to a group that is capable of reacting with another chemical group to form a covalent bond, i.e. is covalently reactive under suitable reaction conditions, and generally represents a point of attachment for another substance. The reactive group is a moiety, such as malemide or succinimidyl ester, on the compounds of the present invention that is capable of chemically reacting with a functional group on a different compound to form a covalent linkage. Reactive groups generally include nucleophiles, electrophiles and photoactivatable groups.

The term "sample" as used herein refers to any material that may contain an analyte of interest, which typically includes poly(amino acids) and nucleic acids. Typically, the sample is a live cell, a biological fluid that comprises endogenous host cell proteins, nucleic acid polymers, nucleotides, oligonucleotides, peptides and buffer solutions. The sample may be in an aqueous solution, a viable cell culture or immobilized on a solid or semi solid surface such as a polymeric gel, membrane blot or on a microarray.

II. Compositions and Methods of Use

The invention comprises unsymmetrical cyanine dyes that incorporate an aza-benzazolium ring moiety. Included in the invention are monomeric and dimeric cyanine dyes, including those substituted by a cationic side chain, a chemically reactive functional group, and a conjugated substance. The dyes of the invention are virtually non-fluorescent when diluted in aqueous solution but when associated with nucleic acid polymers such as DNA or RNA, however, the resultant dye-nucleic acid complex is extremely fluorescent upon illumination. Similarly, when associated with lipid-complexed poly (amino acids), the resulting composition is extremely fluorescent upon illumination. The present dyes of the invention stain an analyte of interest, nucleic acids and poly(amino acida), in a wide variety of samples, particularly in aqueous solutions, electrophoretic gels, and a wide variety of cells, including microorganisms.

A. Aza-Benzazolium Containing Cyanine Dyes

The dyes of the invention comprise a cyanine dye that contains: 1) a first heterocyclic ring system that is a substituted aza-benzazolium ring, 2) a bridging methine and 3) a second heterocyclic ring system that is a pyridine, a quinoline, a pyridinium or a quinolinium. In one embodiment of the invention, the first or second ring system is substituted by a side chain, TAIL, that contains at least one heteroatom. In another embodiment, the first or second ring system is covalently bound to a second cyanine dye, forming a homo- or heterodimer. The first and second ring systems of the first or second cyanine dye is optionally further substituted by a variety of substituents, including chemically reactive groups as described below.

In one embodiment these dyes are pyridinium and quinolinium-based dyes, wherein the dye has the following formula:

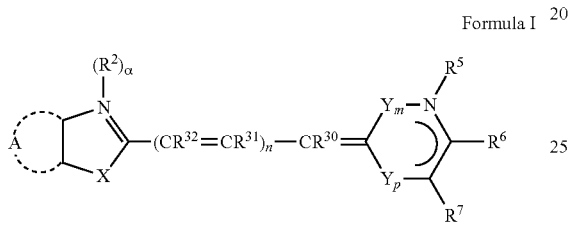

Formula I wherein A represents the atoms necessary to form one to two fused aromatic rings having 6 atoms in each ring, at least one of which is a nitrogen atom, said ring or rings being optionally further substituted one or more times by $C_1$-$C_{22}$ alkyl, $C_1$-$C_{22}$ alkoxy trifluoromethyl, halogen, BRIDGE, -L-Rx or -L-Sc;
  wherein Rx is a reactive group; Sc is a conjugated substance; and L and BRIDGE are independently a single covalent bond, or a covalent linkage;
X is O, S, Se, $NR^{15}$, or $CR^{16}R^{17}$, where $R^{15}$ is H or an alkyl group having 1-22 carbons; and $R^{16}$ and $R^{17}$, which may be the same or different, are independently alkyl groups having 1-22 carbons, or $R^{16}$ and $R^{17}$ taken in combination complete a five or six membered saturated ring;
$R^2$ is selected from the group consisting of -L-Rx, -L-Sc, TAIL, BRIDGE and an alkyl group having 1-22 carbons that is optionally substituted by sulfo, carboxy, amino, substituted amino or substituted ammonium, wherein $\alpha$ is 0 or 1; and TAIL is a heteroatom-containing moiety;
Y is —$CR^3$=$CR^4$— wherein p and m=0 or 1, such that p+m=1;
$R^3$, $R^4$, $R^6$, and $R^7$ are independently selected from the group consisting of hydrogen, a $C_1$-$C_{22}$ alkyl, a halogen, a CYCLIC SUBSTITUENT, —$OR^8$, —$SR^8$, —($NR^8R^9$), TAIL; BRIDGE, -L-Rx and -L-Sc; where $R^8$ and $R^9$ are independently a $C_1$-$C_6$ alkyl group, 1-2 alicyclic or aromatic rings; or $R^8$ and $R^9$ taken in combination are —($CH_2$)$_2$—V—($CH_2$)$_2$— where V is a single bond, —O—, —$CH_2$—, or —$NR^{10}$—, where $R^{10}$ is H or an alkyl having 1-6 carbons;
  wherein CYCLIC SUBSTITUENT is a substituted or unsubstituted aryl, heteroaryl or $C_3$-$C_{10}$ cycloalkyl;
or $R^6$ and $R^7$ form a fused aromatic ring —$R^{11}$=$R^{12}$—$R^{13}$=$R^{14}$— wherein $R^{11}$, $R^{12}$, $R^{13}$, and $R^{14}$ are independently selected from the group consisting of hydrogen, $C_1$-$C_{22}$ alkyl group, —$OR^8$, —$SR^8$, —($NR^8R^9$), a CYCLIC SUBSTITUENT, TAIL, BRIDGE, -L-Rx and -L-Sc;

$R^5$ is independently selected from the group consisting of a $C_1$-$C_{22}$ alkyl group, a CYCLIC SUBSTITUENT, TAIL, BRIDGE, -L-Rx and -L-Sc; or $R^5$ is absent;
$R^{30}$, $R^{31}$, and $R^{32}$ are independently selected from the group consisting of hydrogen, $C_1$-$C_{22}$ alkyl, $C_3$-$C_{10}$ cycloalkyl, aryl, and heteroaryl, wherein n=0, 1 or 2;
wherein, BRIDGE, when present, is bound to a compound having formula I or another unsymmetrical cyanine dye.

The A moiety represents the atoms necessary to form one or more fused 6-membered aromatic rings, incorporating at least one nitrogen atom =$N(R^2)_\beta$—. The six membered rings of the aza-benzazole ring system typically incorporate 1-3 nitrogen atoms, more preferably 1-2 nitrogen atoms. The nitrogen atoms are typically incorporated in the first 6-membered aromatic ring fused to the azole ring. Preferred embodiments of the aza-benzazole moiety include without limitation the following structures,

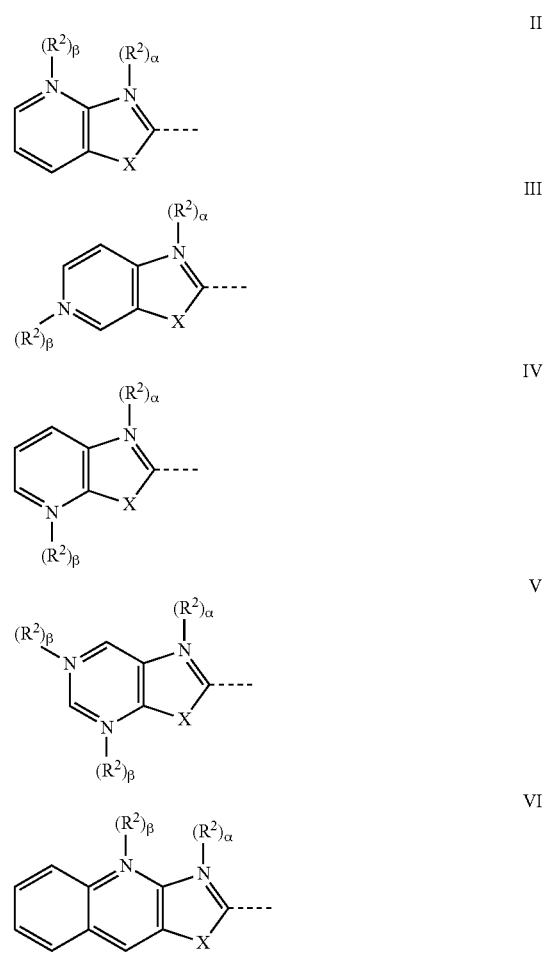

At least one of the aza-benzazole nitrogen atoms is quaternized by the substituent $R^2$, resulting in a formal positive charge. In one embodiment, $\alpha$=1 and $\beta$=0, such that the azole nitrogen atom is quaternized, and the benzo nitrogen atom is unsubstituted. In another embodiment, $\alpha$=0 and $\beta$=1, such that the azole nitrogen atom is unsubstituted and at least one benzo nitrogen atom is quaternized by $R^2$. Either $\alpha$ or a $\beta$ is 1, and typically no more than one $\beta$ in a given aza-benzazole is 1. The presence of an additional nitrogen atom incorporated in the fused aromatic ring of the benzazole moiety results in a shift of the emission spectra to longer wavelength. The presence of additional nitrogen atoms (as in structure V, above) shift the wavelength even further, as does the presence of additional fused 6-membered rings.

The aza-benzazole moiety is optionally further substituted at one or more aromatic carbons by an alkyl group having from 1-6 carbons, alkoxy having from 1-6 carbons, trifluoromethyl, halogen, BRIDGE, -L-Rx or -L-Sc. Although the carbon atoms of the aza-benzazolium ring system are typically fully substituted by hydrogen, incorporation of one or more non-hydrogen substituents can be used to fine tune the absorption and emission spectrum of the resulting dye. Typically, where present, there is only one non-hydrogen substituent on the aza-benzazole, preferably an alkoxy or halogen substituent.

$R_x$ is a reactive group that provides compounds of the present invention that can be covalently attached to another substance, a conjugated substance, such as a biomolecule or non-biomolecule including proteins and non-protein molecules such as dextran and a microparticle. The reactive group is typically a nucleophile, electrophile or photoactivatable group that chemically reacts with another appropriate reactive group on a biomolecule or non-biomolecule to form a covalent bond between the compounds of the present invention and another substance. Thus, a conjugated substance ($S_c$) can be any molecule with an appropriate reactive group, or is modified to contain an appropriate reactive group, that can be covalently bonded to the compounds of the present invention.

L is a covalent linkage that attaches the reactive group or conjugated substance to the present compounds wherein the covalent linkage may be a single covalent bond or a series of stable chemical bonds containing 1-20 nonhydrogen atoms. These atoms are selected from the group consisting of C, N, P, O or S. As used herein the term "BRIDGE" is also a covalent linkage having the same properties as L, but that attaches any one of the present dyes to another dye to form a homo- or hetero-dimer.

The substituent $R^2$ is an alkyl group having 1-22 carbons, that is linear or branched, saturated or unsaturated, that is optionally substituted one or more times by hydroxy, carboxy, sulfo, amino, amino substituted by 1-2 $C_1$-$C_6$ alkyls, or ammonium substituted by 1-3 $C_1$-$C_6$ alkyls. The $R^2$ substituent is alternatively a TAIL moiety, BRIDGE, a reactive group (-L-Rx) or a conjugated substance (-L-Sc). In one embodiment particularly suited for staining nucleic acids, $R^2$ is alkyl having 1-6 carbons, preferably methyl or ethyl, more preferably methyl. In another embodiment particularly suitable for staining lipid-complexed poly(amino acids), $R^2$ is a sulfoalkyl having 2-6 carbons.

As used herein the term "TAIL" refers to a heteroatom-containing side chain that is described by the formula LINK-SPACER-CAP. LINK is the linking moiety by which TAIL is attached to the dyes of the present invention. SPACER is a covalent linkage that connects LINK to CAP. CAP is the portion of TAIL that possesses a heteroatom component. Where the dye is substituted by a TAIL moiety, typically one or more of $R^2$, $R^3$, $R^4$, $R^5$, $R^6$, $R^7$, $R^{11}$, $R^{12}$, $R^{13}$ and $R^{14}$ is a TAIL. In one embodiment of the invention, at least one of $R^3$, $R^4$, $R^5$, $R^6$, $R^7$, $R^{11}$, $R^{12}$, $R^{13}$ and $R^{14}$ is required to be a TAIL. Preferably, $R^4$ or $R^5$ is a TAIL or a TAIL-substituted CYCLIC SUBSTITUENT. When $R^4$ is a TAIL, LINK is preferably —$NR^{20}$— or —S—. When TAIL is at any position other than $R^4$ or $R^5$, LINK is preferably —O— or a single bond.

As used herein the term "CYCLIC SUBSTITUENT" refers to a substituent that is a substituted or unsubstituted aryl, heteroaryl, or cycloalkyl having 3-10 carbons. As used herein, an aryl is a phenyl or a naphthyl group, and a heteroaryl substituent is a 5 or 6-membered heteroaromatic ring, wherein the heteroatom is O, N or S. The CYCLIC SUBSTITUENT is optionally substituted by halogen, amino, alkyl, perfluoroalkyl, alkylamino, dialkylamino, alkoxy or carboxyalkyl, wherein each alkyl group has 1-6 carbons, or by a TAIL moiety. The CYCLIC SUBSTITUENT is preferably a substituted or unsubstituted naphthyl, phenyl, thienyl, or cycloalkyl having 3-10 carbons, more preferably, the CYCLIC SUBSTITUENT is phenyl.

Where the dye is substituted by a CYCLIC SUBSTITUENT, typically one of $R^3$, $R^4$, $R^5$, $R^6$, $R^7$, $R^{11}$, $R^{12}$, $R^{13}$ and $R^{14}$ is a CYCLIC SUBSTITUENT. Preferably, one or more of $R^4$, $R^5$, $R^6$, or $R^{12}$ is TAIL or a CYCLIC SUBSTITUENT, including CYCLIC SUBSTITUENTS that are substituted by TAIL moieties.

In one embodiment, X is one of O, S, Se or $NR^{15}$, where $R^{15}$ is H or an alkyl group having 1-22 carbons, that is linear or branched, saturated or unsaturated, that is optionally substituted one or more times by hydroxy, carboxy, sulfo, amino, amino substituted by 1-2 $C_1$-$C_6$ alkyls, or ammonium substituted by 1-3 $C_1$-$C_6$ alkyls. The $R^{15}$ substituent is alternatively a TAIL moiety.

Alternatively, X is $CR^{16}R^{17}$, where $R^{16}$ and $R^{17}$, which may be the same or different, are independently H or alkyl groups having 1-22 carbons, that are linear or branched, saturated or unsaturated, that are optionally substituted one or more times by hydroxy, carboxy, sulfo, amino, amino substituted by 1-2 $C_1$-$C_6$ alkyls, or ammonium substituted by 1-3 $C_1$-$C_8$ alkyls. Alternatively, one of $R^{16}$ and $R^{17}$ is a TAIL moiety. Alternatively, the carbons of $R^{16}$ and $R^{17}$ taken in combination complete a five or six membered saturated ring. When X is $CR^{16}R^{17}$, $R^{16}$ and $R^{17}$ are typically alkyls having 1-6 carbons, preferably methyl or ethyl.

Preferably, X is O or S, more preferably X is S.

The two heterocyclic ring systems of the cyanine dye are linked by a bridging methine having the formula

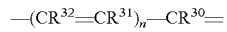

(where n=0, 1, or 2) in such a way as to permit extensive electronic delocalization. When n =0 the dyes are unsymmetrical monomethine dyes; when n=1 the dyes are trimethine dyes; when n=2, the dyes are pentamethine dyes. As with similar compounds, the number of methine groups between the heteroaromatic rings influences the spectral properties of the dye. The monomethine dyes of the present invention typically have yellow to orange to red fluorescence emission. The trimethine dye analogs are substantially shifted toward red wavelengths beyond 600 nm, and the pentamethine dyes are shifted even further, often exhibiting infrared fluorescence emission. Preferably n=0 or 1, more preferably n=0.

Methine substituents $R^{30}$, $R^{31}$, and $R^{32}$ are independently H, alkyl having 1-6 carbons, cycloalkyl having 3-10 carbons, aryl, or heteroaryl. Where n=1 or 2, each $R^{31}$ and $R^{32}$ varies independently. In one embodiment, only the substituent on the central carbon of the methine bridge is nonhydrogen ($R^{30}$ where n=0, $R^{31}$ where n=1, the centrally located $R^{32}$ where n=2). In another embodiment, where a methine substituent is nonhydrogen it is an alkyl. In another embodiment, where a methine substituent is nonhydrogen it is an aryl. Typically, each $R^{30}$, $R^{31}$, and $R^{32}$ is hydrogen. Where $R^{30}$, $R^{31}$, or $R^{32}$ is nonhydrogen, preferably n=1.

In one aspect of the invention, selected cyanine dyes having nonhydrogen methine substituents have particular utility as RNA selective nucleic acid stains. In another aspect of the invention, cyanine dyes having nonhydrogen methine substituents increase the signal-to-noise ratio when staining nucleic acids by decreasing background fluorescence.

The incorporation of substituted methine bridges, as described above, also provides useful derivatives of previously described cyanine dyes (e.g., U.S. Pat. No. 5,321,130 to Yue et al. (1994); U.S. Pat. No. 5,410,030 to Yue et al. (1995); U.S. Pat. No. 5,436,134 to Haugland et al. (1995); U.S. Pat. No. 5,582,977 to Yue et al. (1996); U.S. Pat. No. 5,658,751 to Yue et al. (1997); and U.S. Pat. No. 5,863,753 to Haugland et al. (1999)).

The second ring system contains a ring fragment Y that is $-CR^3=CR^4-$, with subscripts p and m equal to 0 or 1, such that p+m=1. The second ring system is a 6 membered heterocycle according to one of these formulations

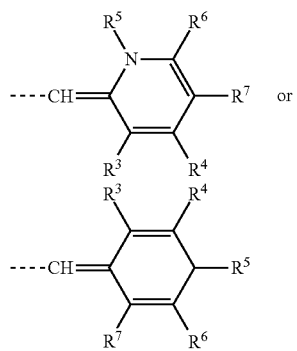

In preferred embodiments of the invention, m=1 and p=0 ("4-pyridiniums" and "4-quinoliniums").

The pyridinium and quinolinium-based cyanine dyes include an N-substituent $R^5$ that is an alkyl that is saturated or unsaturated, linear or branched, having 1-22 carbons, that is optionally substituted one or more times by hydroxy, carboxy, sulfo, amino, amino substituted by 1-2 $C_1$-$C_6$ alkyls, or ammonium substituted by 1-3 $C_1$-$C_6$ alkyls. Alternatively, $R^5$ is a CYCLIC SUBSTITUENT, a TAIL moiety, BRIDGE, a reactive group, a conjugated substance, a pair of electrons, or sulfoalkyl. Typically $R^5$ is an alkyl having 1-6 carbons, preferably 1-2 carbons, or $R^5$ is a CYCLIC SUBSTITUENT. In one embodiment, $R^5$ is a sulfoalkyl having 2-6 carbons. In another embodiment, $R^5$ is absent and replaced by a pair of electrons, resulting in a neutral unsymmetrical cyanine dye, as described below.

The substituents of the second ring system, $R^3$, $R^4$, $R^6$, and $R^7$, are independently H, halogen, an alkyl that is saturated or unsaturated, linear or branched, having 1-6 carbons, a CYCLIC SUBSTITUENT, a TAIL moiety, BRIDGE a reactive group (Rx) or a conjugated substance (Sc). $R^3$, $R^4$, $R^6$, and $R^7$ are optionally $-OR^8$, $-SR^8$, or $-(NR^8R^9)$ where $R^8$ and $R^9$, which can be the same or different, are independently alkyl groups having 1-6 carbons; or 1-2 alicyclic or aromatic rings; or $R^8$ and $R^9$ taken in combination form a cyclic structure having the formula $-(CH_2)_2-W-(CH_2)_2-$, where W is a single bond, $-O-$, $-CH_2-$, or $-NR^{10}-$, where $R^{10}$ is H or an alkyl having 1-6 carbons. In addition, $R^3$ and $R^4$ are optionally and independently $-OSO_2R^{19}$ where $R^{19}$ is alkyl having 1-6 carbons, or perfluoroalkyl having 1-6 carbons, or aryl.

Optionally, $R^6$ and $R^7$ taken in combination are $-(CH_2)_v-$ where v=3 or 4, forming a fused 5- or 6-membered ring, or $R^6$ and $R^7$, taken in combination form a fused 6-membered aromatic ring.

Alternatively, any of $R^3$, $R^4$, $R^6$ or $R^7$ is a CYCLIC SUBSTITUENT. Preferred ring substituents are independently H, alkyl, $-OR^8$, or a CYCLIC SUBSTITUENT, or a TAIL. In one aspect of the invention, $R^4$ is not hydrogen. In another aspect of the invention, $R^4$ is a CYCLIC SUBSTITUENT, a TAIL moiety, or a CYCLIC SUBSTITUENT that is further substituted by a TAIL moiety.

Where $R^6$ and $R^7$ taken in combination form a fused 6-membered aromatic ring, embodiments of this invention are quinolinium derivatives, and the second ring system has the formula

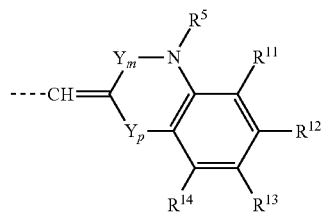

where ring substituents $R^{11}$, $R^{12}$, $R^{13}$, and $R^{14}$ are independently H, an alkyl that is saturated or unsaturated, linear or branched, having 1-6 carbons; halogen, $-OR^8$, $-SR^8$, $-(NR^8R^9)$, where $R^8$ and $R^9$ are as defined previously; or a CYCLIC SUBSTITUENT, a TAIL moiety, BRIDGE, a reactive group or a conjugated substance. Typically no more than one of $R^{11}$, $R^{12}$, $R^{13}$, and $R^{14}$ is nonhydrogen, and is preferably halogen or $-OR^8$. Preferred embodiments of the invention are quinoliniums wherein m=1 and p=0 ("4-quinoliniums"). The presence of the fused 6-membered ring at $R^6$ and $R^7$ typically increases the wavelength of the dye's fluorescence when associated with nucleic acids or lipid-complexed poly(amino acids).

In another embodiment of the invention, the dye of the invention is a homodimer or heterodimer of unsymmetrical cyanine dyes. That is, two cyanine dye subunits, at least one of which has a structure as described above, are joined by a covalent linkage, BRIDGE, to yield a dimeric compound having utility as a fluorescent stain for nucleic acids or lipid-complexed poly(amino acids) (see Compound 28, Example 12 and Compound 46, Example 13). While one cyanine dye subunit is an aza-benzazolium based cyanine dye subunit, the other portion of the dimeric dye may be a cyanine dye as described previously by Haugland and Yue (U.S. Pat. No. 5,321,130; U.S. Pat. No. 5,436,134; U.S. Pat. No. 5,658,751; and U.S. Pat. No. 5,869,689). Alternatively, the other portion of the dimeric dye is dissimilar in structure, for example a phenanthridium moiety.

The BRIDGE moiety is typically a combination of atoms having stable chemical bonds. The BRIDGE moiety optionally includes single, double, triple or aromatic carbon-carbon bonds, as well as carbon-nitrogen bonds, nitrogen-nitrogen bonds, carbon-oxygen bonds and carbon-sulfur bonds. The BRIDGE moiety typically includes ether, thioether, carboxamide, sulfonamide, urea, urethane or hydrazine moieties. Preferred BRIDGE moieties have 1-20 nonhydrogen atoms selected from the group consisting of C, N, O and S; and are composed of any combination of ether, thioether, amine, ester, carboxamide, sulfonamide, hydrazide bonds and aromatic or heteroaromatic bonds. Preferably BRIDGE is a combination of single carbon-carbon bonds and carboxamide or thioether bonds. Examples of BRIDGE include substituted or unsubstituted polymethylene, arylene, alkylarylene or arylenealkyl.

In a preferred embodiment, the BRIDGE moiety is an aliphatic chain containing a backbone of 4-19 carbon atoms. The carbon backbone may be interspersed at one or more intervals with a non-carbon heteroatom. The heteroatoms, which may be the same or different, are N, O, or S, preferably the heteroatom is N. Where the heteroatom is nitrogen, it is optionally substituted with one or more alkyl substituents having 1-6 carbon atoms, which may be the same or different. BRIDGE moieties that incorporate quaternary nitrogens confer cationic charges on the dimers of the invention, potentially increasing their affinity for nucleic acids, as well as decreasing their ability to permeate cell membranes.

Where the dimeric dye incorporates two cyanine subunits, the BRIDGE moiety is independently bound to each cyanine subunit at one of $R^2$, $R^3$, $R^4$, $R^5$, $R^6$, $R^7$, $R^{11}$, $R^{12}$, $R^{13}$, or $R^{14}$, as defined above. Preferably the BRIDGE moiety is independently bound to each cyanine subunit at $R^2$, $R^4$ or $R^5$, more preferably at $R^4$ or $R^5$.

By careful selection of the cyanine subunits that are covalently joined to form the dimeric dye, a variety of dimers with desirable spectral properties may be prepared. Selection of subunits that function as an energy donor and energy acceptor, respectively, via fluorescence resonance energy transfer typically produces a dimeric stain with an enhanced Stokes shift. The necessary difference in spectral properties for energy transfer to occur may be created by covalently attaching an aza-benzothiazole cyanine subunit to an aza-benzoxazole cyanine subunit. Alternatively, a monomethine cyanine subunit may be attached to a trimethine or pentamethine cyanine subunit, or a cationic cyanine subunit may be attached to a neutral cyanine dye subunit. In another aspect of the invention, an aza-benzoxazole cyanine subunit is attached to a non aza-substituted cyanine subunit. In yet another aspect of the invention, an aza-benzoxazole cyanine subunit is attached to a non-cyanine subunit, typically a phenanthridium subunit. Dimeric dyes incorporating non-aza-benzazolium containing cyanine subunits have previously been described (U.S. Pat. No. 5,582,977 to Yue et al. (1996); U.S. Pat. No. 5,401,847 to Glazer, (1995); U.S. Pat. No. 5,565,554 to Glazer (1996); and U.S. Pat. No. 5,760,201 to Glazer et. al. (1998)).

In a specific embodiment of the invention, the dyes of the invention are 4-pyridiniums or 4-quinoliniums, wherein $R^5$ is an alkyl having 1-6 carbons, or $R^5$ is a CYCLIC SUBSTITUENT, and $R^4$ is not hydrogen. Dyes having an $R^4$ substituent that is non-hydrogen typically possess enhanced quantum yields relative to similar dyes wherein $R^4$ is H. For this class of dyes, $R^5$ is preferably alkyl having 1-6 carbons. Preferably $R^4$ is a TAIL.

In an additional preferred embodiment of the invention, the second heterocyclic ring contains exactly two non-hydrogen substituents, one of which is a TAIL.

Some of the dyes of the present invention that possess a TAIL moiety at $R^4$ or $R^5$ exhibit particular utility for staining nucleic acids in cells and microorganisms. The utility of specific embodiments of the dyes of the present invention in staining cells and microorganisms is generally dependent on the chemical nature of the TAIL moiety, and the identity of the group present at $R^5$. For example, those compounds for which CAP is a quaternary ammonium salt are generally impermeant to living cells, with the exception of some yeast cells. However, the permeability of those compounds for which CAP is a primary or secondary amine, and LINK is a secondary or tertiary amine, is typically related to the nature of $R^5$ (the N-substituent).

Typically, dyes useful as impermeant cellular probes are those dyes having 2 or more positive charges overall, more preferably 3 or more positive charges. Preferred dyes for permeant cellular probes are dyes wherein $R^5$ is aryl or heteroaryl and CAP is —O—$R^{21}$ or —S—$R^{21}$, or dyes wherein $R^4$ is a CYCLIC SUBSTITUENT substituted by a cationic TAIL (for example, Compound 24, Example 10).

Dyes that are preferred for staining nucleic acids present in electrophoretic gels typically have a CAP that is a dialkylamino group, while dyes useful as stains for poly(amino acids) in electrophoretic gels are overall neutral in charge, typically by virtue of a sulfoalkyl group present at $R^2$ or $R^5$ that balances the cationic charge on the aza-benzazole moiety.

Any net positive or negative charges possessed by the dyes of the invention are balanced by a necessary counterion or counterions. Typically, the dyes of the invention are positively charged due to the presence of a quaternized aza-benzazole nitrogen, however the overall charge on the dye is determined by the charge present on each dye substituent (such as a negatively charged sulfonic acid group, or a positively charged ammonium group). Where necessary, the counterion is depicted as ψ and the polarity of the charge is indicated. Examples of useful counterions for dyes having a net positive charge include, but are not limited to, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred negative counterions are chloride, iodide, perchlorate and various sulfonates. Examples of useful counterions for dyes having a net negative charge include, but are not limited to, alkali metal ions, alkaline earth metal ions, transition metal ions, ammonium or substituted ammonium ions. Preferably, any necessary counterion is biologically compatible, is not toxic as used, and does not have a substantially deleterious effect on biomolecules.

In one embodiment, the cyanine dyes of the invention are substituted by at least one TAIL moiety having the formula LINK-SPACER-CAP.

LINK is a single covalent bond, an ether linkage (—O—), a thioether linkage (—S—), or an amine linkage (—$NR^{20}$—). In each embodiment, LINK forms the attachment between the cyanine dye core structure and SPACER. When LINK is an amine, the amine substituent ($R^{20}$) is optionally H, such that LINK=—NH—. Alternatively, $R^{20}$ is a linear or branched alkyl having 1-8 carbons. In another embodiment of the invention, $R^{20}$ is —SPACER'-CAP', yielding a TAIL having the formula

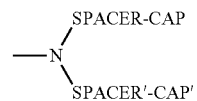

where SPACER' and CAP', respectively, may be the same as or different from SPACER and CAP, and are selected from the same alternatives defined for SPACER and CAP, respectively. For the sake of simplifying the description, SPACER and CAP are defined with the understanding that a description of SPACER includes SPACER', and a description of CAP includes CAP'.

SPACER is a covalent linkage that joins LINK and CAP. SPACER is a linear, branched, cyclic, heterocyclic, saturated or unsaturated arrangement of 1-16 C, N, P, O or S atoms. Alternatively, SPACER is a single covalent bond, such that both LINK and SPACER are not simultaneously single covalent bonds. Preferably, the SPACER linkage must begin and end with a carbon atom. Typically, if SPACER consists of a single atom, it is required to be a carbon atom, so that the first and last atom in SPACER (in this specific instance, they are the same atom) is a carbon. The 1-16 atoms making up SPACER are combined using any appropriate combination of ether, thioether, amine, ester, or amide bonds; or single, double, triple or aromatic carbon-carbon bonds; or phosphorus-oxygen bonds; or phosphorus-sulfur bonds; or nitrogen-nitrogen bonds; or nitrogen-oxygen bonds; or aromatic or heteroaromatic bonds. SPACER is further substituted by hydrogen to accommodate the valence state of each atom in SPACER.

Generally, the atoms of SPACER are arranged such that all heteroatoms in the linear backbone of SPACER are separated by at least one carbon atom, and preferably separated by at least two carbon atoms. Typically, SPACER is 1-6 carbon atoms in a linear or branched saturated chain. In one embodiment of the invention, SPACER incorporates a 6-membered aromatic ring (phenylene linkage). In another embodiment of the invention, SPACER incorporates a 5- or 6-membered heteroaromatic ring, wherein the heteroatoms are O, N, or S. Alternatively, SPACER incorporates amide linkages, ester linkages, simple ethers and thioethers, and amines in a linear arrangement, such as —$CH_2$—$CH_2$—(C=O)—NH—$CH_2$—$CH_2$—$CH_2$—. Preferably, SPACER is an alkylene (—$(CH_2)_k$—, where k=1-8).

LINK and SPACER, in combination, serve to attach a heteroatom-containing group, CAP, to the dye core structure. CAP may contain oxygen, sulfur or nitrogen, according to the formulas —O—$R^{21}$, —S—$R^{21}$, —$NR^{21}R^{22}$, or —$NR^{21}R^{22}R^{23}$. The substituents $R^{21}$, $R^{22}$, and $R^{23}$ are independently H, or a linear or branched alkyl or cycloalkyl having 1-8 carbons. Where any of $R^{21}$, $R^{22}$ and $R^{23}$ are alkyl or cycloalkyl, they are optionally further substituted by one or more halogen, hydroxy, alkoxy having 1-8 carbons, amino, carboxy, sulfo, or phenyl, where phenyl is optionally further substituted by halogen, hydroxy, alkoxy having 1-8 carbons, amino, aminoalkyl having 1-8 carbons, or sulfoalkyl or carboxyalkyl having 1-8 carbons. In another embodiment of the invention, one or more of $R^{21}$, $R^{22}$ and $R^{23}$, taken in combination with $R^{20}$ and SPACER, or with SPACER alone, forms a 5- or 6-membered ring that is aromatic, heteroaromatic, alicyctic or heteroalicyclic ring. When the 5- or 6-membered ring is heteroaromatic or heteroalicyclic, the ring contains 1-3 heteroatoms that are O, N or S. Preferably, $R^{21}$ and $R^{22}$ are independently hydrogen or alkyls having 1-8 carbons. $R^{23}$ is typically H or alkyl having 1-8 carbons.

When CAP is —$NR^{21}R^{22}R^{23}$, the CAP nitrogen atom is formally positively charged, and adds to the cumulative charge that is balanced by the presence of the counterion ψ.

Additionally, there are several embodiments of the present invention wherein CAP incorporates a cyclic structure. In these embodiments, CAP typically incorporates a 5- or 6-membered nitrogen-containing ring, optionally including an additional heteroatom (typically oxygen), where the ring nitrogen is optionally substituted by $R^{23}$ to give an ammonium salt. Specific versions of CAP include, but are not limited to, those listed in Table 1.

TABLE 1

Examples of specific CAP moieties

CAP is preferably —$NR^{21}R^{22}$ or —$NR^{21}R^{22}R^{23}$, where $R^{21}$, $R^{22}$, and $R^{23}$ are alkyls having 1-6 carbons. More preferably CAP is —$N(CH_3)_2$ or —$N(CH_3)_3$.

Preferably TAIL contains 6-10 non-hydrogen atoms, including LINK and CAP.

Selected examples of TAIL are listed in Table 2. For each TAIL, the identities of LINK, SPACER and CAP are specified. Where $R^{21}$, $R^{22}$, or $R^{23}$ combined with either $R^{20}$ or SPACER, the combination is indicated in the table.

TABLE 2

Specific examples of TAIL moieties

| TAIL | LINK | SPACER<br>SPACER' | CAP<br>CAP' |
|---|---|---|---|
|  | $CH_2CH_2CH_3$<br>----N | —$CH_2$—$CH_2$—$CH_2$— | —$N(CH_3)_2$ |

TABLE 2-continued

Specific examples of TAIL moieties

| TAIL | LINK | SPACER / SPACER' | CAP / CAP' |
|---|---|---|---|
| ----N(CH₂CH₂CH₃)-CH₂CH₂CH₂-N⁺(CH₃)₂-(propyl) (branched tertiary amine with pendant quaternary ammonium) | ----N(CH₃)(CH₂CH₂CH₃) | —CH₂—CH₂—CH₂— | —N⁺(CH₃)₃ |
| ----N[CH₂CH₂CH₂N(CH₃)₂]₂ (branched bis(dimethylaminopropyl)amine) | ----N(CH₃)-SPACER'-CAP' | —CH₂—CH₂—CH₂—<br>—CH₂—CH₂—CH₂— | —N(CH₃)₂<br>—N(CH₃)₂ |
| ----N[CH₂CH₂CH₂N⁺(CH₃)₃]₂ (branched bis(trimethylammoniopropyl)amine) | ----N(CH₃)-SPACER'-CAP' | —CH₂—CH₂—CH₂—<br>—CH₂—CH₂—CH₂— | —N⁺(CH₃)₃<br>—N⁺(CH₃)₃ |
| ----S—CH₂CH₂—N(CH₃)₂ | —S— | —CH₂—CH₂— | —N(CH₃)₂ |
| ----S—CH₂CH₂—N⁺(CH₃)₃ | —S— | —CH₂—CH₂— | —N⁺(CH₃)₃ |
| ----N(piperazinyl)N— (N-methylpiperazine) | —N(—R²²)— | —CH₂—CH₂— | —N(CH₃)(CH₂—CH₂—R²⁰) |
| ----N(piperazinyl)N⁺(CH₃)— (N-methyl, N'-quaternary piperazinium) | —N(—R²³)— | —CH₂—CH₂— | —N⁺(CH₃)₂(CH₂—CH₂—R²⁰) |
| ----S—C(=N—)(NH—) cyclic (2-mercapto-tetrahydropyrimidine) | —S— | —C(—R²²)=N—CH₂ CH₂ CH₂ | NH (-SPACER) |
| ----(p-phenylene)—CH₂—N⁺(CH₃)(CH₂CH₃)₂ | bond | (p-phenylene)-CH₂— | —N⁺(CH₃)(CH₂CH₃)₂ |
| ----O—CH₂CH₂CH₂—N(CH₃)₂ | —O— | —CH₂—CH₂—CH₂— | —N(CH₃)₂ |

TABLE 2-continued

Specific examples of TAIL moieties

| TAIL | LINK | SPACER SPACER' | CAP CAP' |
|---|---|---|---|
| 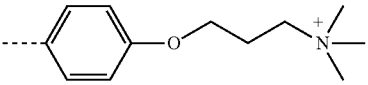 | bond | (p-phenylene)-<br>O—CH$_2$—CH$_2$—CH$_2$ | —N$^+$(CH$_3$)$_3$ |
| 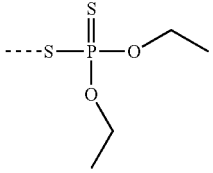 | —S— | 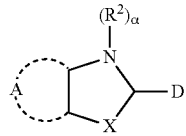 | —OCH$_2$CH$_3$ |
| ----NH—N(CH$_3$)$_2$ | —NH— | bond | —N(CH$_3$)$_2$ |
| 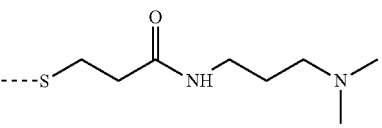 | —S— | —CH$_2$—CH$_2$—(C=O)<br>—NH—CH$_2$—CH$_2$—CH$_2$ | —N(CH$_3$)$_2$ |

In another embodiment of the invention, the cyanine dyes of the invention are described by the formula

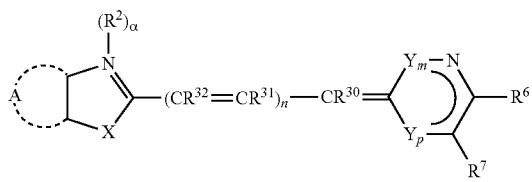

where A, X, R$^2$, α, n, Y$_m$, Y$_p$, R$^6$, R$^7$, R$^{30}$, R$^{31}$, R$^{32}$, and substitution patterns and preferences are as defined previously. These 'free base' versions of the cyanine dyes of the invention are not derivatized by an R$^5$ hydrogen or non-hydrogen atom containing substituent, instead a pair of electrons is present at the R$^5$ position, wherein the neural compound incorporates an aza-benzazole ring system, a methine moiety, and a pyridine or quinoline ring system. Related neutral cyanine dyes are described in U.S. Pat. No. 5,656,449 to Yue (1997).

B. Synthesis of the Present Dye Compounds

A useful synthetic route to the dyes of the present invention can be described in three parts, following the natural breakdown in the description of the compounds. In general, the synthesis of these dyes requires three precursors: the appropriate azabenzazolium, or polyazabenzazolium salt; the appropriate pyridine, quinoline, pyridinium or quinolinium; and (where n=1 or 2) a source for the methine spacer. Typically each component is selected so as to incorporate the appropriate chemical substituents, or functional groups that can be converted to the appropriate substituents. The chemistry that is required to prepare and combine these precursors so as to yield any of the subject derivatives is generally well understood by one skilled in the art (see U.S. Pat. No. 5,436,134 to Haugland et al. (1995); U.S. Pat. No. 5,656,449 to Yue (1997); U.S. Pat. No. 5,658,751 to Yue et al. (1997), U.S. Pat. No. 5,863,753 to Haugland et al. (1999)). Although there are many possible variations that may yield an equivalent result, we provide herein some useful general methods for their synthesis and incorporation of chemical modifications.

1. The Azabenzazollum or Polyazabenzazollum Moiety

A wide variety of derivatives suitable for the preparation of the dyes of the invention have been previously described (see, for example, Brooker, et al., J. AM. CHEM. SOC., 64, 199 (1942); Heravi, et al., INDIAN J. CHEM. 36B, 1025 (1997); Smith et al. SULFUR LETTERS 17, 197 (1994); Chu-Moyer et al. J. ORG. CHEM. 60, 5721 (1995); Turner, J. ORG. CHEM. 48, 3401 (1983); Couture et al. J. HETEROCYCLIC CHEM. 24, 1765 (1987); Petric et al. J. HETEROCYCLIC CHEM. 14, 1045, (1977); Barlin et al. AUST. J. CHEM., 37, 1729 (1984); Saikachi et al. CHEM. & PHARM. BULL. 9, 941 (1961); Barlin AUST. J. CHEM. 36, 983 (1983); Foye et al., J. PHARM. SCI. 64, 1371 (1975); Khanna et al. J. ORG. CHEM. 60, 960 (1995)); British Patent No. 870,753 to Ficken et al. (1961); Ficken at al., "Diazaindenes and Their Quaternary Salts-Part I" pp 3202-3212 (1959); Ficken at al., "Diazaindenes and Their Quaternary Salts-Part II" pp 584-588 (1961); These synthetic precursors have the common structure:

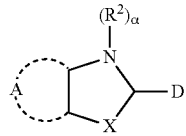

where A, X, R$^2$, and, α, have been defined previously. If X is O, the precursor compound is an aza- or polyaza-benzoxazolium; if X is S it is an aza- or polyaza-benzothiazolium; if X is Se it is an aza- or polyaza-benzoselenazollum; if X is N or an alkyl-substituted N it is an aza- or polyaza-benzimidazolium; and if X is CR$^{16}$R$^{17}$ then it is an aza- or polyaza-indolinium derivative. Commonly R$^{16}$ and R$^{17}$ are both methyl. However, methods for preparing compounds where R$^{16}$ and R$^{17}$ are not methyl are known (Smith at al., SULFUR LETTERS, 18, 79 (1995); Smith et al., CHEM INDUSTRY, 9, 302 (1988); Couture at al. HETEROCYCLES 22, 1383 (1984)).

The substituents on the aromatic carbons of the aza-benzazolium moiety are typically incorporated in the parent aza- or polyaza-benzazole molecule prior to quaternization with an alkylating agent. However, such substituents may also be incorporated during the synthesis of the aza-benzazole moiety (Examples 1-4). $R^2$ is usually obtained by alkylation of the parent heterocycle with an alkylating agent $R^2$—Z, where $R^2$ is a substituent as described above, in particular where $R^2$ is an alkyl group having 1-6 carbons, that is optionally substituted by sulfonate, carboxy, amino, or a chemically reactive group, or a precursor necessary for formation of a TAIL moiety, or attachment of a BRIDGE precursor, or second dimer subunit. Z of the alkylating agent is an electronegative group that frequently becomes the counterion on the resultant dye, ψ. The counterion may be exchanged for another counterion by methods known in the art, such as the use of ion exchange resins or by precipitation. Selected examples of $R^2$—Z include methyl iodide, diethyl sulfate, hexyl p-toluenesulfonate, sulfopropyl iodide, and sulfobutyliodide. Preferred $R^2$—Z are compounds that yield $R^2$=methyl, such as methyl iodide, methyl methanesulfonate, dimethyl sulfate, methyl trifluoromethanesulfonate or methyl p-toluenesulfonate.

D is a substituent whose nature is determined by the synthetic method utilized to couple the azabenzazolium or polyazabenzazolium precursor with the desired precursor of the second heterocyclic ring system. When n=0, D is typically alkylthio, commonly methylthio, or D is chloro, bromo or iodo. When n=1 or 2, D is methyl. Only in the case of D=methyl is any part of D incorporated in the final compound.

The aza-benzoxazolium precursor compounds wherein X=O have not been previously described.

The preparation of useful intermediates for the synthesis of the dyes of the invention via acetylation of a 2-amino-3-hydroxypyridine has similarly not been previously described (Examples 5 and 21).

2. The Second Heterocyclic Ring System that is a Pyridine, a Quinoline, a Pyridinium or a Quinolinium A variety of intermediate compounds useful as precursors for the second heterocyclic ring system can be used to synthesize the second heterocyclic ring system; many of which are available to one skilled in the art. Compounds containing the quinolinium moiety in this invention differ from those that contain a single pyridinium ring only in the presence of an additional aromatic ring containing four carbon atoms that is fused at the $R^6$ and $R^7$ positions of the parent structure. Except where reference is to a specific pyridine or pyridinium salt, it is understood that mention of pyridines or pyridinium salts encompasses benzopyridines and benzopyridinium salts, which are formally called quinolines or quinolinium salts. Mention of quinolines and quinolinium salts refer only to structures containing at least two fused aromatic rings. Similarly, pyridine and quinoline precursors are not formally charged, and are not substituted by an $R^5$ substituent.

In the synthesis of the dyes of the invention, the second heterocyclic precursor is usually appropriately substituted. Alternatively, substituents can be incorporated into the precursor structure subsequent to attachment of the azabenzazolium portion of the dye. One of the substituents that may be incorporated before or after reaction with the azabenzazolium or polyazabenzazolium precursor is TAIL.

There exist two major structural distinctions within the family of dyes described in the invention that are related to the point of attachment of the second heterocyclic ring system. In one case (where m=0 and p=1) the position of attachment places the methine moiety adjacent to the ring nitrogen ("2-substituted"). In the more common case (where m=1 and p=0) the position of the nitrogen atom is para to the point of attachment ("4-substituted").

Typically the required pyridinium salt precursor has the structure

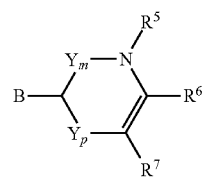

and the quinolinium salt precursor has the general structure

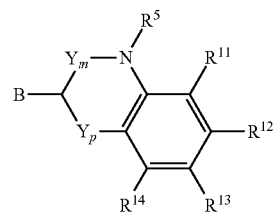

with the substituents as defined previously. At all times, the ring is a 6-membered pyridinium-based heterocycle.

When n=0, B is methyl, or B is chloro, bromo or iodo. When n=1 or 2, B is methyl. Only when n=1 or n=2 is any part of B incorporated in the final compound.

There are several general published methods for the synthesis of derivatives of pyridinium and pyridine, including those derivatives having substituents at any available position, including substitutions that are TAIL or that can be converted to TAIL before or after reaction with the azabenzazolium or polyazabenzazolium portion to form the dye core structure (see U.S. Pat. No. 5,436,134, U.S. Pat. No. 5,658,751, and U.S. Pat. No. 5,863,753). Typically, desired substituents are incorporated via alkylation of the nitrogen atom of an appropriately substituted quinoline, or $R^5$ substituents that are aryl or heteroaryl are incorporated by an Ullmann reaction of aniline or a substituted aniline or of a pyridone or quinolone derivative (pyridone and quinolone precursors may also be prepared by an Ullmann reaction of the appropriately substituted precursor if the nitrogen atom is hydrogen-substituted).

Pyridone and quinolone intermediates containing a non-hydrogen group at $R^5$ are particularly important precursors to a wide variety of other pyridinium and quinolinium salts that are substituted at $R^4$. In particular a salt is formed by treatment of the appropriate pyridone or quinolone with a strong chlorinating agent such as $PCl_5$, $POCl_3$ or $SOCl_2$, for instance in the reaction below. Similarly, a sulfonate can be substituted at $R^4$ by treating the pyridone or quinolone with the appropriate sulfonic acid anhydride.

The reactivity of the 2-halogenated pyridinium or quinolinium intermediate offers a variety of synthetic methods for attachment of various substituents at the 2-position, including TAIL moieties, TAIL precursors, -L-$R_x$ moieties, and BRIDGE precursors. However, the reactivity of the 2-halo derivatives is preserved even after conjugation with the benzazolium precursor, enabling conversion of the resulting dye in which $R^4$ is halogen into the appropriate alkoxy, amino and thiolate analogs, as described for the pyridinium and quinolinium precursors. Of particular utility for the dyes of the present invention is the displacement of a 2-chloro substituent by amines.

Additionally, the 2-oxo group of pyridone or quinolone precursors can be chemically reduced to derivatives in which $R^4$ is H using a variety of reagents including DIBAL-H (diisobutylaluminum hydride).

3. Th M Thine Moiety

The specific synthetic reagents used in the synthesis of the present dyes determine the number of methine groups that connect the two heterocyclic ring systems. When n=0, the synthesis of monomethine dyes commonly uses a combination of reagents where the methine carbon atom results from either D on the azabenzazolium or polyazabenzazolium salt or B on the pyridinium salt being methyl and the other of D or B being a reactive "leaving group" that is typically methylthio or chloro, but that can be any leaving group that provides sufficient reactivity to complete the reaction, as described by Brooker et al., supra. Whether D or B is methyl depends primarily on the relative ease of synthesis of the requisite precursor salts. Because 2-methyl and 4-methyl pyridines are usually easier to prepare than their corresponding methylthio analogs, monomethine dyes are typically prepared from precursors in which D=methylthio and B=methyl. The condensing reagent in the case of monomethine dyes is typically a weak base such as triethylamine or diisopropylethylamine.

To synthesize trimethine dyes (n=1) both D and B are methyl. In this case the additional methine carbon is provided by a reagent such as diphenylformamidine, N-methylformanilide or ethyl orthoformate. Because under certain reaction conditions these same reagents can yield symmetrical cyanine dyes that incorporate two moles of a single quaternary salt, it is important to use the proper synthetic conditions, and a suitable ratio of the carbon-providing reactant to the first quaternary salt, so that the proper intermediate will be formed. This intermediate is treated either before or after purification with the second quaternary salt to form the asymmetric cyanine dye. If desired, the counterion ψ can be exchanged at this point. One can react either of the heteroaromatic precursor salts with the carbon-providing reagent to form the required intermediate, or form the intermediate from the more readily available 2-methylazobenzazolium or 2-methylpolyazabenzazolium salts similar to the method described by Brooker et al but modified by use of an azabenzazolium or polyazabenzazolium salt.

Synthesis of the pentamethine dyes (n=2) raises the same synthetic concerns about controlling the formation of an asymmetric intermediate. The three-carbon fragment that is required for the additional atoms in the methine moiety comes from a suitable precursor to malonaldehyde such as malonaldehyde dianil, 1,1,3,3-tetramethoxypropane, 1,1,3-trimethoxypropene, 3-(N-methylanilino)propenal or other reagents. The condensing agent for this reaction is usually 1-anilino-3-phenylimino-1-propene (U.S. Pat. No. 2,269,234 to Sprague, 1942), which generates the 2-(2-anilinovinyl)-3-methylbenzazolium tosylate intermediate.

The introduction of desired methine substituents ($R^{30}$, $R^{31}$, and/or $R^{32}$) is typically accomplished by modification of either the azabenzazolium moiety or the quinolinium/pyridinium moiety prior to condensation of the desired dye (Examples 28-31). Typically $R^{32}$ is introduced by incorporation into the azabenzazolium moiety (Example 29), while $R^{30}$ is introduced on the quinolinium/pyridinium moiety (Example 28). $R^{31}$ may be introduced on either heterocyclic ring system, depending on the simplicity and accessibility of the resulting synthesis.

Those dyes having a quinoline or pyridine ring rather than a quinolinium or pyridinium are typically prepared by either heating a azabenzazolium or polyazabenzazolium salt that contains a good leaving group (chloride, methylthio, etc.) at the 2-position, with a 2- or 4-methyl substituted or unsubstituted quinoline or pyridine in the presence of acetic anhydride as an activator.

Alternatively, a corresponding N-methylquinolinium cyanine dye is dealkylated (typically demethylated) using a good nucleophile, such as an alkali metal salt of a thiol (e.g. sodium thiophenoxide) in a polar solvent (e.g. DMF, DMSO). Where $R^2$ is ethyl (or a higher alkyl), the N-methyl substituent on the pyridinium or quinolinium ring is removed selectively during dealkylation. Where the $R^2$ substituent is also methyl, two demethylated products may result, but the two products are readily separated by column chromatography. Where the N-substituent is a substituted alkyl, such as 2-methoxyethoxymethyl, other reagents, such as a strong acid, are used to generate the corresponding pyridine or quinoline end product.

4. TAIL

As described above, TAIL is composed of three parts: LINK, SPACER and CAP. The chemical composition of SPACER is determined by the chemistry required to attach the heteroatom in CAP with the dye core structure via LINK.

As described above, those dyes of the present invention that are 4-substituted heterocycles wherein $R^4$ is a TAIL are most conveniently synthesized from the 2-halo substituted precursor either before or after condensation with the azabenzazolium or polkyazabenzazolium portion of the dye by a nucleophilic displacement reaction of the halogen by a thiol, alkoxide, or a primary or secondary amine.

CAP may be incorporated directly into TAIL before or after condensation of the second heterocyclic ring with the azabenzazolium or polyazabenzazolium salt, or CAP may be added or further modified at a later stage in the synthesis. For instance, when CAP is a cyclic or non-cyclic primary, secondary or tertiary amine, CAP can be alkylated to a quaternary ammonium (Examples 10, 11). This reaction can be used to increase the polarity of the dye and to thus restrict its penetration through the membrane of living cells, and to additionally increase the dye's affinity for nucleic acids.

Precursors to TAIL include, among other functional groups, carboxylic acids, halides, alcohols and thiols. Each of these reactive groups can be used to attach a heteroatom-containing moiety (i.e., CAP) to the dye's core structure, generally through the formation of amides, ethers or thioethers, which are incorporated into SPACER before or after attachment of SPACER to the dye's core structure.

5. Homo- and Heterodimer Dyes

The dimeric dyes of the invention that are homodimers are typically prepared by condensation of two equivalents of a chemically reactive cyanine dye with one equivalent of a BRIDGE precursor, by methods known in the art (Example 12, 13). Heterodimeric dyes are prepared similarly, but the synthesis typically requires multiple steps in order to achieve the desired final product (as described in U.S. Pat. No. 5,321,130; U.S. Pat. No. 5,436,134; U.S. Pat. No. 5,658,751; U.S. Pat. No. 5,869,689, U.S. Pat. No. 5,582,977; U.S. Pat. No. 5,401,847; U.S. Pat. No. 5,565,554; and U.S. Pat. No. 5,760,201).

C. Reactive Cyanine Dyes and Dye-Conjugates

In another embodiment of the invention, the cyanine dyes of the invention are chemically reactive, and are substituted by at least one group -L-$R_x$, where $R_x$ is the reactive group that is attached to the dye by a covalent linkage L. $R_x$ is a reactive group that functions as the site of attachment for another moiety wherein the reactive group chemically reacts with an appropriate reactive or functional group on another substance or moiety. These reactive groups or reactive precursor are synthesized during the formation of the present compounds providing present cyanine compounds that can be covalently attached to another substance, conjugated substance, facilitated by the reactive group. In this way, compounds incorporating a reactive group ($R_x$) can be covalently attached to a wide variety of biomolecules or non-biomolecules that contain or are modified to contain functional groups with suitable reactivity, resulting in chemical attachment of the conjugated substance ($S_C$), represented by -L-$S_C$. This conjugation typically confers the nucleic acid- and/or poly(amino acid)-sensing abilities of the cyanine dye on the conjugated substance. However, the present dye compounds can also function as reporter molecules for the conjugated substance wherein the sensing ability of the compounds is not employed. The reactive group and functional group are typically an electrophile and a nucleophile that can generate a covalent linkage. Alternatively, the reactive group is a photoactivatable group, and becomes chemically reactive only after illumination with light of an appropriate wavelength. Typically, the conjugation reaction between the reactive group and the substance to be conjugated results in one or more atoms of the reactive group $R_x$ to be incorporated into a new linkage attaching the compound of the invention to the conjugated substance Sc. Selected examples of functional groups and linkages are shown in Table 3, where the reaction of an electrophilic group and a nucleophilic group yields a covalent linkage.

TABLE 3

Examples of some routes to useful covalent linkages with electrophile and nucleophile reactive groups

| Electrophilic Group | Nucleophilic Group | Resulting Covalent Linkage |
|---|---|---|
| activated esters* | amines/anilines | carboxamides |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | mines | ryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |

TABLE 3-continued

Examples of some routes to useful covalent linkages with electrophile and nucleophile reactive groups

| Electrophilic Group | Nucleophilic Group | Resulting Covalent Linkage |
|---|---|---|
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. oxysuccinimidyl (—$OC_4H_4O_2$) oxysulfosuccinimidyl (—$OC_4H_3O_2$—$SO_3H$), -1-oxybenzotriazolyl (—$OC_6H_4N_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —$OCOR^a$ or —$OCNR^aNHR^b$, where $R^a$ and $R^b$, which may be the same or different, are $C_1$-$C_6$ alkyl, $C_1$-$C_6$ perfluoroalkyl, or $C_1$-$C_6$ alkoxy; or cyclohexyl, 3-dimethylaminopropyl, or N-morpholinoethyl).
**Acyl azides can also rearrange to isocyanates The cyanine compounds of the present invention typically comprise a linker when the dye compound is substituted with a reactive group or a conjugated substance wherein the linker is used to covalently attach a conjugated substance or reactive group to the compound. When present, the linker is a single covalent bond or a series of stable bonds. Thus, the conjugated substance or reactive group may be directly attached (where Linker is a single bond) to the cyanine compounds or attached through a series of stable bonds. When the linker is a series of stable covalent bonds the linker typically incorporates 1-20 nonhydrogen atoms selected from the group consisting of C, N, O, S and P. In addition, the covalent linkage can incorporate a platinum atom, such as described in U.S. Pat. No. 5,714,327. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a single covalent bond or a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoky, cycloalkyl and amine moieties. The longest linear segment of the linkage L preferably contains 4-10 nonhydrogen atoms including one or two heteroatoms. Examples of L include substituted or unsubstituted polymethylene, arylene, alkylarylene or arylenealkyl. In one embodiment, L contains 1-6 carbon atoms; in another, L is a thioether linkage. In yet another embodiment, L has the formula —$(CH_2)_a(CONH(CH_2)_b)_z$—, where a is an integer from 0-5, b is an integer from 1-5 and z is 0 or 1.

Any combination of linkers may be used to attach the Rx or Sc and the cyanine compounds together, typically a compound of the present invention when attached to more than one Rx or Sc will have one or two linkers attached that may be the same or different, The linker may also be substituted to alter the physical properties of the carbocyanine compounds, such as solubility and spectral properties of the compound.

The -L-Rx moiety, or precursor to the -L-Rx moiety, is synthesized on the appropriate precursor during the synthesis of the cyanine dye compound. The, -L-$R_x$ moieties are typically prepared from 2-halo substituted heterocyclic precursors, either before or after condensation with the azabenzazolium or polyazabenzazolium portion of the dye by a nucleophilic displacement reaction of the halogen by a thiol, alkoxide, or a primary or secondary amine, which is then incorporated into the covalent linkage L.

The -L-$R_x$ group can be bound to the dye at $R^2$, $R^3$, $R^4$, $R^5$, $R^6$, $R^7$, $R^{11}$, $R^{12}$, $R^{13}$, or $R^{14}$. Alternatively, the -L-$R_x$ moiety is bound to one of the aromatic carbons of the aza-benzazole ring system. Typically, -L-$R_x$ is bound to the dye at $R^2$, $R^4$ or $R^5$. Preferably -L-$R_x$ is bound to the dye at $R^4$ or $R^5$.

The selection of covalent linkage to attach the dye to the conjugated substance typically depends on the chemically reactive functional group on the substance to be conjugated. The types of functional groups typically present on the organic or inorganic substances include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the substance (typical for polysaccharides), or a variety of sites may occur (e.g. amines, thiols, alcohols, phenols), as is typical for proteins. A conjugated substance may be conjugated to more than one dye, which may be the same or different, or to a substance that is additionally modified by a hapten. Although some selectivity can be obtained by careful control of the reaction conditions, selectivity of labeling is best obtained by selection of an appropriate reactive dye.

Typically, $R_x$ will react with an amine, a thiol or an alcohol. In one embodiment, $R_x$ is an acrylamide, an activated ester of a carboxylic acid, an acyl azide, an acyl nitrile, an aldehyde, an alkyl halide, an amine, an anhydride, an aniline, an aryl halide, an azide, an aziridine, a boronate, a carboxylic acid, a diazoalkane, a haloacetamide, a halotriazine, a hydrazine, an imido ester, an isocyanate, an isothiocyanate, a maleimide, a phosphoramidite, a sulfonyl halide, or a thiol group. Preferably, $R_x$ is a carboxylic acid, a succinimidyl ester, an amine, a haloacetamide, an alkyl halide, a sulfonyl halide, an isothiocyanate, a maleimide group or an azidoperfluorobenzamido group.

Prior to use in preparation of conjugates to form -L-Sc moieties, chemically reactive forms of the dyes of the invention are typically dissolved in water or a water-miscible such as a lower alcohol, dimethylformamide (DMF), dimethylsulfoxide (DMSO), acetone, acetonitrile, tetrahydrofuran (THF), dioxane or acetonitrile. The preparation of dye conjugates using reactive dyes is well documented, Haugland, MOLECULAR PROBES, INC. HANDBOOK OF FLUORESCENT PROBES AND RESEARCH CHEMICALS, 1996 and Brinkley, BIOCONJUGATE CHEM., 3, 2 (1992). Conjugates typically result from mixing appropriate reactive cyanine dyes and the substance to be conjugated. In a suitable solvent in which both are soluble, using methods well known in the art, followed by separation of the conjugate from any unreacted dye and by-products. These dyes are typically combined with the sample under conditions of concentration, stoichiometry, pH, temperature and other factors that affect chemical reactions that are determined by both the reactive functional groups on the dye and the expected site of modification on the molecule to be modified. These factors are generally well known in the art of forming bioconjugates (Haugland et al. "Coupling of Antibodies with Biotin" THE PROTEIN PROTOCOLS HANDBOOK, J. M. Walker, ed., Humana Press, (1996); Haugland "Coupling of Monoclonal Antibodies with Fluorophores" METHODS IN MOLECULAR BIOLOGY, VOL. 45: MONOCLONAL ANTIBODY PROTOCOLS, W. C. Davis, Ed. (1995)). For those reactive dyes that are photoactivated, conjugation requires illumination of the reaction mixture to activate the reactive dye. The dye-conjugate is used in solution or lyophilized and stored for later use.

A variety of dye-conjugates may be prepared using the reactive dyes of the invention, including present dye conjugates of antigens, steroids, vitamins, drugs, haptens, metabolites, toxins, environmental pollutants, amino acids, peptides, proteins, nucleic acids, nucleic acid polymers, carbohydrates, lipids, and polymers. In another embodiment, the conjugated substance is an amino acid, peptide, protein, polysaccharide, nucleotide, oligonucleotide, nucleic acid, hapten, drug, lipid, phospholipid, lipoprotein, lipopolysaccharide, liposome, lipophilic polymer, polymer, polymeric microparticle, biological cell or virus. In one aspect of the invention, the conjugated substance is labeled with a plurality of dyes of the present invention, which may be the same or different.

Typically, the conjugated substance ($S_C$) is an amino acid, a peptide, a protein, a polysaccharide, a nucleotide, an oligonucleotide, a nucleic acid, a lipid, a polymeric microparticle, a biological cell, or a virus. The most preferred conjugated substances are conjugates of haptens, nucleotides, oligonucleotides, nucleic acid polymers, proteins, or polysaccharides. Most preferably, the conjugated substance is a nucleic acid, or a substance that interacts in a specific fashion with nucleic acids, such as DNA-binding proteins.

In one embodiment, the conjugated substance ($S_c$) is an amino acid (including those that are protected or are substituted by phosphates, carbohydrates, or $C_1$ to $C_{22}$ carboxylic acids), or is a polymer of amino acids such as a peptide or protein. Preferred conjugates of peptides contain at least five amino acids, more preferably 5 to 36 amino acids. Preferred peptides include, but are not limited to, neuropeptides, cytokines, toxins, protease substrates, and protein kinase substrates. Also preferred are peptides that serve as organelle localization peptides, that is, peptides that serve to target the conjugated dye for localization within a particular cellular substructure by cellular transport mechanisms. Preferred protein conjugates include enzymes, antibodies, tectins, glycoproteins, histones, albumins, lipoproteins, avidin, streptavidin, protein A, protein G, phycobiliproteins and other fluorescent proteins, hormones, toxins and growth factors. Typically, the conjugated protein is an antibody, an antibody fragment, avidin, streptavidin, a toxin, a lectin, or a growth factor. Preferred haptens include biotin, digoxigenin and fluorophores.

In another embodiment, the conjugated substance ($S_c$) is a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. Preferably, the conjugated nucleotide is a nucleoside triphosphate or a deoxynucleoside triphosphate or a dideoxynucleoside triphosphate.

Preferred nucleic acid polymer conjugates are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides. The dye is optionally attached via one or more purine or pyrimidine bases through an amide, ester, ether or thioether bond; or is attached to the phosphate or carbohydrate by a bond that is an ester, thioester, amide, ether or thioether. Alternatively, the dye is attached by formation of a non-covalent association of the nucleic acid and a photoreactive dye of the invention, followed by illumination, resulting in covalently bound dye. Nucleotide conjugates of the invention can be incorporated by some DNA polymerases and can be used for in situ hybridization and nucleic acid sequencing (e.g., U.S. Pat. Nos. 5,332,666; 5,171,534; and 4,997,928, all incorporated by reference; and WO Appl. 94/05688).

In another embodiment, the conjugated substance ($S_c$) is a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). Preferred polysaccharide conjugates are dextran or FICOLL conjugates.

In another embodiment, the conjugated substance ($S_c$), is a lipid (typically having 6-25 carbons), including glycolipids, phospholipids, and sphingolipids. Alternatively, the conjugated substance is a lipid vesicle, such as a liposome, or is a lipoprotein (see below). Some lipophilic substituents are useful for facilitating transport of the conjugated dye into cells or cellular organelles.

Furthermore, the conjugates are optionally dye-conjugates of polymers, polymeric particles, polymeric microparticles including magnetic and non-magnetic microspheres, polymeric membranes, conducting and non-conducting metals and non-metals, and glass and plastic surfaces and particles. Conjugates are typically prepared by chemical modification of a polymer that contains functional groups with suitable chemical reactivity. The conjugated polymer may be organic or inorganic, natural or synthetic. In a preferred embodiment, the dye is conjugated to a polymer matrix, such as a polymeric particle or membrane, including membranes suitable for blot assays for nucleic acids or proteins. In another embodiment, the conjugated substance is a glass or silica, which may be formed into an optical fiber or other structure. In another embodiment, the conjugated polymer is poly(ethylene glycol), a poly(acrylate) or a poly(acrylamide).

In one embodiment, the conjugated substance is a specific binding pair members wherein the dye is conjugated to a specific binding pair member and used to detect nucleic acids or poly(amino acids). Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. In this instance, the dye compounds of the present invention function as a reporter molecule for the specific binding pair and not a dye selective for poly(amino acids) or nucleic acids.

TABLE 4

Representative Specific Binding Pairs

| antigen | antibody |
| --- | --- |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |

TABLE 4-continued

Representative Specific Binding Pairs

| antigen | antibody |
| --- | --- |
| hormone | hormone receptor |
| ion | chelator |

*IgG is an immunoglobulin
†cDNA and cRNA are the complementary strands used for hybridization D. Methods of Use The use of the invention comprises combining a dye (monomer or dimer) or dye-conjugate of the present invention with a sample that contains or is thought to contain the desired analyte, incubating the mixture of dye and sample for a time sufficient for the dye to combine with the analyte in the sample and to form one or more dye-analyte complexes having a detectable fluorescent signal. The characteristics of the dye-analyte complex. Including the presence, location, intensity, excitation and emission spectra, fluorescence polarization, fluorescence lifetime, photobleaching rate and other physical properties of the fluorescent signal can be used to detect, differentiate, sort, quantitate, and/or analyze aspects or portions of the sample. The dyes of the invention are optionally used in conjunction with one or more additional detection reagents (preferably detectably different fluorescent reagents), including dyes of the same class having different spectral properties.

Therefore, a method for determining the presence of an analyte of interest in a sample, comprises the steps of:
 a) combining said sample with a staining solution, wherein said staining solution comprises one or more dyes of the present invention;
 b) incubating said sample and said staining solution for a sufficient amount of time to form a dye-analyte complex;
 c) illuminating said complex with an appropriate wavelength whereby the presence of said analyte is determined.

Typically the analyte of interest is a nucleic acid polymer or a lipid-complexed poly(amino acid). However when a dye-conjugate is present in the staining solution the analyte may be any compound the conjugated substance has an affinity for. Thus, in one embodiment of the invention, the analyte is a nucleic acid polymer, such as DNA or RNA. In another embodiment of the invention, the analyte is a lipid-complexed poly(amino acid). By poly(amino acid) is meant any polymer of amino acid subunits, artificial or natural, such as peptides and proteins, and including glycoproteins, lipoproteins and other modified proteins.

The staining solution is preferably an aqueous or aqueous miscible solution that is compatible with the sample and the intended use. For biological samples, where minimal perturbation of cell morphology or physiology is desired, the staining solution is selected accordingly. For solution assays, the staining solution preferably does not perturb the native conformation of the analyte undergoing evaluation.

The dyes have greater stability in buffered solutions than in water alone; and agents that reduce the levels of free oxygen radicals, such as β-mercaptoethanol, contribute to the stability of the dyes. When staining nucleic acids, high concentrations of organic solvents, cations, and oxidizing agents generally reduce fluorescence of the dye-nucleic acid complex, as does the ionic detergent sodium dodecyl sulfate (SDS) at concentrations >0.01%. A number of staining solution additives, however, do not interfere with the fluorescence of the dye-nucleic acid complex (e.g. urea up to 8 M; CsCl up to 1 g/mL; formamide up to 50% of the solution; and sucrose up to 40%). Nonionic detergents such as Tween 20, NP40 or Triton X-100 at concentration of less than or equal to 0.1%, DMSO at concentrations less than or equal to 10%, and ethanol at concentrations of less than or equal to about 10% stabilize the dye-buffer staining solution, but can interfere with staining of poly(amino acids).

Although typically used in an aqueous or aqueous miscible solution, the staining solution is typically prepared by first dissolving the dye in a water-miscible organic solvent such as dimethylsulfoxide (DMSO), dimethylformamide (DMF), or a lower alcohol, such as methanol or ethanol. This stock solution is typically prepared at a concentration of greater than about 100-times that used in the final staining solution, then diluted one or more times with an aqueous solvent or a buffer solution such that the dye is present in an effective amount. The buffer solution may be, for example, a buffered saline (preferably non-phosphate for some viability discrimination applications), or a Tris(hydroxymethyl)aminomethane (TRIS) buffer (preferably containing EDTA). Typically, the dye is first dissolved in 100% DMSO, and then diluted with buffer.

The staining solution, containing an effective amount of dye, is then combined with a sample for a sufficient amount of time to form a dye-analyte complex. An effective amount of dye is the amount of dye sufficient to give a detectable fluorescence response in combination with the desired analyte. The dye concentration in the staining solution must be sufficient both to contact the analyte in the sample and to combine with the analyte in an amount sufficient to give a signal, but too much dye may cause problems with background fluorescence. The optimal concentration and composition of the staining solution is determined by the nature of the sample (including physical, biological, biochemical and physiological properties), the nature of the dye-analyte interaction (including the transport rate of the dye to the site of the analyte), and the nature of the analysis being performed, and can be determined using standard procedures, similar to those described in examples below.

The analyte of interest is optionally enclosed within a biological structure (i.e. an organism or a discrete unit of an organism), free in solution (including solutions that contain biological structures), immobilized in or on a solid or semi-solid material, or is extracted from a biological structure (e.g. from lysed cells, tissues, organisms or organelles). Preferably, the analyte is present in an aqueous environment in order to facilitate contact with the dye.

The sample is combined with the staining solution by any means that facilitates contact between the dye and the analyte. Typically the contact occurs through simple mixing, as in the case where the sample is a solution. A staining solution containing the dye may be added to the analyte solution directly or may contact the analyte solution in a liquid separation medium such as an electrophoretic liquid, sieving matrix or running buffer, or in a sedimentation (e.g. sucrose) or buoyant density gradient (e.g. containing CsCl), or on an inert matrix, such as a blot or gel, a testing strip, or any other solid or semi-solid support. Suitable supports also include, but are not limited to, polymeric microparticles (including paramagnetic microparticles), polyacrylamide and agarose gels, nitrocellulose filters, computer chips (such as silicon chips), natural and synthetic membranes, liposomes and alginate hydrogels, and glass (including optical filters), and other silica-based and plastic support. The dye is optionally combined with the analyte solution prior to undergoing gel or capillary electrophoresis, gradient centrifugation, or other separation step, during separation, or after the nucleic acids or lipid-complexed proteins undergo separation. Alternatively, the dye is combined with an inert matrix or solution in a capillary prior to addition of the analyte solution, as in pre-cast gels, capillary electrophoresis or preformed density or sedimentation gradients.

The sample is combined with the dye for a time sufficient to form the fluorescent dye-analyte complex, preferably the minimum time required to give a high signal-to-background ratio. Although all of the present dyes are nucleic acid stains and lipid-complexed protein stains, detectable fluorescence within biological structures or in gels requires entry of the dye across the biological membrane or into gels. Optimal staining with a particular dye is dependent upon the physical and chemical nature of the individual sample and the sample medium, as well as the property being assessed. The optimal time is usually the minimum time required for the dye, in the concentration being used, to achieve the highest target-specific signal while avoiding degradation of the sample over time and minimizing all other fluorescent signals due to the dye. For example, where the dye is chosen to be selective for a particular nucleic acid polymer or type of cell, the optimal time is usually the minimum time required to achieve the highest signal on that polymer or type of cell, with little to no signal from other nucleic acids or other cell types. Over time, undesirable staining may occur as even very low rates of diffusion may transport small amounts of the very sensitive dyes into other cell types, or staining selectivity may be lost as the cell membranes degrade, or as nucleases degrade nucleic acid polymers in cell-free systems.

Preferably, the dye is combined with the sample at a temperature optimal for biological activity of the analyte within the operating parameters of the dyes (usually between 5° C. and 50° C., with reduced stability of the dyes at higher temperatures). For in vitro assays, the dye is typically combined with the sample at about room temperature (23° C.). At room temperature, detectable fluorescence in a solution of nucleic acids is essentially instantaneous depending on the sensitivity of the instrumentation that is used; fluorescence in solutions is generally visible by eye within 5 seconds after the dye is added, and is generally measurable within 2 to 5 minutes, although reaching equilibrium staining may take longer. In particular, staining of lipid-complexed proteins in solution may be slower than equivalent staining of nucleic acids. Where a biological process is underway during in vitro analysis (e.g. in vitro transcription, replication, splicing, or recombination), the rapid labeling that occurs with the subject dyes avoids perturbation of biological system that is being observed. Gel staining at room temperature usually takes from 5 minutes to 2 hours depending on the thickness of the gel and the percentage of agarose or polyacrylamide, as well as the degree of cross-linking. Typically, post-stained mini-gels stain to equilibrium in 20-45 minutes. For cells and other biological structures, transport of dyes across membranes is required whether the membranes are intact or disrupted. For preferred embodiments, visibly detectable fluorescence is obtained at room temperature within 15-20 minutes of incubation with cells, commonly within about 5 minutes. Some embodiments give detectable fluorescence inside cells in less than about 2 minutes. This property is useful for observing nuclear structure and rearrangement, for example such as occurs during mitosis or apoptosis. Some of the dyes are generally not permeant to live cells with intact membranes; other dyes are generally permeant to eukaryotes but not to prokaryotes; still other dyes are only permeant to cells in which the cell membrane integrity has been disrupted (e.g. some dead cells). The relative permeability of the cell membrane to the dyes is determined empirically, e.g. by comparison with staining profiles or staining patterns of killed cells. The dye with the desired degree of permeability, and a high absorbance and quantum yield when bound to nucleic acids or lipid-complexed proteins, is selected to be combined with the sample.

The presence, location, and distribution of the analyte is detected using the spectral properties of the fluorescent dye-analyte complex. Spectral properties means any parameter that may be used to characterize the excitation or emission of the dye-nucleic acid complex including absorption and emission wavelengths, fluorescence polarization, fluorescence lifetime, fluorescence intensity, quantum yield, and fluorescence enhancement. Typically the spectral properties of excitation and emission wavelength are used to detect the dye complexes. The wavelengths of the excitation and emission bands of the dyes vary with dye composition to encompass a wide range of illumination and detection bands. This allows the selection of individual dyes for use with a specific excitation source or detection filter. In particular, complexes formed with dyes having a monomethine moiety (n=0) generally match their primary excitation band with the 532 nm excitation line of the frequency-doubled Nd-Yag laser, the 543 nm excitation line of the green He—Ne laser, the strong 546 nm emission of the Hg-arc lamp and sometimes the 568 nm excitation line of the Kr laser; whereas those with dyes with a trimethine moiety (n=1) primarily tend to match long wavelength excitation sources such as the orange HeNe laser (594 nm), the red HeNe laser (633 nm), the Kr laser (568 or 647 nm) and certain laser diodes, in particular the 635 nm laser diode; and complexes formed with dyes having a pentamethine moiety (n=2) primarily match very long excitation sources such as laser diodes or light emitting diodes (LEDs). In addition to the primary excitation peak in the visible range, the dye-nucleic acid complexes and dye-lipid-complexed protein complexes of the invention have a secondary absorption peak that permits excitation with UV illumination. Dyes with n=1 and n=2 typically form complexes that permit excitation beyond 600 nm.

Typically, the sample is excited by a light source capable of producing light at or near the wavelength of maximum absorption of the fluorescent analyte-complex, such as an ultraviolet or visible wavelength emission lamp, an arc lamp, a laser, or even sunlight or ordinary roomlight. Preferably the sample is excited with a wavelength within 20 nm of the maximum absorption of the fluorescent complex. Although excitation by a source more appropriate to the maximum absorption band of the dye-analyte complex results in higher sensitivity, the equipment commonly available for excitation of samples can be used to excite the dyes of the present invention.

The fluorescence of the complex is detected qualitatively or quantitatively by detection of the resultant light emission at a wavelength of greater than about 450 nm, preferably greater than about 480 nm, more preferably at greater than about 500 nm. The emission is detected by means that include visual inspection, CCD cameras, video cameras, photographic film, or the use of instrumentation such as laser scanning devices, fluorometers, photodiodes, quantum counters, plate readers, epifluorescence microscopes, scanning microscopes, confocal microscopes, flow cytometers, capillary electrophoresis detectors, or by means for amplifying the signal such as a photomultiplier tube. Many such instruments are capable of utilizing the fluorescent signal to sort and quantitate cells or quantitate the nucleic acids. Dyes can be selected to have emission bands that match commercially available filter sets such as that for fluorescein, tetramethylrhodamine or for detecting multiple fluorophores with several excitation and emission bands.

The source and type of sample, as well as the use of the dye, will determine which dye characteristics, and thus which dyes, will be most useful for staining a particular sample. For most applications, dyes are selected to give a quantum yield greater than about 0.1, more usefully 0.2 or 0.3, preferably greater than 0.5, when associated with an analyte; preferably the dyes have a quantum yield <0.02 and more preferably <0.01 or <0.005 when present in solution and not associated with an analyte. Preferably, upon associating with an analyte, the dye of the invention will exhibit a fluorescence enhancement greater than about 50 fold, preferably greater than 100 fold, more preferably greater than 200 fold and most preferably greater than 500 fold. Where the fluorescence of the dye-analyte complex or dye conjugate is detected utilizing sustained high intensity illumination (e.g. microscopy), dyes with a rate of photobleaching lower than commonly used dyes (e.g. fluorescein) are preferred, particularly for use in live cells. Where the dye must penetrate cell membranes or a gel, more permeant dyes are preferred, although some cells readily take up dyes that are shown to be impermeant to other cells by means other than passive diffusion across cell-membranes, e.g. by phagocytosis or other types of ingestion. Dyes that rapidly and readily penetrate cells do not necessarily rapidly penetrate gels. In applications where the nucleic acids are stained on a gel, the dye is also selected to have a relatively high binding affinity (preferably $K_d < 10^{-6}$ M); whereas in applications where the nucleic acid will be pre-stained prior to undergoing a separation step, such as gel or capillary electrophoresis, even higher binding affinity (preferably $K_d < 10^{-8}$ M) is preferred to ensure good separation. In staining nucleic acids in solution, high binding affinity translates into greater sensitivity to small amounts of nucleic acid, but dyes with a moderate binding affinity (preferably $10^{-6}$ M$<K_d<10^{-8}$ M) are more effective over a greater dynamic range. The photostability, binding affinity, quantum yield, and fluorescence enhancement of dyes are determined according to standard methods known in the art.

In a preferred embodiment, the dyes of the present invention are employed to detect the presence of lipid-poly(amino acids). In this instance the poly(amino acids) are typically immobilized on a solid or semi-solid matrix, but alternatively may be present in solution provided the correct concentration of lipid is present. Therefore, a method of the present invention for detecting lipid complexed poly(amino acids) in a sample comprises:

a) combining said sample with a staining solution, wherein said staining solution comprises one or more dyes of the present invention;
b) incubating said sample and said staining solution for a sufficient amount of time to form a dye-analyte complex;
c) illuminating said complex with an appropriate wavelength whereby the presence of said analyte is determined.

The sample containing a poly(amino acid) is in a solution, or immobilized on a solid or semi-solid matrix such as a blot or electrophoretic gel, the dye is preferably combined with the sample in an effective amount in the presence of a low percentage of a lipid. The amount of lipid or detergent required is typically a concentration available from a solution of 0.05-2.0% sodium dodecyl sulfate (SDS). Although the dyes of the invention may stain some proteins in the absence of lipid complexation, both the association of the dye with the protein and the resulting fluorescent signal are enhanced by the presence of a lipid complexing agent. Preferably the lipid complexing agent is an amphiphilic lipid, such as a detergent. Due to the limitation of a detergent for staining all proteins, the lipid-complexed protein is typically not associated with a biological cell but is free in solution or is immobilized on a solid or semi-solid matrix or is in an electrophoretic matrix or chamber, such as one used for gel or capillary electrophoresis.

The detergent is optionally added simultaneously with or as part of the sample or the staining solution, or is added thereafter to the combined mixture. The detergent is any amphiphilic surface active agent or surfactant that serves to coat the poly(amino acids) (i.e. non-covalently associate with the poly(amino acid)), or is a mixture of more than one detergent. Useful detergents include non-ionic, cationic, anionic, amphoteric and fluorinated surfactants. While there are a variety of detergents that are commercially available, including non-ionic, cationic, and anionic detergents, any detergent that is utilized in protein gel electrophoresis is a preferred detergent for the present invention. Typically, the detergent is an anionic detergent, preferably an alkyl sulfate or alkyl sulfonate salt. More preferably, the detergent is sodium dodecyl sulfate (SDS), sodium octadecyl sulfate, or sodium decyl sulfate, or a mixture thereof. Most preferably, the detergent is sodium dodecyl sulfate.

The dyes of the invention typically stain micelles, when present, so it is preferred that any detergent or detergent mixture present in the sample mixture, staining mixture, or combined mixture be present below the critical micelle concentration (CMC) for that detergent.

Combination of the dye with lipid-complexed proteins is facilitated when the proteins are first heated in the presence of detergent, including to temperatures in excess of 90° C. This heating step optionally occurs in the presence of the dye of the invention, although exposure to elevated temperatures may effect the stability of the dye.

The poly(amino acids) are optionally a synthetic or naturally occurring poly(amino acid), such as a peptide, polypeptide or protein. Poly(amino acids) that are stained and analyzed according to the present method optionally incorporate non-peptide regions (covalently or non-covalently) including lipid (lipopeptides and lipoproteins), phosphate (phosphopeptides and phosphoproteins), and/or carbohydrate (glycopeptides and glycoproteins) regions; or incorporate metal chelates or other prosthetic groups or non-standard side chains; or are multi-subunit complexes, or incorporate other organic or biological substances, such as nucleic acids. The poly(amino acids) are optionally relatively homogeneous or heterogeneous mixtures of poly(amino acids). In one aspect of the invention the poly(amino acids) are enzymes, antibodies, transcription factors, secreted proteins, structural proteins, or binding factors, or combinations thereof. The poly (amino acids) in the sample mixture are optionally covalently or non-covalently bound to a solid surface, such as a glass slide, multi-well plate, microtiter plate well, plastic pin or bead, or semiconductor material, or they are unbound. The staining of a poly(amino acid) that is bound to an analyte on a solid surface indicates the presence of the analyte as well as that of the poly(amino acid).

The poly(amino acids) are optionally unmodified, or have been treated with a reagent so as to enhance or decrease the mobility of the poly(amino acid) in an electrophoretic gel. Such reagents may modify poly(amino acids) by complexing with the peptide (to decrease migration), by cleaving selected peptide bonds (to increase migration of the resulting fragments), by changing the relative charge on the protein (as by phosphorylation or dephosphorylation) or by covalent coupling of a constituent such as occurs during glycosylation. The presence or interaction of such a reagent in the sample mixture is detected by the change in electrophoretic mobility of the treated poly(amino acids), relative to untreated poly (amino acids) having the same original composition, so that the distribution of the dye-poly(amino acid) complex indicates the presence of another analyte.

Typically the poly(amino acids) in the sample mixture have a molecular weight greater than about 500 daltons. More typically the poly(amino acids) are more than 800 daltons. Smaller polymers of amino acids (in the <1000 dalton range) are generally difficult to separate from the detergent front on denaturing gels, and typically do not adhere to filter membranes, but are still readily detected in solution. There is no precise upper limit on the size of the poly(amino acids) that may be stained and detected, except that they can not be so bulky that they precipitate out of solution, which also depends in part on the relative hydrophobicity of the poly(amino acid). Furthermore, poly(amino acids) greater than about 200,000 daltons are generally not effectively resolved with current gel technology. The poly(amino acids) present optionally have essentially the same molecular weight or fall within a range of molecular weights. In one embodiment of the invention, the poly(amino acids) present are a mixture of poly(amino acids) of different molecular weights that are used as molecular weight standards. A typical such mixture contains equal mass quantities of myosin, β-galactosidase, phosphorylase B, bovine serum albumin, ovalbumin, carbonic anhydrase, trypsin inhibitor, lysozyme and aprotinin.

Where the sample mixture is an aqueous solution, the poly(amino acids) of the sample mixture are typically present in a concentration of 10 ng/mL-50 µg/mL, more preferably in a concentration of 30 ng/mL-10 µg/mL, most preferably in a concentration of 50 ng/mL-5 µg/mL. Where the sample mixture is an electrophoretic gel, the poly(amino acids) of the sample mixture are typically present in a concentration of 1 ng/band-4 µg/band.

The poly(amino acids) are obtained from a variety of sources; such sources include biological fermentation media and automated protein synthesizers, as well as prokaryotic cells, eukaryotic cells, virus particles, tissues, and biological fluids. Suitable biological fluids include, but are not limited to, urine, cerebrospinal fluid, blood, lymph fluids, interstitial fluid, cell extracts, mucus, saliva, sputum, stool, physiological or cell secretions or other similar fluids.

Depending on the source of the sample mixture, it optionally contains discrete biological ingredients other than the desired poly(amino acids), including poly(amino acids) other than those desired, amino acids, nucleic acids, carbohydrates, and lipids, which may or may not be removed in the course of, prior to, or after staining. In one aspect of the invention, the poly(amino acids) in the sample mixture are separated from each other or from other ingredients in the sample by mobility (e.g. electrophoretic gel or capillary) or by size (e.g. centrifugation, pelleting or density gradient), or by binding affinity (e.g. to a filter membrane) in the course of the method. In another aspect of the invention, the sample mixture thought to contain the poly(amino acids) has undergone separation. In yet another aspect of the invention, the poly(amino acids) are not separated. Although lipid assemblies such as intact or fragmented biological membranes (e.g. membranes of cells and organelles), liposomes, or detergent micelles, and other lipids are optionally present in the sample mixture; the presence of large amounts of lipids, particularly lipid assemblies, Increases background labeling due to non-specific staining. For effective detection of labeled poly(amino acids), intact or fragmented biological membranes in the sample mixture are preferably removed, destroyed or dispersed prior to or in the course of labeling with this method. Typically treatment of the sample mixture by standard methods to remove some or all of such lipids, such as ammonium sulfate precipitation, solvent extraction or trichloroacetic acid precipitation is used. Alternatively or additionally, lipids are removed in the course of labeling the poly(amino acids) such as by electrophoretic separation or other separation techniques (e.g. centrifugation, including gradients), or are disrupted or dispersed below the concentration at which they assemble into micelles (critical micelle concentration) by mechanical means such as sonication. Naturally occurring lipids that are present below their critical micelle concentration are optionally used as a detergent for the purposes of the present invention. Typically, the sample mixture is essentially cell-free. This method is not effective for detecting proteins that remain in cells or are associated with biological membranes.

In another preferred embodiment the present dyes and staining solution are employed to detect nucleic acids in a sample. Again, the staining solution is combined with the sample to form a dye-nucleic acid complex and then illuminated with an appropriate wavelength whereby the nucleic acid is detected.

Therefore, when used to stain nucleic acids or to form conjugates of nucleic acids, the dye is combined with a sample that contains or is thought to contain a nucleic acid. The nucleic acid in the sample may be RNA or DNA, or a mixture or a hybrid thereof. Any nucleic acid is optionally single- or multiple-stranded. The nucleic acid may be a natural polymer (biological in origin) or a synthetic polymer (modified or prepared artificially). The nucleic acid polymer (preferably containing at least 8 bases or base pairs) may be present as nucleic acid fragments, oligonucleotides, or larger nucleic acid polymers with secondary or tertiary structure. The nucleic acid is optionally present in a condensed phase, such as a chromosome, or in a protein complex, such as a ribosome or nucleosome. The nucleic acid polymer optionally contains one or more modified bases or links or contains labels that are non-covalently or covalently attached. For example, the modified base is optionally a naturally occurring modified base, a known minor base, or is synthetically altered to contain an unusual linker such as morpholine derivatized phosphates, or peptide nucleic acids, or to contain a simple reactive functional group (<10 carbons) that is an aliphatic amine, carboxylic acid, alcohol, thiol or hydrazine, or to contain a fluorescent label or other hapten. The sensitivity of the dyes for polymers containing primarily modified bases and links may be diminished by interference with the binding mode.

The nucleic acid may be present in solution, immobilized on a solid or semi-solid matrix or present in a biological structure. Where the analyte is enclosed in a biological structure, as is typical for nucleic acids, the sample is typically incubated with the dye. While permeant dyes of this class have shown an ability to permeate biological structures rapidly and completely upon addition of the dye solution, any other technique that is suitable for transporting the dye into the biological structure is also a valid method of combining the sample with the subject dye. Some cells actively transport the dyes across cell membranes (e.g. endocytosis or ingestion by an organism or other uptake mechanism) regardless of their cell membrane permeability. Suitable artificial means for transporting the dyes (or pre-formed dye-nucleic acid complexes) across cell membranes include, but are not limited to, action of chemical agents such as detergents, enzymes or adenosine triphosphate; receptor- or transport protein-mediated uptake; liposomes or alginate hydrogels; phagocytosis; pore-forming proteins; microinjection; electroporation; hypo-osmotic shock; or minimal physical disruption such as scrape loading, patch clamp methods, or bombardment with solid particles coated with or in the presence of the dyes. Preferably, where intact structures are desired, the methods for staining cause minimal disruption of the viability of the cell and integrity of cell or intracellular membranes. Alternatively, the cells are fixed and treated with routine histochemical or cytochemical procedures, particularly where pathogenic organisms are suspected to be present. The cells are typically fixed immediately after staining with an aldehyde fixative that keeps the dye in the cells. In some cases, live or dead cells may even be fixed prior to staining without substantially increasing cell membrane permeability of previously live cells so that only cells that were already dead prior to fixation stain with the cell-impermeant dye.

Typically, the biological structure that encloses the nucleic acid is a cell or tissue, for example where the nucleic acid is present in a cell or interstitial space as a prokaryote or eukaryote microorganism, or as a virus, viroid, chromosome or organelle. Alternatively, the biological structure is not enclosed in a tissue or cell, and is present either as a virus or as a microorganism or other cell, or is present as a cellular component removed from its parent cell (e.g. a plasmid or chromosome, or a mitochondrion or nucleus or other organelle).

Typically, the biological structure is an organelle, chromosome or cell that is optionally inside a eukaryote cell. The cell that is present inside a eukaryote cell is typically a parasite or other infective agent such as a bacterium, protozoa, mycoplasma or mycobacterium. Where the nucleic acid is contained in a biological structure that is a cell, the cells are viable or dead cells or a mixture thereof, i.e. the integrity of the cell membrane is optionally intact or disrupted by natural (autolytic), mechanical or chemical means or by environmental means such as changes in temperature or pressure. Alternatively, the cells are blebbing or undergoing apoptosis or necrosis or are in a cycle of growth or cell division.

Cell types for which the dye is an effective nucleic acid stain include cells with or without nuclei, including but not limited to, eukaryotes, such as plant and animal cells (particularly vertebrate cells), including pollen and gamete cells; prokaryotes, particularly bacteria, including both Gram-negative and Gram-positive bacteria; as well as yeast and other fungi, and spores. In one embodiment, the sample comprises reticulocytes. The dyes are not equally effective in staining all cell types and certain dyes are generally more permeant than others. Live cells are less permeable to the dyes than dead cells, and prokaryotes are typically less permeable than eukaryotes.

The nucleic acids in the sample, both natural and synthetic, may be obtained from a wide variety of sources. The presence of the nucleic acid in the sample may be due to natural biological processes, or the result of a successful or unsuccessful synthesis or experimental methodology, undesirable contamination, or a disease state. The nucleic acid may be endogenous to the natural source or introduced as foreign material, such as by infection, transfection, or therapeutic treatment, Nucleic acids may be present in all, or only part, of a sample, and the presence of nucleic acids may be used to distinguish between individual samples, or to differentiate a portion or region within a single sample, or to identify the sample or characteristics of the sample.

Typically, the sample containing nucleic acids is a cell or is an aqueous or aqueous miscible solution that is obtained directly from a liquid source or as a wash from a solid material (organic or inorganic) or a growth medium in which cells have been introduced for culturing or a buffer solution in which nucleic acids or biological structures have been placed for evaluation. Where the nucleic acids are in cells, the cells are optionally single cells, including microorganisms, or multiple cells associated with other cells in two or three dimensional layers, including multicellular organisms, embryos, tissues, biopsies, filaments, biofilms, etc.

Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot. Industrial sources also include fermentation media, such as from a biological reactor or food fermentation process such as brewing; or foodstuffs, such as meat, grain, produce, or dairy products.

In yet another embodiment, the sample is immobilized in or on a solid or semi-solid matrix wherein the nucleic acids of interest are present on or in the matrix. In one aspect of the invention, the matrix is a membrane. In another aspect, the matrix is an electrophoretic gel, such as is used for separation and characterization of nucleic acids. In another aspect, the matrix is a silicon chip or glass slide, and the nucleic acids of interest have been immobilized on the chip or slide in an array.

Where the nucleic acid is present in a solution, the sample solution can vary from one of purified or synthetic nucleic acids such as oligonucleotides to crude mixtures such as cell extracts or homogenates or other biological fluids, or dilute solutions from biological, industrial, or environmental sources. In some cases it is desirable to separate the nucleic acids from a mixture of biomolecules or fluids in the solution prior to combination with the dye. Numerous techniques exist for separation and purification of nucleic acids from generally crude mixtures with other proteins or other biological molecules. These include such means as chromatographic and electrophoretic techniques, using a variety of supports or solutions or in a flowing stream. Alternatively, mixtures of nucleic acids may be treated with RNase or DNase so that the polymer that is not degraded in the presence of the nuclease can be discriminated from degradation products using the subject dyes.

The fluorescent dye-analyte complex is useful in essentially any application previously described for other fluorescent nucleic acid or protein stains (for example as described in U.S. Pat. No. 5,436,134 to Haugland et al. (1995); U.S. Pat. No. 5,445,946 to Roth et al. (1995); U.S. Pat. No. 5,534,416 to Millard et al, (1996); U.S. Pat. No. 5,616,502 to Haugland et al. (1997).

Once the dye-analyte complex is formed, its presence may be detected and used as an indicator of the presence, location, or type of analyte in the sample, or as a basis for sorting cells, or as a key to characterizing the sample or cells in the sample. Such characterization may be enhanced by the use of additional reagents, including fluorescent reagents. The amount of analyte in a sample can also be quantified by comparison with known relationships between the fluorescence of the dye-analyte complex and concentration of analyte in the sample.

In one aspect of the invention, the fluorescence response of the dye-analyte complex is used as a means for detecting the presence or location of the analyte in the sample. The fluorescent signal is detected by eye or by the instrumentation described above.

In addition, the staining profile that results from formation of the dye-analyte complex may be indicative of one or more characteristics of the sample. By staining profile is meant the shape, location, distribution, and spectral properties of the profile of fluorescent signals resulting from excitation of the fluorescent dye-analyte complexes. The sample can be characterized simply by staining the sample and detecting the staining profile that is indicative of a characteristic of the sample. More effective characterization is achieved by utilizing a dye that is selective for a certain characteristic of the sample being evaluated or by utilizing an additional reagent (as described below), where the additional reagent is selective for the same characteristic to a greater or lesser extent or where the additional reagent is selective for a different characteristic of the same sample.

In one embodiment of the invention, where the dye is selected to be membrane permeable or relatively impermeant to cell membranes, the staining profile that results from the formation of the dye-analyte complex is indicative of the integrity of the cell membrane, which in turn is indicative of cell viability. Alternatively, the more permeant dyes of the invention are used to stain both cells with intact membranes and cells with disrupted membranes, which when used in conjunction with a counterstain that gives a detectably different signal in cells with disrupted membranes, allows the differentiation of viable cells from dead cells. The counterstain that gives a detectably different signal in cells with disrupted membranes is optionally an impermeant dye of the invention or another reagent that indicates loss of integrity of the cell membrane or lack of metabolic activity of the dead cells.

In a further embodiment of the invention, the shape and distribution of the staining profile of dye-analyte complexes is indicative of the type of cell or biological structure that contains the stained nucleic acids. Cells may be discriminated by eye based on the visual fluorescent signal or be discriminated by instrumentation as described above, based on the spectral properties of the fluorescent signal. Typically the staining profile used to characterize the sample is indicative of the presence, shape, or location of organelles or of cells, where the cells are located in a biological fluid, in a tissue, or in other cells.

In another aspect of the invention, the dye-analyte complex is used as a fluorescent tracer or as a probe for the presence of a second analyte. In one aspect of the invention, the dye-analyte complex is used as a size or mobility standard, such as in electrophoresis or flow cytometry. Alternatively, the fluorescent signal that results from the interaction of the dye with the first analyte can be used to detect or quantitate the activity or presence of other molecules that interact with the first analyte.

Applications of Chemically Reactive Cyanine Dyes

The reactive dyes of the invention are particularly useful for immobilizing the dye on a surface or substrate, such as a polymeric microparticle, polymeric membrane, fiber, or silicon chip. In this embodiment, the dye is useful as a capture reagent for purification or detection of an analyte, particularly nucleic acids. Alternatively, the immobilized dyes are useful for moving associated analytes from one environment to another via mechanical means. Where the subject dyes are attached to a surface, the surface can also function as a quantitative or qualitative indicator of an analyte in solution, such as a test strip or dipstick.

The reactive dyes of the invention are also useful as detection reagents during the separation and purification of nucleic acids. For example the dyes of the invention can be conjugated to agar or agarose and used to cast plates or gels that are then useful for spot assays to quantitate nucleic acids. The ability of the reactive dyes of the invention to form stable covalent bonds with a variety of substrates allows the attachment of nucleic acid stains to electrophoretic gel matrices (producing very stable and uniformly stained pre-prepared gels).

Alternatively, where nucleic acids are analyzed using capillary electrophoresis, the dyes of the invention may be conjugated in a small "band" or region in the capillary, resulting in detection of nucleic acids with high sensitivity, as the detecting reagent is concentrated into a small volume, allowing efficient illumination using a laser or other excitation source. Where a conjugated dye is used in this fashion, the dye is optionally utilized only to capture the nucleic acids, with detection accomplished by another detection reagent, or the fluorescent enhancement upon binding nucleic acids is utilized to detect the capture event itself.

Where the dye is covalently bound to a substrate, such as a polymeric microparticle or membrane, the nucleic acids that are associated with the bound dye can be used as templates for translation and replication. Where the dye of the invention possesses a particularly high affinity for nucleic acids, passing a solution containing nucleic acids over a suitable labeled polymer matrix results in depletion of nucleic acids from the solution. The complexed nucleic acids can then be utilized in place or extracted from the matrix for further analysis or utilization.

Alternatively, a reactive dye of the invention can be associated with purified nucleic acids and covalently linked to the nucleic acids, which are then transferred to a membrane by blotting, and covalently bound to the polymeric membrane, resulting in a permanently labeled blot.

The dyes are optionally covalently bound to a molecule, such as a dextran, which is normally excluded from live cells. When dead or permeabilized cells then take up these molecules, the bound dye interacts with intracellular nucleic acids, giving rise to fluorescence. Similarly, the dye-conjugates of the invention possess utility for retaining conjugated substances within cells. This is particularly useful for conjugated substances that are typically excreted from living cells relatively quickly, such as small organic molecules or by-products of enzyme activity.

The dye is optionally conjugated to a substance selected such that the resulting conjugate has substantially different physical properties than those of the unbound dye, for example, conjugation of a dye of the invention to a polysaccharide or a poly(ethylene glycol) polymer to influence solubility, cellular retention, or ability to bind analytes.

Applications of Covalently Labeled Nucleic Acids

The dyes of the invention are useful for labeling unmodified nucleic acids covalently (typically using a photoreactive dye) so that the labeled nucleic acid retains its label through capillary transfer or electrophoretic transfer to filter membranes and subsequent hybridization (for example as in Southern blotting). The dyes are also useful in Southwestern analysis, wherein the dye is first coupled covalently to a nucleic acid, and the nucleic acid is then used to probe a Western blot containing putative nucleic acid-binding proteins. Fluorescence enhancement indicates locations on the blot membrane where the nucleic acid has been captured by the immobilized protein. Conjugates of proteins that do not interact specifically with nucleic acids do not exhibit similar fluorescence enhancement when used at similar concentrations, and in the absence of detergent. Similar interactions are useful for detecting immobilized DNA. Alternatively, where the protein is labeled with a second reagent, colocalization of that reagent and the dye of the invention indicates an interaction between the dye and the protein. This type of assay is also useful for analyzing nucleic acid-binding drugs.

Where the dyes of the invention are used to covalently label nucleic acids, the labeled nucleic acid is useful as a probe to detect interactions between nucleic acid-binding drugs or proteins, where the drug or protein has been labeled with a second fluorophore or a fluorescence quenching agent. Binding of the nucleic acid with the drug or protein results in loss of fluorescence. In this way, the nucleic acid-binding drug or protein can be quantitated, and the presence or absence of either inhibitors or enhancers of nucleic acid binding could be identified. This application is also useful for in vivo or in vitro studies, for example in the study of interactions between SSB (single strand binding protein) and single stranded DNA, histones and double stranded DNA, sequence specific binding factors and their cognate sequences, or mismatch repair enzymes and mismatch regions of DNA hybrids.

Dye-labeled nucleic acids are useful for monitoring transfection into cells, either by the labeled nucleic acid itself, or where another molecule is cotransfected and the labeled nucleic acid is simply a tracer. The amount of labeled nucleic acid in a cell could be used to standardize the copy number of transiently transfected plasmids in reporter gene assays, such as chloramphenicol acetyltransferase assays (CAT assays).

Dye-conjugates of nucleic acids possess utility for detecting hybridization, as the dye-conjugate typically exhibits a change in fluorescence enhancement upon binding to a complementary strand of nucleic acid. Dye-labeled nucleic acids are also useful for following triplex formation, or strand invasion, during DNA recombination. If two dyes capable of energy transfer are used, then real-time measurements of hybridization or strand invasion/displacement may be made. In particular both the interactions of an antisense oligonucleotides with nucleic acids and RNA splicing could be followed using this methodology.

Where the dye is used to covalently label a nucleic acid, the nucleic acid could then be ligated to another unlabeled nucleic acid, so that even if the labeled nucleic acid fragment is unable to hybridize or bind proteins efficiently, the unlabeled portion retains full biological activity. However, the nucleic acid is readily detectable due to the presence of the attached dye.

The dyes of the invention also serve as haptens for secondary detection. The use of labeled antibodies directed against the dyes of the invention allows for signal amplification in the detection of either a conjugated substance, or a labeled nucleic acid. Alternatively, where the conjugated substance is a specific binding pair member, the specific binding pair member may be used to amplify the detectable signal of the cyanine dye, typically by immunological methods. In this embodiment, the conjugated substance is typically a hapten, biotin or digoxigenin or a non-nucleic acid-binding dye. The dye-conjugate forms a nucleic acid-dye complex, producing enhancement of its fluorescence. The complex is then labeled with the complement of the specific binding pair member, which is typically labeled with a fluorophore, producing an additional fluorescent enhancement.

Additional Detection Reagents

The dyes of the invention can be used in conjunction with one or more additional reagents that are separately detectable. The additional reagents may be separately detectable if they are used separately, e.g. used to stain different aliquots of the same sample, or if they stain different parts or components of a sample, regardless of whether the signal of the additional reagents is detectably different from the fluorescent signal of the dye-analyte. Alternatively, the dye of the invention is selected to give a detectable response that is different from that of other reagents desired to be used in combination with the subject dyes. Preferably the additional reagent or reagents are fluorescent and have different spectral properties from those of the dye-analyte complex. For example, dyes that form complexes that permit excitation beyond 600 nm can be used in combination with commonly used fluorescent antibodies such as those labeled with fluorescein isothiocyanate or phycoerythrin. Any fluorescence detection system (including visual inspection) can be used to detect differences in spectral properties between dyes, with differing levels of sensitivity. Such differences include, but are not limited to, a difference in excitation maxima, a difference in emission maxima, a difference in fluorescence lifetimes, a difference in fluorescence emission intensity at the same excitation wavelength or at a different wavelength, a difference in absorptivity, a difference in fluorescence polarization, a difference in fluorescence enhancement in combination with target materials, or combinations thereof.

The detectably different dye is optionally one of the dyes of the invention having different spectral properties and different selectivity. In one aspect of the invention, the dye-analyte complex and the additional detection reagents have the same or overlapping excitation spectra, but possess visibly different emission spectra, generally having emission maxima separated by >10 nm, preferably >20 nm, more preferably >50 nm. Simultaneous excitation of all fluorescent reagents may require excitation of the sample at a wavelength that is suboptimal for each reagent individually, but optimal for the combination of reagents. Alternatively, the additional reagent(s) can be simultaneously or sequentially excited at a wavelength that is different from that used to excite the subject dye-analyte complex. In yet another alternative, one or more additional reagents are used to quench or partially quench the fluorescence of the dye-analyte complex, such as by adding a second reagent to improve the selectivity for a particular nucleic acid or the AT/GC selectivity.

The additional dyes are optionally used to differentiate cells or cell-free samples containing the desired analyte according to size, shape, metabolic state, physiological condition, genotype, or other biological parameters or combinations thereof. The additional reagent is optionally selective for a particular characteristic of the sample for use in conjunction with a non-selective reagent for the same characteristic, or is selective for one characteristic of the sample for use in conjunction with a reagent that is selective for another characteristic of the sample. In one aspect of the invention, the additional dye or dyes are metabolized intracellularly to give a fluorescent product inside certain cells but not inside other cells, so that the fluorescence response of the cyanine dye of the invention predominates only where such metabolic process is not taking place. Alternatively, the additional dye or dyes are specific for some external component of the cell such as cell surface proteins or receptors, e.g. fluorescent lectins or antibodies. In yet another aspect of the invention, the additional dye or dyes actively or passively cross the cell membrane and are used to indicate the integrity or functioning of the cell membrane (e.g. calcein AM or BCECF AM). In another aspect, the additional reagents bind selectively to AT-rich nucleic acids and are used to indicate chromosome banding, in another aspect of the invention, the additional reagent is an organelle stain, i.e. a stain that is selective for a particular organelle, for example the additional reagent(s) may be selected for potential sensitive uptake into the mitochondria (for example as described in U.S. Pat. No. 5,459,268 to Haugland et al. (1995)) or for uptake due to pH gradient in an organelle of a live cell (U.S. Pat. No. 5,869,689 to Zhang et al. (1999)).

The additional dyes are added to the sample being analyzed to be present in an effective amount, with the optimal concentration of dye determined by standard procedures generally known in the art. Each dye is optionally prepared in a separate solution or combined in one solution, depending on the intended use. After illumination of the dyed cells at a suitable wavelength, as above, the cells are analyzed according to their fluorescence response to the illumination. In addition, the differential fluorescence response can be used as a basis for sorting the cells or nucleic acids for further analysis or experimentation. For example, all cells that "survive" a certain procedure are sorted, or all cells of a certain type in a sample are sorted. The cells can be sorted manually or using an automated technique such as flow cytometry, according to the procedures known in the art, such as in U.S. Pat. No. 4,665,024 to Mansour, et al. (1987).

D. Kits of the Invention

In one aspect of the invention, the cyanine dyes of the invention are incorporated into a kit for commercial use. In one embodiment, the kit comprises a selection of dyes of the invention, typically present as a concentrated stock solution in a non-aqueous solvent, preferably DMSO. Where the kit is a "sampler" kit of cyanine dyes, the kit comprises 2-8 distinct cyanine dyes, preferably 4-6 distinct cyanine dyes.

In another embodiment of the invention, the reagent kit comprises a stock solution of the dye of the invention, typically present in a DMSO solution; a buffer suitable for dilution of the stock solution, and optionally further comprises a standard or an additional detection reagent, or both. The standard is optionally one or more nucleic acids (for nucleic acid detection/quantification), or one or more proteins (for protein detection/quantification). The additional detection reagent is typically an organelle stain, a labeled immunoreagent, a drug, or an enzyme.

In yet another embodiment of the invention, the reagent kit comprises a stock solution of the dye of the invention, typically present in a DMSO solution, a buffer suitable for dilution of the stock solution, a silicon chip or glass slide, and nucleic acid standards.

A detailed description of the invention having been provided above, the following examples are given for the purpose of illustrating the invention and shall not be construed as being a limitation on the scope of the invention or claims.

EXAMPLES

Example 1

Preparation of aza-benzoxazole Precursors

The following 4-methyl-2-methylthiooxazolopyridinium tosylates are prepared by heating the corresponding 2-methylthiooxazolopyridines (M. Y. Chu-Moyer and R. Berger, J. Org. Chem. 60, 5721-5725 (1995)) with one equivalent of methyl tosylate at 100-110° C. for one hour:

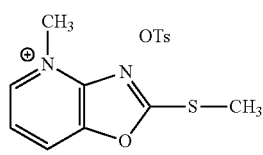

Compound 1

(4-methyl-2-methylthiooxazolo[4,5-b]pyridinium tosylate)

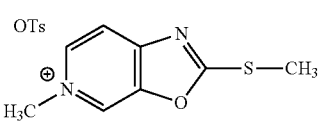

Compound 2

(6-methyl-2-methylthiooxazolo[5,4-c]pyridinium tosylate):

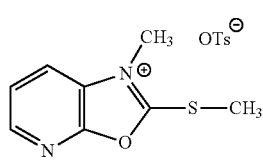

Compound 3

(1-methyl-2-methylthiooxazolo[5,4-b]pyridinium tosylate):

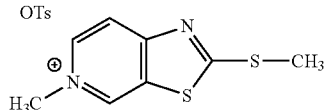

Compound 4

(4-methyl-2-methylthiooxazolo[4,5-b]quinolinium tosylate):

Example 2

Preparation of 5-methyl-2-methylthiothiazolo[4,5-b]pyridinium tosylate (Compound 5)

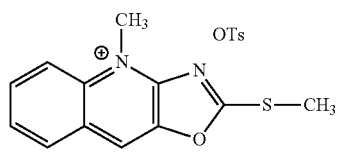

To 0.626 g of 2-methylthiothiazolo[4,5-b]pyridine (Smith, K., Lindsay, C., Morris, I. K., Matthews, I. and Pritchard, G. J., Sulfur Letters 17, 197-216 (1994)), is added 0.71 g methyl tosylate. The mixture is heated at 120° C. for one hour. After cooling, the resulting oily mixture is washed with 10 mL of ethyl acetate. After the ethyl acetate is decanted, Compound 5 is isolated as an oil.

Example 3

Preparation of 5-methyl-2-methylthiothiazolo[5,4-c]pyridinium tosylate (Compound 6)

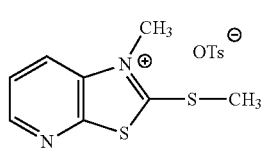

Compound 6

A mixture of 0.127 g of 2-methylthiothiazolo[5,4-c]pyridine (from methylation of thiazolo[5,4-c]pyridine-2(1H)-thione with potassium carbonate and methyl iodide) and 0.143 g methyl tosylate is heated at 120° C. for one hour. Ethyl acetate (8 mL) is added, the mixture is stirred for 30 minutes, and Compound 6 is isolated by suction filtration.

Example 4

Preparation of 3-methyl-2-methylthiothiazolo[5,4-b]pyridinium tosylate (Compound 7)

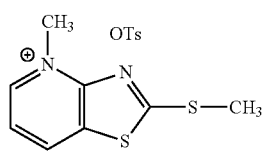

Compound 7

A mixture of 1.285 g of 3-amino-2-chloropyridine, 0.48 g NaH (from a hexane-washed 60% dispersion of NaH in mineral oil), 0.6 mL $CS_2$ and 10 mL DMF is heated at 110-120° C. for one hour to yield thiazolo[5,4-b]pyridine-2(1H)-thione. The thione is methylated with potassium carbonate and methyl iodide in DMF at room temperature to give the methylthio derivative, 2-methylthiothiazolo[5,4-b]pyridine, which is subsequently heated with one equivalent of methyl tosylate at 100° C. for one hour to yield Compound 7.

Similarly, 6-chloro-4-methyl-2-methylthiothiazolo[4,5-b]pyridinium tosylate is prepared from 6-chlorothiazolo[4,5-b]pyridine-2(1H)-thione:

Compound 8

6-bromo-4-methyl-2-methylthiothiazolo[4,5-b]pyridinium tosylate is prepared from 2-amino-3,5-dibromopyridine:

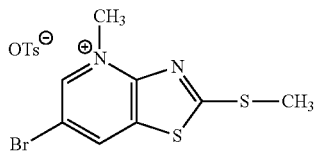
Compound 9

4-methyl-2-methylthio-6-trifluoromethylthiazolo[4,5-b]pyridinium tosylate is prepared from 2-amino-3-chloro-5-trifluoromethylpyridine:

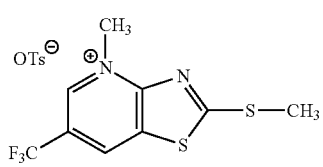
Compound 10 and 1-methyl-2,7-bis(methylthio)thiazolo[5,4-d]pyridinium tosylate is prepared from 5-amino-4,6-dichloropyrimidine:

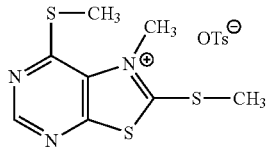
Compound 11

Example 5

Preparation of 3-acetoxy-1-methyl-2-acetylimino-1,2-dihydropyridine, p-toluenesulfonic acid salt (Compound 12)

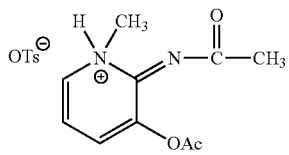

2-Amino-3-hydroxypyridine (14.48 g) is triacetylated by heating with 3 equivalents of acetic anhydride at 120-130° C. for 4 hours to yield, after silica gel column purification, 10.3 g of 3-acetoxy-2-acetimidopyridine. This intermediate compound is heated for 2 days at 65° C. with 3 equivalents of methyl tosylate to yield 7 g of Compound 12.

Example 6

Preparation of 5-bromo-3-mercapto-2-methylaminopyridine (Compound 13)

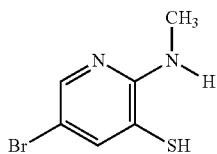

Compound 13 is prepared by heating Compound 9 (1.99 g) with 30 mL methanol and 15 mL of 10% NaOH at 80° C. for 8 hours. The pH is adjusted to 6-7 with acetic acid and the volume is reduced to ~10 mL. The residue is filtered to yield 0.76 g of Compound 13.

Example 7

Preparation of Compound 14

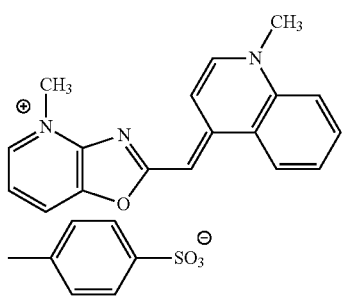
Compound 14

To 0.55 g of Compound 1 and 0.49 g of 1,4-dimethylquinolinium tosylate in 10 mL of $CH_2Cl_2$ at room temperature is added 0.24 mL of triethylamine. After 6 hours, the product is suction filtered to yield 0.42 g of Compound 14.

Example 8

Preparation of Compounds 15, 16, 17, 18, 19, 20, 21, and 44

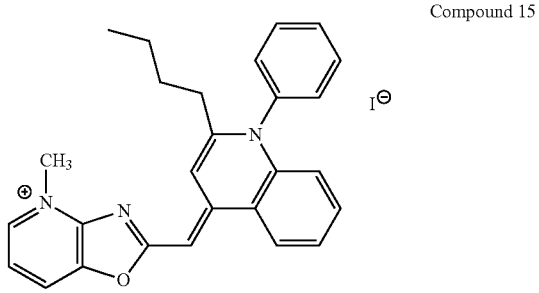 [SMILES: CCCCC1=C/C(=C\c2nc3c(ccc[n+]3C)o2)c2ccccc2N1c1ccccc1 ; [I-]]
Compound 15

To a solution of 0.235 g of 4-methyl-1-phenyl-2-quinolone in 15 mL THF at −78° C., is added 0.6 mL of a 2.5 M solution of 1-butyl lithium in THF. After 1 hr at −78° C., 1 mL of acetic acid is added. The reaction mixture is stirred for 1 hr at room temperature. The volatiles are evaporated and the residue is dissolved in 10 mL CH$_2$Cl$_2$. Compound 1 (0.7 g) and 1 mL triethylamine are added. After 1 hr at room temperature the solvent is evaporated, the crude product is dissolved in 10 mL of methanol and the solution is then added to 2.5 g NaI in 60 mL water. The product, Compound 15, is filtered and further purified by column chromatography on silica gel.

Similarly prepared except using phenyl lithium instead of butyl lithium is Compound 16, which can be recrystallized from a mixture of DMF and ethyl acetate.

Compound 16

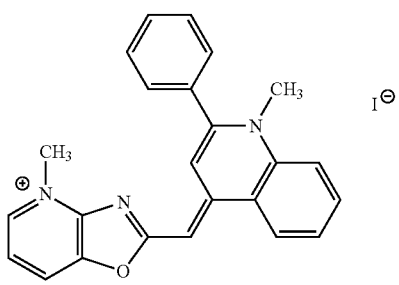

Compound 17 is prepared similarly from 4-methyl-1-phenyl-2-quinolone

Compound 17

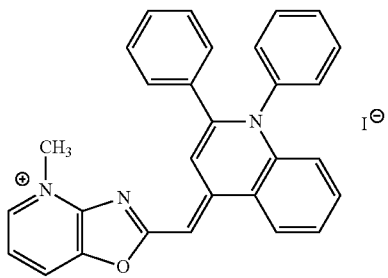

Compound 18 is prepared similarly from 1-ethyl-6,7-methylenedioxy-4-methyl-2-quinolone Compound 18

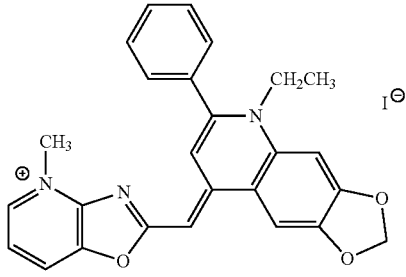

Compound 19 is prepared similarly from 6-methoxy-1,4-dimethyl-2-quinolone

Compound 19

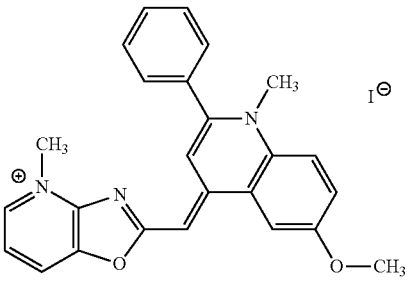

Compound 20 is prepared similarly from 6,7-dimethoxy-1,4-dimethyl-2-quinolone

Compound 20

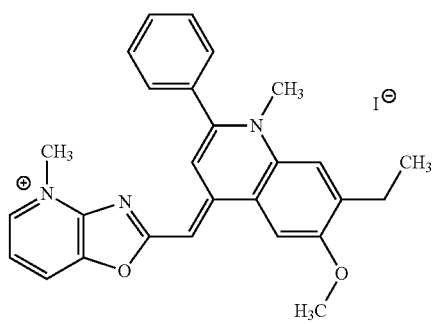

Compound 21 is prepared similarly from 7-methoxy-1,4-dimethyl-2-quinolone.

Compound 21

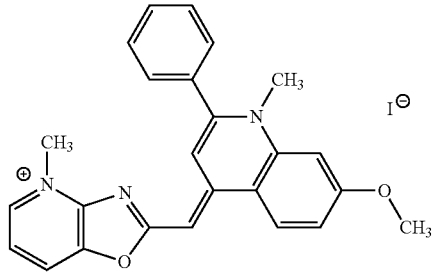

Compound 44 is prepared similarly, except that Compound 9 is used instead of Compound 1:

Compound 44

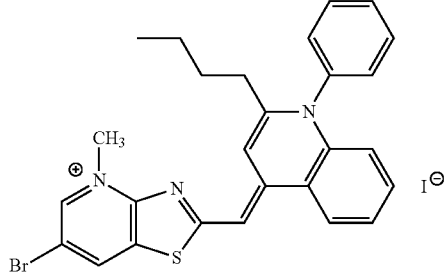

Example 9

Preparation of Compound 22

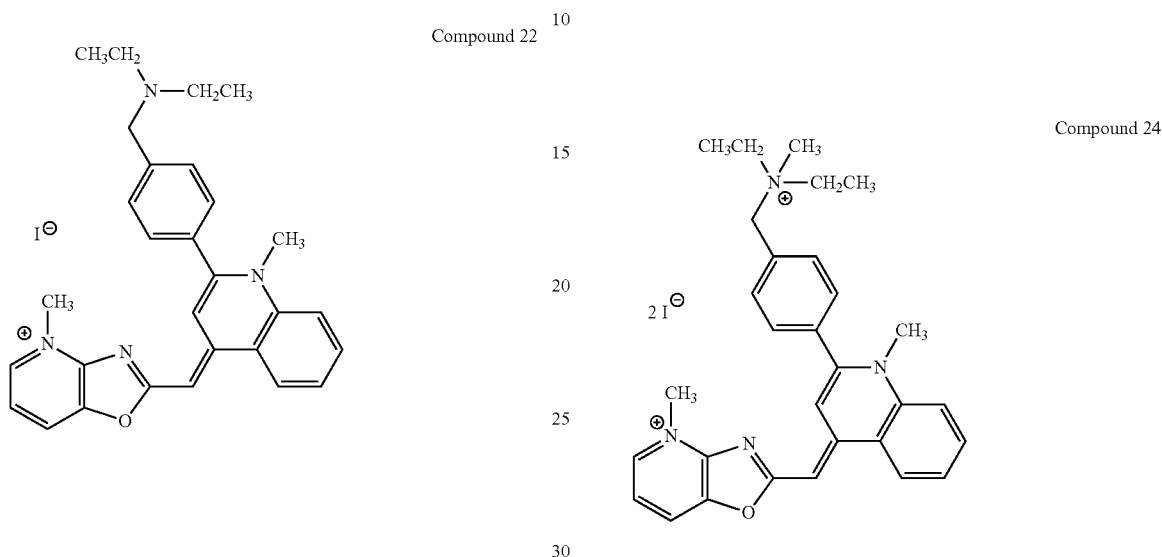

To 0.605 g of 4'-bromobenzyldiethylamine in 10 mL of THF at −78° C. under nitrogen is added 0.8 mL of a 2.5 M butyl lithium in THF, followed by a solution of 0.173 g of 1,4-dimethyl-2-quinolone in 10 mL of THF. After one hour at −78° C., 1 mL of acetic acid is added. After warming to room temperature for another hour the volatiles are evaporated and the residue is dissolved in 10 mL $CH_2Cl_2$. To this solution is added 0.67 g of Compound 2, followed by 1 mL triethylamine. After one hour at room temperature the volatiles are evaporated and the residue is dissolved in 7 mL of methanol. This solution is added to a solution of 2.25 g NaI and 0.8 g NaOH in 50 mL water. Compound 22 is filtered, dried and recrystallized from a mixture of DMF and ethyl acetate.

Compound 23 is prepared similarly, using 6-methoxy-1,4-dimethyl-2-quinolone.

Example 10

Preparation of Compound 24

The compound is prepared by heating 0.1 g of Compound 22 in 5 mL DMF with 0.5 mL methyl iodide at 60° C. in a sealed tube for 2 hours. After the reaction mixture is cooled to room temperature, 5 mL ethyl acetate is added and Compound 24 is collected by suction filtration.

Compound 25 is similarly obtained from Compound 23.

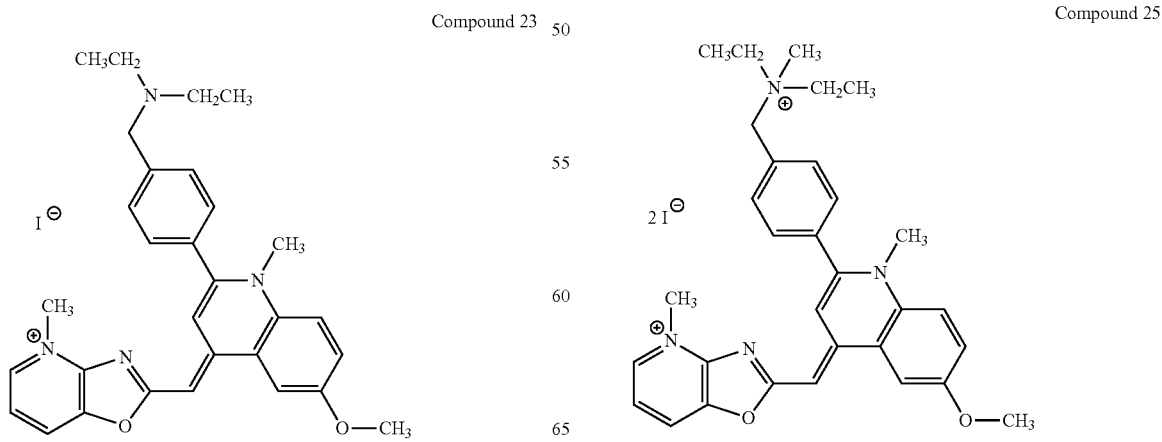

Example 11

Preparation of Compounds 26 and 27

Compound 26

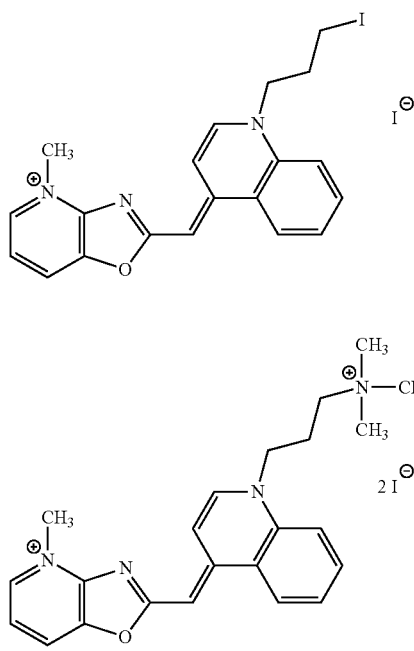

Compound 27

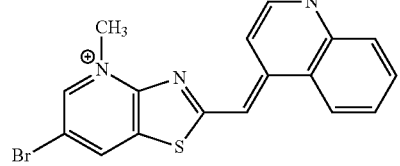

A mixture of 1.06 g of Compound 1, 0.88 g of 1-(3'-iodopropyl)-4-methylquinolinium iodide (U.S. Pat. No. 5,321,130 to Yue et al. (1994)), 15 mL CH$_2$Cl$_2$ and 0.28 mL triethylamine is stirred at room temperature for 30 minutes. The volatiles are evaporated and the residue is dissolved in 10 mL methanol. The resulting solution is added to 4.5 g NaI in 60 mL water. Compound 26 is obtained by suction filtration. A solution of Compound 26 (0.15 g) and 1 mL of a 25% trimethylamine in methanol solution are heated in a sealed tube at 75-80° C. for 7 hours. Following cooling and filtration, Compound 27 is recrystallized from a mixture of DMF and CH$_2$Cl$_2$.

Compound 47 is similarly prepared from Compound 9

Compound 47

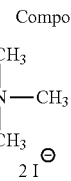

Example 12

Preparation of Compound 28

A mixture of 0.2 g of Compound 26, 15 mL DMF and 0.029 mL N,N,N',N'-tetramethylpropanediamine is heated at 80° C. for 4 days. To the solution is added 6 mL of chloroform and Compound 28 is isolated by suction filtration.

Compound 28

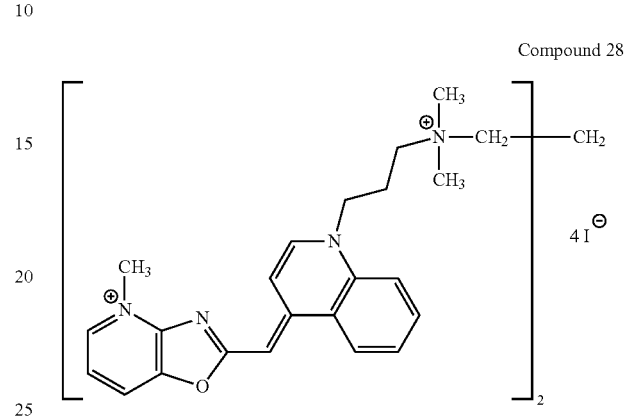

Example 13

Preparation of Compounds 45 and 46

Compound 45

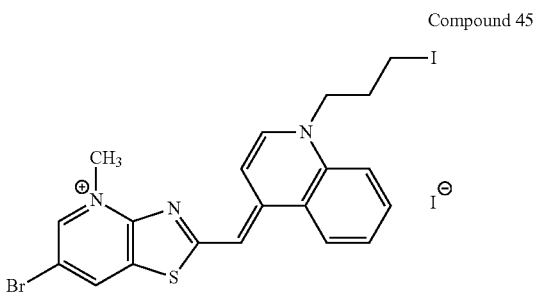

Compound 46

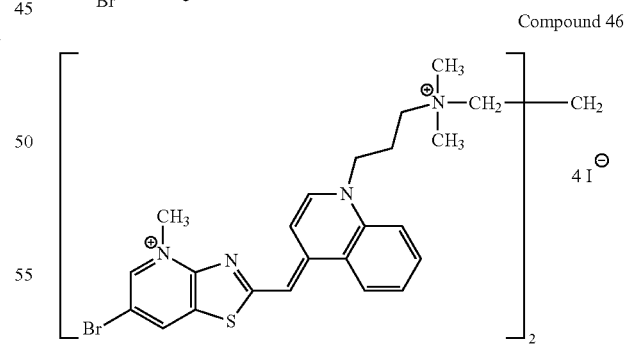

A mixture of 2.1 g of Compound 9, 1.5 g of 1-(3'-iodopropyl)-4-methylquinolinium iodide, 0.7 mL triethylamine and 30 mL CH$_2$Cl$_2$ is stirred at room temperature for 2 hours. Following evaporation, the residue is dissolved in 30 mL DMF and added to 8 g NaI in 200 mL water. Compound 45 is obtained by suction filtration. Compound 45 (1 g), 0.125 mL of N,N,N',N'-tetramethylpropanediamine and 8 mL DMF are heated at 80° C. for 4 days. Following cooling, 24 mL of chloroform is added and Compound 46 is purified by recrystallization for a mixture of DMF and methanol.

Example 14

Preparation of Compounds 29, 30, and 41

Compound 29

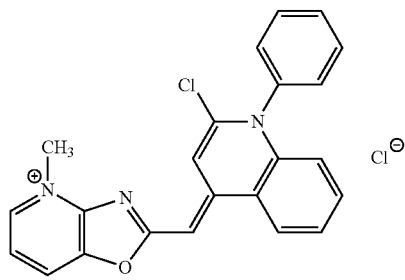

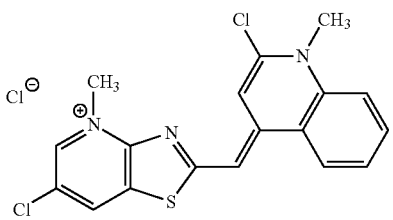

Compound 41

Example 15

Preparation of Compound 31

Compound 31

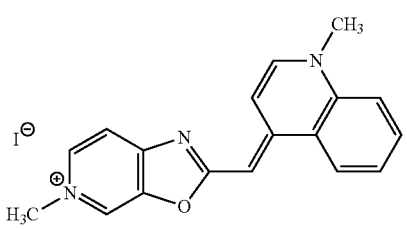

Triethylamine (0.1 mL) is added to 0.176 g of Compound 11 and 0.165 g of 1,4-dimethylquinolinium tosylate in 10 mL of CH$_2$Cl$_2$ at room temperature. After stirring for one hour, the organic layer is evaporated and the residue is dissolved in 2 mL of methanol and added dropwise to a solution of 1.5 g NaI in 25 mL of water. Compound 31 is recovered by suction filtration.

Example 16

Preparation of Compound 32

Compound 30

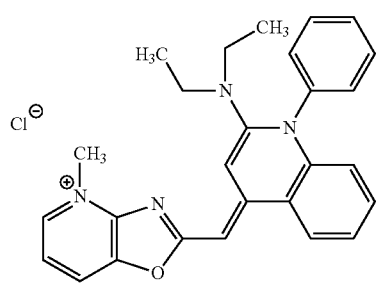

A mixture of 6 g of Compound 1, 3 g of 4-methyl-1-phenyl-2-quinolone, 8.9 mL diisopropylethylamine, and 1.2 mL of trimethylsilyl trifluoromethanesulfonate is heated at reflux in 100 mL of CH$_2$Cl$_2$ for 1 hour. The reaction mixture is cooled on ice and 100 mL of water is added slowly with stirring. The layers are separated and the aqueous layer is extracted with chloroform. The combined organic layers are washed with brine and dried over Na$_2$SO$_4$. The crude 4-oxazolopyridinyl-methylidenequinolone thus obtained is heated at reflux for 3 hours with 5.8 mL of phosphorus oxychloride and 100 mL of dichloroethane. The reaction mixture is cooled to room temperature, 100 mL of water is added and after 30 min, the crude product is recovered by filtration. The crude product is purified by chromatography on a silica gel column to yield Compound 29. A mixture of 0.1 g of Compound 29, 10 mL of dichloroethane and 0.27 mL of diethylamine is heated at 60° C. in a sealed tube for 2.5 hours. The volatile components are evaporated and the crude residue is purified by chromatography on a silica gel column to yield Compound 30.

Preparation of Compound 41 is similar to that of Compound 29, except that Compound 9 is used instead of Compound 1.

Compound 32

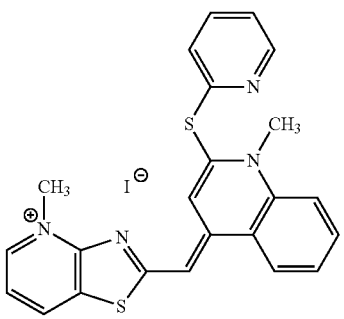

A mixture of 0.35 g of 1,4-dimethyl-2-quinolone, 0.56 mL phosphorus oxychloride, and 0.05 mL DMF is heated in 10 mL toluene at 70° C. for 2 hours. After cooling, 20 mL CH$_2$Cl$_2$ and 1.11 g 2-mercaptopyridine are added and the reaction mixture is heated overnight at 40° C. The volatiles are evaporated and to the residue is added 0.84 g of Compound 1, 1.4 mL of triethylamine and 20 mL CH$_2$Cl$_2$. After 2 hours, the volatiles are evaporated, the residue is dissolved in 3 mL methanol and the solution is added to 4.5 g NaI in 20 mL water. Compound 32 is purified by recrystallization from a mixture of DMF and ethyl acetate.

Example 17

Preparation of Compound 33

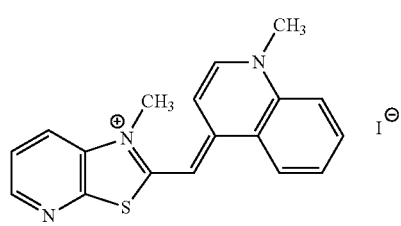
Compound 33

A mixture of 0.244 g of Compound 7, 0.225 g of 1,4-dimethylquinolinium tosylate, 0.14 mL triethylamine and 10 mL CH$_2$Cl$_2$ is stirred at room temperature overnight. The volatiles are evaporated, residue is dissolved in 4 mL of methanol, and the resulting solution is added to 1.5 g NaI in 25 mL water. Compound 33 is obtained by suction filtration.

Compounds 34, 35, 36, 37, 38, 39, and 40 are similarly prepared from 1,4-dimethylquinolinium tosylate and Compounds 6, 11, 4, 10, 5, 9, and 8 respectively.

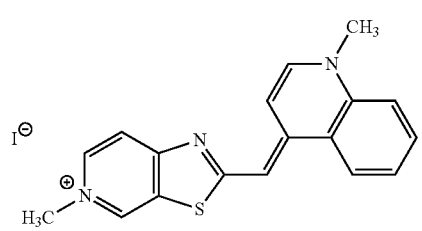
Compound 34

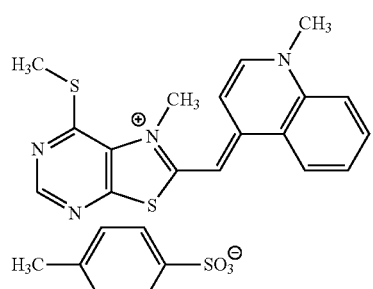
Compound 35

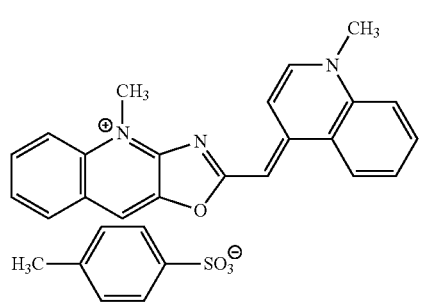
Compound 36

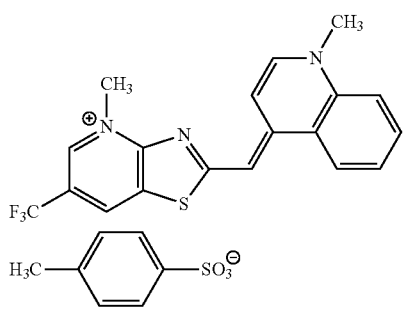
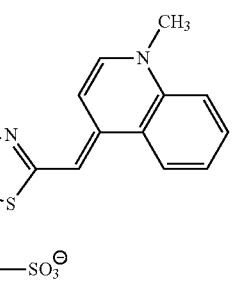
Compound 37

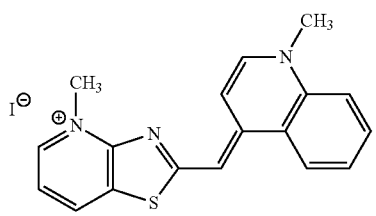
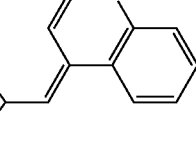
Compound 38

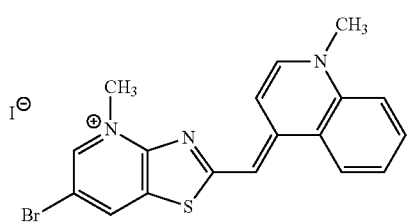
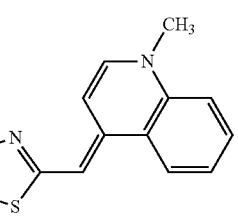
Compound 39

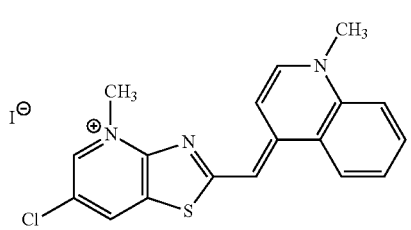
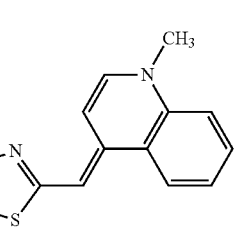
Compound 40

Example 18

Preparation of Compound 42

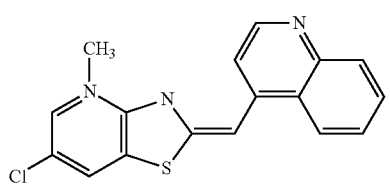
Compound 42

A mixture of 0.2 g of Compound 8, 0.065 mL of lepidine, 0.28 mL acetic anhydride and 5 mL DMF is heated at 110-120° C. for one hour. The reaction mixture is carefully diluted with a mixture of sodium bicarbonate and water and then extracted with chloroform. The chloroform is evaporated, and the resulting residue is purified by silica gel chromatography to yield Compound 42.

Compound 43 is similarly prepared from Compound 1.

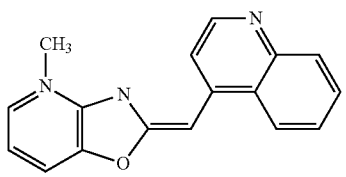

Compound 43

Example 19

Preparation of Compound 48

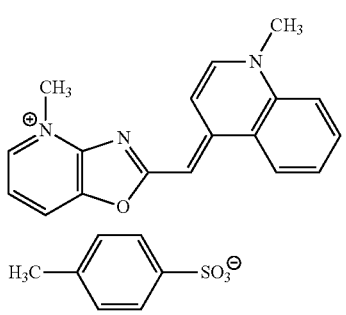

Compound 48

Compound 1 (0.36 g), 0.28 g of 1,4-dimethylpridinium tosylate, 0.17 mL of triethylamine and 20 mL of $CH_2Cl_2$ are stirred at room temperature for one hour, then stirred for an additional 3 days at −20° C. Compound 48 is isolated by suction filtration.

Example 20

Preparation of Compound 49

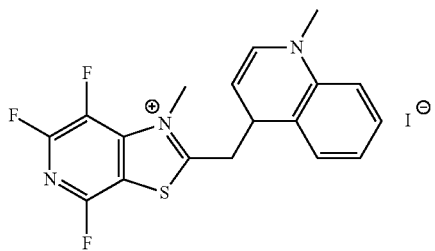

Compound 49

A solution of 4.2 mg of 3-methyl-2-methylthio-4,5,7-trifluorothiazolo[5,4-c]pyridinium tosylate (from 4-amino-2,3,5,6-tetrafluoropyridine by a procedure similar to that used for preparation of Compound 8), 3.3 g of 1,4-dimethylquinolinium tosylate and 1.7 mL of triethylamine is stirred in 20 mL $CH_2Cl_2$ at room temperature for 1 hour. The volatiles are evaporated and the residue is purified by chromatography on a silica gel column. The product is converted to Compound 49 with NaI in water.

Example 21

Preparation of Compound 50

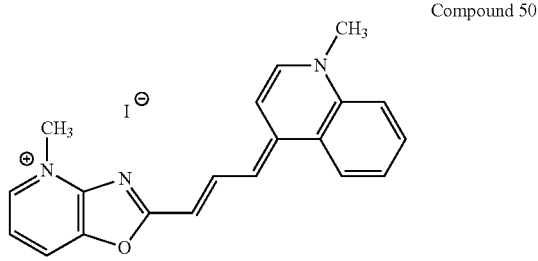 [SMILES: CN1C=C/C(=C\C=C\c2nc3c(ccc[n+]3C)o2)c2ccccc21 ; [I-]]

Compound 50

A mixture of 0.33 g of 1,4-dimethylquinolinium tosylate, 0.24 g of N,N'-diphenylformamidine, and 0.3 mL acetic anhydride is heated at 130° C. for 2 hours. Ethyl acetate (20 mL) is added and the solution is heated at reflux for 20 minutes. The mixture is cooled, and the resulting solid is dissolved in 5 mL dichloroethane. Compound 12 (0.34 g), 0.35 mL of diisopropylethylamine and 0.2 mL acetic anhydride are added. After stirring for 3 hours at room temperature, the volatiles are evaporated, the residue is dissolved in 3 mL of methanol and the solution is added dropwise to 1.5 g NaI in 20 mL water. Compound 50 is recovered by filtration and purified by chromatography on a silica gel column.

Example 22

Preparation of Compound 51

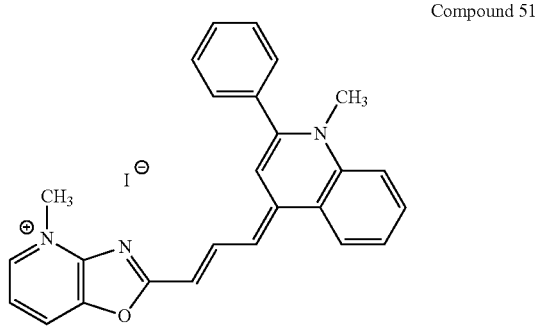 [SMILES: CN1C(c2ccccc2)=C/C(=C\C=C\c2nc3c(ccc[n+]3C)o2)c2ccccc21 ; [I-]]

Compound 51

A mixture of 1.9 g of Compound 12, 1.18 g of N,N'-diphenylformamidine, 2.1 mL of triethylamine and 50 mL dichloroethane is heated at 60-65° C. for 2 hours. After cooling, one equivalent of 1,4-dimethyl-2-phenylquinolinium salt (prepared in a manner similar to that for Compound 16) in 10 mL of dichloroethane is added, followed by 0.7 mL of additional triethylamine and 1.41 mL of acetic anhydride. After three hours, the volatiles are evaporated, the residue is dissolved in 10 mL DMF and the solution is added to 7.5 g of NaI in 120 mL water. Compound 51 is recrystallized from a mixture of methanol and ethyl acetate.

Example 23

Preparation of Compound 52

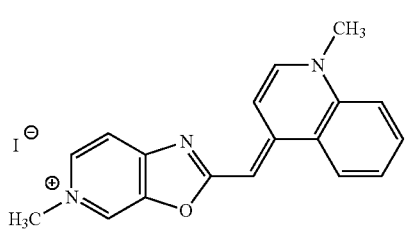

Compound 52

A mixture of 0.18 g of Compound 2, 0.17 g 1,4-dimethylpyridinium tosylate, 0.09 mL triethylamine and 20 mL CH$_2$Cl$_2$ is stirred at room temperature overnight. The volatiles are evaporated, the residue is dissolved in 2 mL of MeOH and added to 1.5 g NaI in 12 mL water. The aqueous layer is extracted with 1-butanol and Compound 52 is purified by chromatography on a silica gel column.

Example 24

Preparation of Compound 53

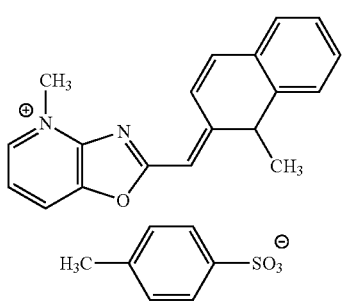

Compound 53

Compound 1 (0.35 g), 0.33 g of 1,2-dimethylquinolinium tosylate, 0.15 mL of triethylamine and 20 mL CH$_2$Cl$_2$ are stirred at room temperature for one hour. The reaction is suction filtered to yield Compound 53, which is purified by chromatography on silica gel.

Example 25

Preparation of Compound 54

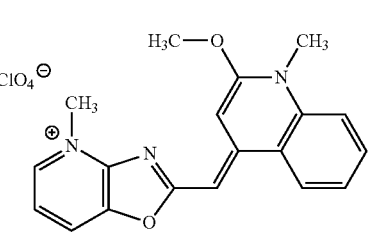

Compound 54

A mixture of 0.173 g of 1,4-dimethyl-2-quinolone, 0.28 mL phosphorus oxychloride, 0.025 mL DMF and 5 mL toluene is heated at 70° C. for 6 hours. Following cooling, 10 mL of methanol is added and the solution is heated at 45° C. for two hours. The volatiles are evaporated, 0.352 g of Compound 1, 0.7 mL of triethylamine and 20 mL of CH$_2$Cl$_2$ are added and the mixture is stirred overnight at room temperature. The solvent is evaporated, the crude product is dissolved in 3 mL methanol and added to 2.5 g of sodium perchlorate in 20 mL water. Compound 54 is collected by filtration, dried, and recrystallized from a mixture of DMF and ethyl acetate.

Example 26

Preparation of Compound 55

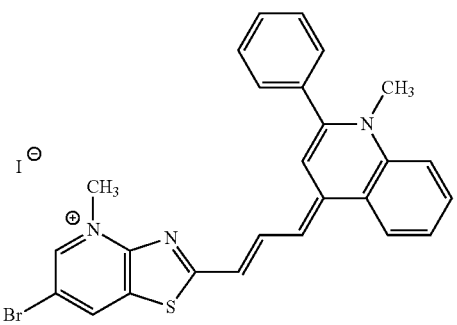

Compound 55

Compound 13 (55 mg) is stirred with 10 mg sodium borohydride for 1.5 hours. Acetic acid (0.6 mL) is added to quench the reaction. The volatiles are evaporated. The crude product is stirred with 0.21 mL triethylamine, 0.19 mL acetic anhydride and 10 mL CH$_2$Cl$_2$. After one hour at room temperature and 30 minutes at 50-60° C., the volatiles are evaporated. Ethyl acetate (10 mL) is added, followed by 5 mL of hexanes. The solid is filtered and the salt thus obtained is stirred overnight at room temperature with a mixture of 65 mg N,N'-diphenylformamidine and 0.1 mL triethylamine in 4 mL dichloroethane. To this is added 150 mg of 1,4-dimethyl-2-phenylquinolinium derivative in 10 mL of acetonitrile, another 0.1 mL of triethylamine and 0.07 mL acetic anhydride. After 1.5 hr at room temperature the volatiles are evaporated, the residue is dissolved in 3 mL methanol and the solution is added to 1 g NaI in 20 mL water. Compound 55 is isolated by suction filtration followed by purification on a silica gel column.

Example 27

Preparation of Compound 56

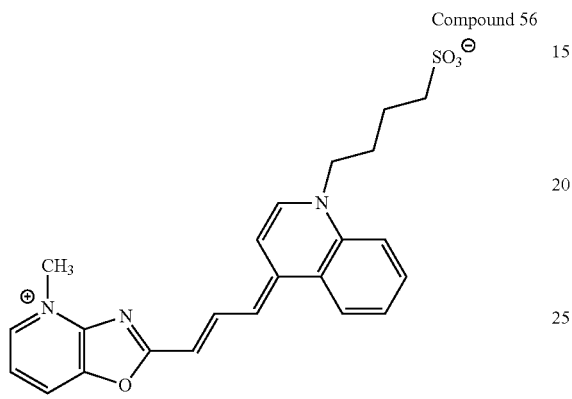

Compound 56

A solution of 1.14 g of Compound 12 in 30 mL of dichloroethane and 1.7 mL triethylamine is stirred at room temperature for 30 minutes. To this is added 0.7 g of N,N'-diphenylformamidine and the mixture is heated at 65° C. for 4 hours. Following cooling, 0.84 g of 1-(4'-sulfobutyl)-4-methylquinolinium inner salt is added, followed by 0.6 mL of acetic anhydride. The mixture is stirred for 30 minutes and Compound 56 is collected by suction filtration.

Example 28

Preparation of Compound 57

Compound 57

To 4-ethyl-1-methyl-2-quinolone in THF at −78° C. is added 1.5 equivalent of phenyllithium, and the resulting solution is kept cold and stirred for one hour. Four equivalents of acetic acid are introduced and the reaction mixture is allowed to stir at room temperature for 3 hours. All the volatile components are then removed under reduced pressure. The resulting residue is dissolved in methylene chloride and one equivalent of Compound 1 (4-methyl-2-methylhiooxazolo[4,5-b] pyridinium tosylate) is introduced followed by 5 equivalents of triethylamine. The resulting product is purified by column chromatography on silica gel.

Example 29

Preparation of Compound 58

Compound 58

To 2,4-dimethyl-thiazolo-[4,5-b]pyridinium tosylate in pyridine at room temperature is added 1.2 equivalent of benzoyl chloride, and the resulting mixture is stirred at room temperature overnight. The resulting intermediate is isolated by silica gel column chromatography. This intermediate is then heated at reflux in 3 equivalents of phosphorous oxychloride for 3 hours. Excess phosphorous oxychloride is removed under reduced pressure and the residue is stirred in methylene chloride with one equivalent of 1,4-dimethylquinolinium tosylate and 4 equivalents of triethylamine to obtain the desired product.

Example 30

Preparation of Compound 59

Compound 59

To a mixture of one equivalent each of 1,4-dimethylquinolinium tosylate and malonaldehyde dianil hydrochloride in acetic acid, is added one equivalent of acetic anhydride and the resulting reaction mixture is heated at 150° C. for 30 minutes. All volatile components are removed under reduced pressure and methylene chloride is introduced followed by the addition of one equivalent of 2-ethyl-4-methyloxazolo[4, 5-b]pyridinium tosylate, 1.5 equivalent of acetic anhydride, and 3 equivalents of triethylamine to obtain the desired product.

Example 31

Preparation of Compound 60

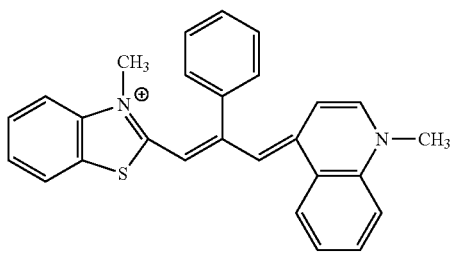

Compound 60

A mixture of 135 mg of 2-benzoylmethylidene-3-methyl-2,3-dihydrobenzothiazole and 230 mg of phosphorous oxychloride is heated at reflux in 5 mL of dichloroethane for 2 hours. Solvent and excess reagents are evaporated under reduced pressure and 30 mL of ethyl acetate is added. After stirring for 30 minutes at room temperature, the resulting solid is collected by filtration and resuspended in 15 mL of methylene chloride. To the mixture is added 165 mg of 1,4-dimethylquinolinium tosylate and 0.14 mL of triethylamine. After stirring at room temperature overnight, the desired product is recovered by recrystallization. When associated with DNA, Compound 60 exhibits excitation and emission wavelengths of 642 nm and 659 nm, respectively.

Example 32

Detecting Double-Stranded DNA in Solution

Samples containing 0.1 ng/mL to 1 microgram/mL double-stranded DNA are prepared in 10 mM Tris-HCl, 1 mM EDTA, pH 7.5. The selected dye of the invention is dissolved in DMSO at a concentration of 1-10 mM and then diluted into the same buffer at a concentration sufficient to achieve final optical densities of 0.1 and 0.01 at 500 nm, 530 nm, 540 nm or 560 nm. Equal volumes (100 microliters each) of DNA sample solution and dye solution at each concentration are combined and mixed gently at room temperature in a microplate well.

Samples are allowed to equilibrate for 5-60 minutes, protected from light, and the fluorescence of the sample is measured using a fluorescence microplate reader. DNA concentration is determined by comparison of the sample fluorescence with a standard curve obtained with that dye for each dye concentration. The sensitivity limit of several dyes in this assay is shown (Table 5).

TABLE 5

Detecting double-stranded DNA in solution.

| Dye | Sensitivity Limit (ng/ml) | |
|---|---|---|
| | Low dye concentration (0.01 OD) | High dye concentration (0.1 OD) |
| Excitation 500 nm/Emission 560 nm | | |
| Compound 43 | 10 | 10 |
| Compound 48 | >10 | 10 |
| Compound 49 | >10 | 20 |
| Compound 53 | >10 | 10 |
| Compound 54 | 1.0 | 10 |
| Excitation 530 nm/Emission 560 nm | | |
| Compound 14 | 1.0 | <10 |
| Compound 15 | 0.5 | 10 |
| Compound 17 | 2.0 | <10 |
| Compound 18 | 0.2-0.5 | <10 |
| Compound 20 | 0.2 | 10 |
| Compound 21 | 0.2 | <10 |
| Compound 27 | 0.5 | 20 |
| Compound 28 | 0.2 | <10 |
| Compound 30 | 1.0 | 10 |
| Compound 31 | 2.0 | 50 |
| Compound 32 | 1.0 | 10 |
| Excitation 540 nm/Emission 570 nm | | |
| Compound 16 | 1.0 | <10 |
| Compound 19 | 0.5 | <10 |
| Compound 22 | 1.0 | 10 |
| Compound 23 | 0.2 | <10 |
| Compound 24 | 5.0 | 10 |
| Compound 25 | 0.5 | <10 |
| Compound 29 | 2.0 | 100 |
| Compound 33 | >10 | 100 |
| Compound 34 | 0.2 | <10 |
| Compound 35 | 0.5 | 10 |
| Excitation 560 nm/Emission 585 nm | | |
| Compound 37 | 2.0 | 10 |
| Compound 38 | 5.0 | 200 |
| Compound 39 | 5.0 | 10 |
| Compound 40 | 1.0 | 10 |
| Compound 41 | >10 | 10 |
| Compound 42 | >10 | 10 |

Example 33

Detecting Oligonucleotides in Solution

Selected dyes of the invention are dissolved in DMSO at 1-10 micromolar concentration, then diluted into 10 mM Tris-HCl, 1 mM EDTA, pH 7.5 to a final optical density of 0.1 or 0.01 at 530 nm or 540 nm. The resulting dye solutions are combined with an equal volume of an 18-base oligodeoxynucleotide sequencing primer solution at concentrations of 0.1 ng/mL to 1 microgram/mL in the same buffer. The resulting mixture is mixed gently and incubated for 5-60 minutes at room temperature, protected from light, and the sample fluorescence is measured in a fluorescence microplate reader. Typical sensitivity limits for some dyes are shown in Table 6.

TABLE 6

Detection of oligonucleotides in solution.

| Dye | Sensitivity Limit (ng/mL) | |
|---|---|---|
| | Low dye concentration (0.01 OD) | High dye concentration (0.1 OD) |
| Excitation 530 nm/Emission 560 nm | | |
| Compound 18 | >10 | <10 |

TABLE 6-continued

Detection of oligonucleotides in solution.

| Dye | Sensitivity Limit (ng/mL) | |
|---|---|---|
| | Low dye concentration (0.01 OD) | High dye concentration (0.1 OD) |
| Compound 20 | 10 | <10 |
| Compound 28 | >10 | <10 |
| Excitation 540 nm/Emission 570 nm | | |
| Compound 23 | 1.0 | <10 |
| Compound 25 | >10 | <10 |
| Compound 19 | >10 | <10 |

Example 34

Detecting RNA in Solution

Selected dyes of the invention are dissolved in DMSO at 1-10 micromolar concentration, then diluted into 10 mM Tris-HCl, 1 mM EDTA, pH 7.5 to a final optical density of 0.1 or 0.01 at 530 nm or 540 nm. These dye solutions are combined with an equal volume of *Escherichia coli* ribosomal RNA at concentrations ranging from 0.25 ng/mL to 1 microgram/mL in microplate wells. The resulting mixtures are mixed gently and incubated for 5-60 minutes at room temperature, protected from light, and the sample fluorescence is measured. Typical sensitivity limits for selected dyes are shown in Table 7.

TABLE 7

Detecting RNA in solution.

| Dye | Sensitivity Limit (ng/mL) | |
|---|---|---|
| | Low dye concentration (0.01 OD) | High dye concentration (0.1 OD) |
| Excitation 530 nm/Emission 560 nm | | |
| Compound 18 | 1.2 | 10 |
| Compound 20 | 5.0 | 200 |
| Compound 28 | >10 | 500 |
| Excitation 540 nm/Emission 570 nm | | |
| Compound 19 | 10 | 20 |
| Compound 23 | 2.5 | 200 |
| Compound 25 | 1.2 | 200 |

Example 35

Detecting Double-Stranded DNA in the Presence of Single-Stranded DNA

Figure 2:
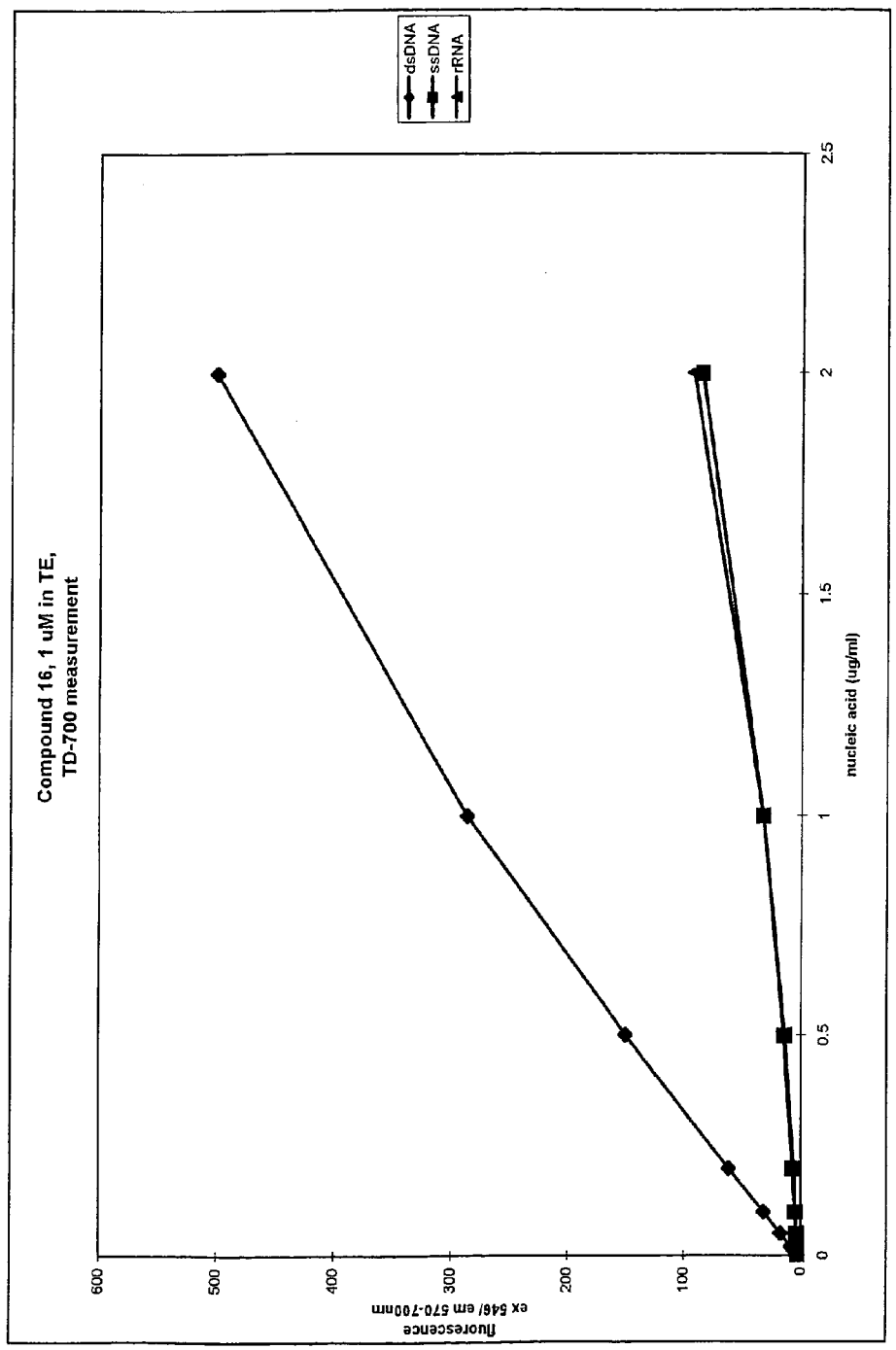
FIG. 2: Shows preferential fluorescent staining of double-stranded DNA by Compound 16 in the presence of single-stranded DNA and RNA, as described in Example 35.

Selected dyes of the invention exhibit high sensitivity for detecting double-stranded DNA, but exhibit little sensitivity for detecting single-stranded nucleic acids, making them particularly useful for quantitating double-stranded DNA in the presence of single-stranded DNA, RNA or oligonucleotide primers (such as might be present in a PCR reaction). Samples containing nucleic acids at a concentration of 2 micrograms/mL are combined with Compound 16, Compound 22, or Compound 24 at a final dye concentration of 1 micromolar in 10 mM Tris-HCl, 1 mM EDTA, pH 7.5, and mixed gently. The resulting mixture is allowed to incubate for 5-60 minutes at room temperature, protected from light, and sample fluorescence is measured using a fluorescence microplate reader, with excitation at 540 nm and emission at 570 nm. Double-stranded DNA is detected preferentially (FIGS. 1 and 2). If, however, the dye concentration is reduced relative to the concentration of single-stranded nucleic acids, the fluorescence upon binding those nucleic acids increases relative to that of the double-stranded DNA-dye complex. Thus the assay is always performed in sufficient dye excess.

Example 36

Detecting Nucleic Acids in Gels

DNA samples are loaded onto agarose or polyacrylamide gels and electrophoresed using standard conditions. Selected dyes of the invention are dissolved in DMSO at a concentration of 1-10 micromolar and diluted into 0.5×TBE buffer to a final concentration of 1 micromolar dye. Gels are incubated for 20-90 minutes in this staining solution, with gentle agitation, at room temperature, protected from light. Nucleic acids are visualized by transillumination at 300 nm, followed by direct visual detection or photography using Polaroid black-and-white print film. Nucleic acids are alternatively visualized by scanning using a FMBIO II laser scanner with a 532 nm frequency-doubled YAG laser source or a charge-coupled device camera system coupled with an ultraviolet (300 nm) light source, or a visible light transilluminator. The sensitivity of detection obtained using these dyes and various imaging instruments is shown in Table 8.

TABLE 8

Sensitivity for detecting double-stranded bacteriophage λ cI857 DNA that is digested with HindIII restriction endonuclease, and separated in agarose gels.

| | Imaging system | | | | | |
|---|---|---|---|---|---|---|
| | POLAROID 667 B&W film | POLAROID 667 B&W film | POLAROID 667 B&W film | BOEHRINGER MANNHEIM LUMIIMAGER CCD | BOEHRINGER MANNHEIM LUMIIMAGER CCD | HITACHI FMBIO II laser scanner |
| Excitation source | FOTODYNE 300 nm trans. | FOTODYNE 254 nm epi. | DARK READER visible light box | 300 nm trans. 520 nm em. | 300 nm trans. 545 nm em | 532 nm freq.-doubled YAG laser |
| Cpd. 15 | 240 pg | 60 pg | 480 pg | 210 pg | 100 pg | 100 pg |
| Cpd. 16 | 120 pg | 30 pg | 240 pg | 210 pg | 50 pg | 25 pg |
| Cpd. 18 | 120 pg | 60 pg | nd | 210 pg | 100 pg | 50 pg |
| Cpd. 20 | 480 pg | 120 pg | nd | 830 pg | 210 pg | 50 pg |
| Cpd. 21 | 120 pg | 60 pg | nd | 420 pg | 50 pg | 50 pg |
| Cpd. 22 | 120 pg | 30 pg | 60 pg | 830 pg | 50 pg | 7 pg |

TABLE 8-continued

Sensitivity for detecting double-stranded bacteriophage λ cI857 DNA that is digested with HindIII restriction endonuclease, and separated in agarose gels.

| | Imaging system | | | | | |
|---|---|---|---|---|---|---|
| | POLAROID 667 B&W film | POLAROID 667 B&W film | DARK READER visible light box | BOEHRINGER MANNHEIM LUMIIMAGER CCD | | HITACHI FMBIO II laser scanner |
| Excitation source | FOTODYNE 300 nm trans. | FOTODYNE 254 nm epi. | DARK READER visible light box | 300 nm trans. 520 nm em. | 300 nm trans. 545 nm em | 532 nm freq.-doubled YAG laser |
| Cpd. 23 | 120 pg | 60 pg | 240 pg | 830 pg | 100 pg | 5 pg |
| Cpd. 24 | 60 pg | 30 pg | 120 pg | 420 pg | 50 pg | 5 pg |
| Cpd. 25 | 120 pg | 120 pg | 240 pg | 1.7 ng | 100 pg | 25 pg | nd indicates that a value was not determined for this dye with this gel imager.

Example 37

Detecting Nucleic Acids Arrayed on Glass Slides

Nucleic acid arrays are prepared on glass slides, using an automated arraying robot. The slide surface is optionally blocked with a solution of 0.1% Ficoll (Type 400, Amersham Pharmacia) and 0.1% polyvinylpyrrolidone. Arrays are allowed to dry and then overlaid with a solution containing 1 micromolar dye in 10 mM Tris-HCl, 1 mM EDTA, pH 7.5. Suitable dyes for this purpose include Compound 15, Compound 16, Compound 22, Compound 23, Compound 24, and Compound 25. Slides are incubated with the overlay solution for 5-60 minutes at room temperature, with light protection, and then are washed briefly in the same buffer without the dye. The amount of nucleic acid in each spot on the array can be measured by comparison of the fluorescence of an unknown sample with that of standards of known concentration, which are applied to the same slide. Fluorescence measurement is performed using a fluorescence microscope with a mercury or xenon lamp, equipped with appropriate optical filters, a charge-coupled device and image analysis software, or using a dedicated array reader with a 532 nm or 546 nm excitation source, such as the GENEARRAY 2000 (General Scanning).

Example 38

Detecting Proteins in Solution

Figure 3:
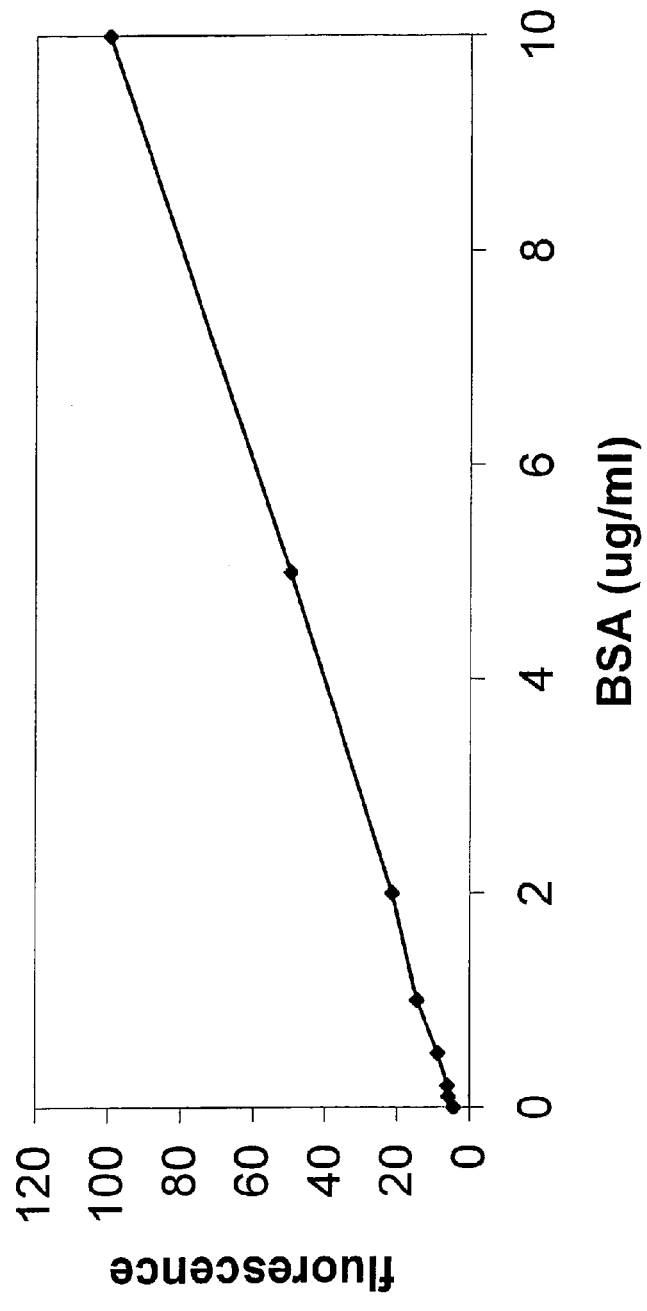
FIG. 3: Shows detection of bovine serum albumin using Compound 51, as described in Example 38.
Figure 4:
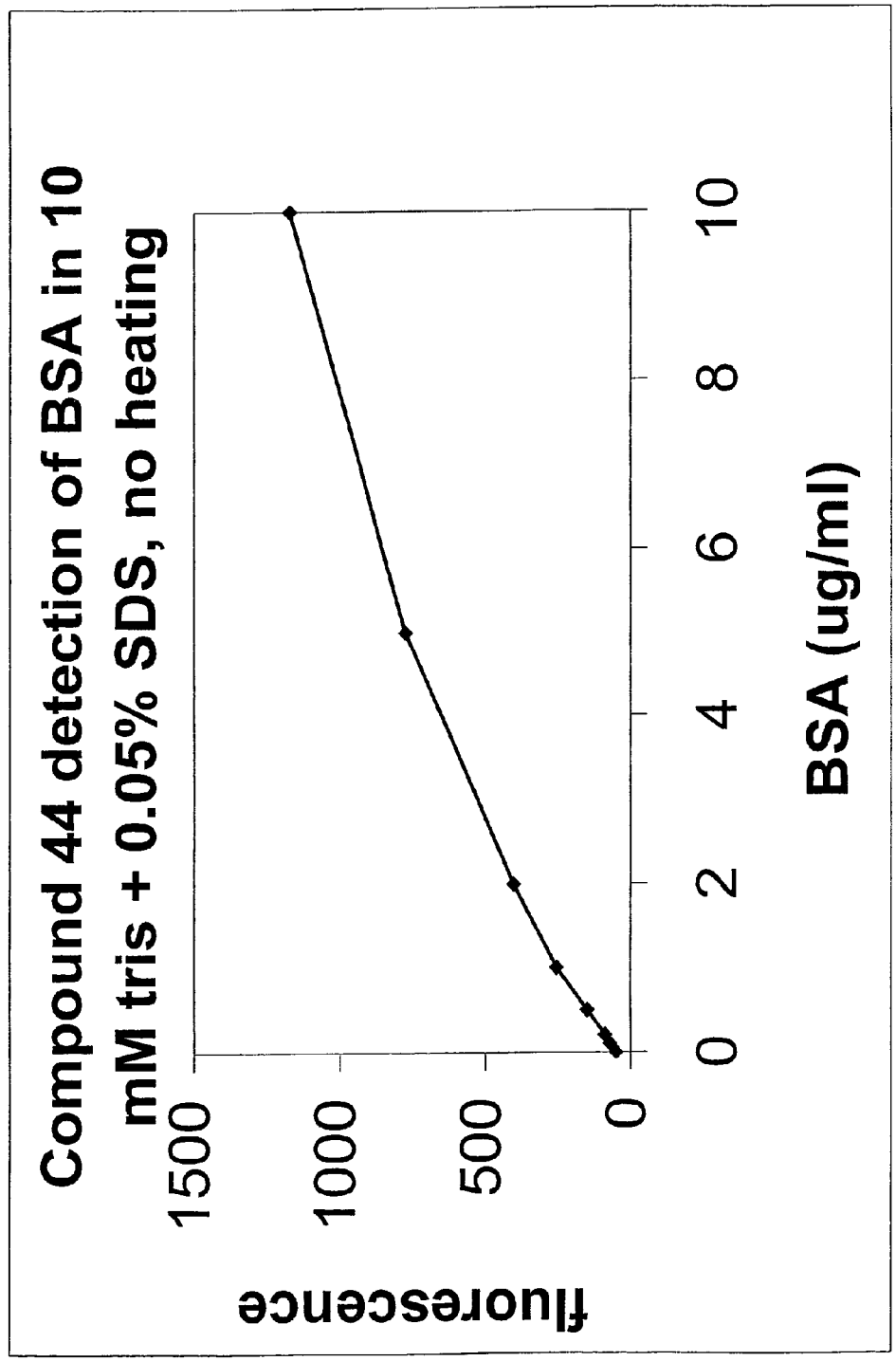
FIG. 4: Shows detection of bovine serum albumin using Compound 44, as described in Example 38.

Compound 51 and Compound 44 are dissolved in DMSO at 1-10 mM and then diluted into 10 mM Tris-HCl, 1 mM EDTA, pH 7.5, containing 0.05% sodium dodecyl sulfate, to a final concentration of 2 micromolar. This dye solution is combined with samples containing bovine serum albumin at 100 ng/mL to 10 micrograms/mL. Samples are optionally incubated for 10 minutes at 90° C. and then cooled to room temperature, or are incubated for 5-60 minutes at room temperature. Fluorescence is measured using a fluorescence microplate reader with excitation at 540 nm and emission at 590 nm for Compound 44 and with excitation at 600 nm and emission at 670 nm for Compound 51. The fluorescence signal obtained from Compound 44 or 51 in buffer alone (control) is subtracted from the fluorescence recorded for the protein-containing samples in order to determine the intensity of the signal that is due to the presence of protein. Protein concentrations are then determined by comparison of the signal intensity thus obtained with the signals obtained using a dilution series of known concentration prepared using either the same protein or a protein standard, such as bovine serum albumin. The sensitivity limit for either dye under either condition is about 100 ng/mL bovine serum albumin (FIGS. 3 and 4).

Example 39

Detection of Proteins in Sodium Dodecyl Sulfate (SDS)-Polyacrylamide Gels

The pure protein or mixture of proteins of interest is prepared in Loading Buffer (50 mM Tris-HCl, pH 6.8, 2% SDS, 10% glycerol, and 0.015% bromophenol blue). Dithiothreitol is added to each sample, to a final concentration of 0.1 M. The samples are heated for 4-5 minutes at 90-95 □C and loaded onto a 15% Tris-glycine polyacrylamide mini- or full-sized gel containing 0.05%-0.1% SDS, with a 4% stacking gel. The gel is electrophoresed under standard conditions, in a standard Tris-glycine buffer containing 0.05%-0.1% SDS. The resulting gel is transferred to a small staining dish containing a 1-3 µM solution of Compound 25 in 7.5% acetic acid (in water). The staining solution is then covered with foil to protect it from room light and gently agitated for 45 minutes-1 hour. After 10 minutes, the protein bands are readily apparent, but sensitivity improves over about 30-40 minutes. The gel is then removed from the staining dish, rinsed briefly in 7.5% acetic acid and transferred directly to a UV-transilluminator. The gel, with the stained protein bands is photographed using 300 nm transillumination and black and white POLAROID 667 print film with a Wratten 9 gelatin filter. The stained bands appear visually as brightly fluorescent orange bands. Proteins appear as white bands on a grey to black background in the POLAROID photograph.

Although Compound 25 is used in this procedure, a variety of other dyes of the invention are useful as electrophoretic gel stains, yielding stained gels that possess bands having fluorescence emission from yellow to red.

Example 40

Detection of Apoptosis

A 1 mM solution of Compound 27 in DMSO is prepared. Jurkat human T-cell leukemia cells are treated with 10 µM camptothecin to induce apoptosis. A sample of the cells ($1 \times 10^8$ cells/mL) is incubated with enough of the Compound 27 stock solution to give a final dye concentration of 0.1 µM, and sufficient propidium iodide to give a final concentration of 1.5 µM. After incubating for 30 minutes on ice, the cell samples are analyzed on a FacsVantage flow cytometer using 488-argon laser excitation, with emission at 530/30 and 675/20. Apoptotic cells are compared to control cells that were incubated with the same final concentration of DMSO used in the staining solution. A plot of FL1 versus FL3 shows that Compound 27 is capable of differentiating between apoptotic and normal cells. Late stage apoptotic and necrotic cells are stained with propidium iodide.

It is to be understood that, while the foregoing invention has been described in detail by way of illustration and example, numerous modifications, substitutions, and alterations are possible without departing from the spirit and scope of the invention as described in the following claims.

All publications, patents and patent applications mentioned in this specification are herein incorporated by reference to the same extent as if each individual publication, patent or patent application was specifically and individually indicated to be incorporated by reference.

What is claimed is:

1. A method for detecting double-stranded DNA in the presence of single-stranded nucleic acid in a sample, wherein the method comprises the steps:

a) combining the sample with a staining solution, wherein the staining solution comprises one or more dye compounds having a structure according to

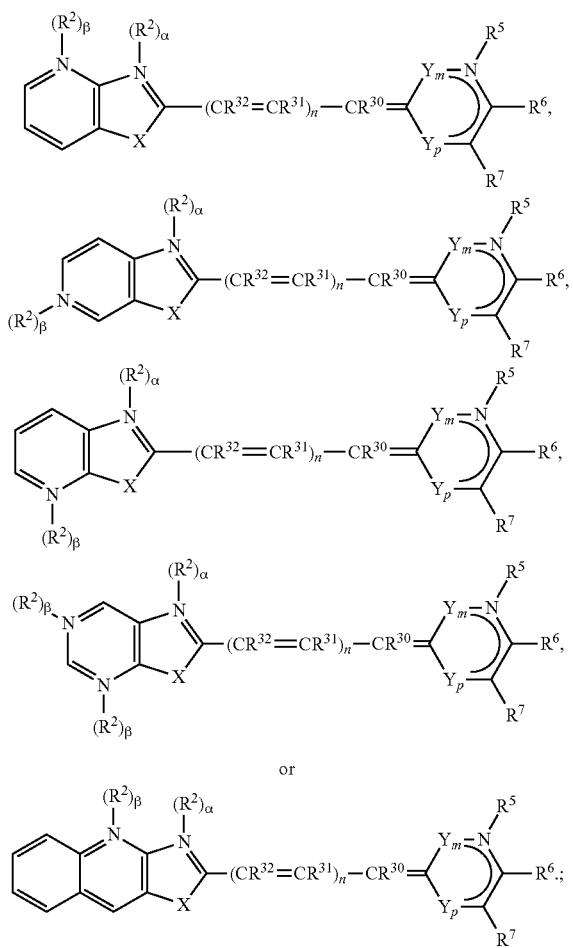

or wherein

X is O, S, Se, $NR^{15}$, or $CR^{16}R^{17}$, where $R^{15}$ is H or an alkyl group having 1-6 carbons; and $R^{16}$ and $R^{17}$, which may be the same or different; are independently $C_1$-$C_6$ alkyl groups, or $R^{16}$ and $R^{17}$ taken in combination complete a 5- or 6-membered saturated ring;

$R^2$ is selected from the group consisting of -L-Rx, -L-Sc, TAIL, BRIDGE and a $C_1$-$C_6$ alkyl group that is optionally substituted by sulfo, carboxy, amino, substituted amino or substituted ammonium, wherein α is 0 or 1 and β is 0 or 1 provided that α+β=1; and TAIL is a heteroatom-containing moiety;

wherein Rx is a reactive group; Sc is a conjugated substance; and L and BRIDGE are independently a single covalent bond, or a covalent linkage;

Y is —$CR^3$=$CR^4$—wherein p and m=0 or 1, such that p+m=1;

$R^3$, $R^4$, $R^6$, and $R^7$ are independently selected from the group consisting of hydrogen, a $C_1$-$C_6$ alkyl, a halogen, a CYCLIC SUBSTITUENT, —$OR^8$, —$SR^8$, —($NR^8R^9$), TAIL; BRIDGE, -L-Rx and -L-Sc;

where $R^8$ and $R^9$ are independently a $C_1$-$C_6$ alkyl group, 1-2 alicyclic or aromatic rings; or $R^8$ and $R^9$ taken in combination are —($CH_2$)$_2$—V—($CH_2$)$_2$—where V is a single bond, —O—, —$CH_2$—, or —$NR^{10}$—, where $R^{10}$ is H or a $C_1$-$C_6$ alkyl;

wherein CYCLIC SUBSTITUENT is a substituted or unsubstituted aryl, heteroaryl or $C_3$-$C_{10}$ cycloalkyl;

or $R^6$ and $R^7$ form a fused aromatic ring —$R^{11}$=$R^{12}$—$R^{13}$=$R^{14}$—wherein $R^{11}$, $R^{12}$, $R^{13}$, and $R^{14}$ are independently selected from the group consisting of hydrogen, $C_1$-$C_6$ alkyl group, —$OR^8$, —$SR^8$, —($NR^8R^9$), a CYCLIC SUBSTITUENT, TAIL, BRIDGE, -L-Rx and -L-Sc;

$R^5$ is independently selected from the group consisting of a $C_1$-$C_6$ alkyl group, a CYCLIC SUBSTITUENT, TAIL, BRIDGE, -L-Rx and -L-Sc; or $R^5$ is absent;

$R^{30}$, $R^{31}$, and $R^{32}$ are independently selected from the group consisting of hydrogen, $C_1$-$C_6$ alkyl, $C_3$-$C_{10}$ cycloalkyl, aryl, and heteroaryl, wherein n=0, 1 or 2;

wherein BRIDGE, when present, is bound to the dye compound or another unsymmetrical cyanine dye;

b) incubating the sample and the staining solution for a sufficient amount of time to form a dye-nucleic acid complex;

c) illuminating the complex with an appropriate wavelength whereby the double-stranded DNA is detected in the presence of single-stranded nucleic acid.

2. The method according to claim 1, wherein X is O, n is 0, $R^2$ is methyl, and $R^6$ and $R^7$ taken together form a fused aromatic ring —$R^{11}$=$R^{12}$—$R^{13}$=$R^{14}$—wherein $R^{11}$, $R^{12}$, $R^{13}$, and $R^{14}$ are independently selected from the group consisting of hydrogen, $C_1$-$C_6$ alkyl, and —$OR^8$.

3. The method according to claim 1, wherein $R^5$ is a CYCLIC SUBSTITUENT that is an aryl group and $R^4$ is a $C_1$-$C_6$ alkyl group.

4. The method according to claim 1, wherein $R^5$ is a $C_1$-$C_6$ alkyl group and $R^4$ is a CYCLIC SUBSTITUENT that is an aryl group.

5. The method according to claim 1, wherein the dye is substituted by at least one TAIL substituent.

6. The method according to claim 5, wherein the TAIL is according to formula LINK-SPACER-CAP;

wherein LINK is a single covalent bond, an ether linkage (—O—), a thioether linkage (—S—), or an amine linkage (—$NR^{20}$—); where $R^{20}$ is hydrogen, a $C_1$-$C_8$ alkyl group or SPACER-CAP;

SPACER is a covalent linkage; and

CAP is —$OR^{21}$, —$SR^{21}$, —$NR^{21}R^{22}$, or —$NR^{21}R^{22}R^{23}$; where $R^{21}$, $R^{22}$, and $R^{23}$ are independently selected from the group consisting of hydrogen, a $C_1$-$C_8$ alkyl, and a $C_1$-$C_8$ cycloalkyl wherein the alkyl or cycloalkyl are optionally substituted by one or more substituents selected from the group consisting of halogen, hydroxyl, a $C_1$-$C_8$ alkoxy, amino, carboxy, sulfo, and phenyl, where the phenyl is optionally substituted by one or more substituents selected from the group consisting of halogen, hydroxyl, a $C_1$-$C_8$ alkoxy, amino, a $C_1$-$C_8$ aminoalkyl, a $C_1$-$C_8$ sulfoalkyl, and a $C_1$-$C_8$ carboxyalkyl; or one or more $R^{21}$, $R^{22}$, and $R^{23}$, taken in combination with $R^{20}$ and SPACER, or with SPACER alone, forms a 5- or 6-membered ring.

7. The method according to claim 6, wherein $R^4$ or $R^5$ is independently a TAIL or a CYCLIC SUBSTITUENT substituted by TAIL.

8. The method according to claim 7, wherein $R^4$ is a TAIL and $R^5$ is a $C_1$-$C_6$ alkyl group.

9. The method according to claim 8, wherein CAP is —$NR^{21}R^{22}$, where $R^{21}$ and $R^{22}$ are independently $C_1$-$C_6$ alkyl groups.

10. The method according to claim 8, wherein CAP is —$NR^{21}R^{22}R^{23}$, where $^{21}R^{22}$, and $R^{23}$ are independently $C_1$-$C_6$ alkyl groups.

11. The method according to claim 7, wherein $R^5$ is a CYCLIC SUBSTITUENT that is an aryl or heteroaryl and $R^4$ is a TAIL, where CAP is —$OR^{21}$ or —$SR^{21}$.

12. The method according to claim 7, wherein $R^5$ is a TAIL.

13. The method according to claim 12, wherein CAP is —$NR^{21}R^{22}R^{23}$, where $R^{21}$, $R^{22}$ and $R^{23}$ are independently $C_1$-$C_6$ alkyl groups.

14. The method according to claim 1, wherein the staining solution comprises one or more dyes having the structure of Compound 15, Compound 16, Compound 22, Compound 23, Compound 24, or Compound 25.

15. The method according to claim 1, wherein the double stranded DNA is in solution, immobilized on a solid or semi-solid matrix, or present in a biological structure.

16. The method according to claim 1, further comprising quantifying the double-stranded DNA present in the sample.

17. The method according to claim 1, wherein the fluorescence of the dye when associated with double-stranded DNA is distinguishable from the fluorescence of the dye when associated with single-stranded nucleic acid.

18. The method according to claim 15, wherein the biological structure is a biological cell or portion thereof, virus particle or tissue section.

19. The method according to claim 15, wherein the double-stranded DNA is in solution that is free from cells or portions thereof.

20. The method according to claim 15, wherein the solid or semi-solid matrix is a polymeric gel, an array, a glass slide, a polymeric microparticle, a membrane a silica-based support, or a plastic-based support.

* * * * *